US007816111B2

(12) United States Patent
Davis et al.

(10) Patent No.: US 7,816,111 B2
(45) Date of Patent: Oct. 19, 2010

(54) GLUCOSE DEHYDROGENASE POLYPEPTIDES AND RELATED POLYNUCLEOTIDES

(75) Inventors: S. Christopher Davis, San Francisco, CA (US); Stephane J. Jenne, Burlingame, CA (US); Anke Kebber, Palo Alto, CA (US); Lisa Marie Newman, Redwood City, CA (US)

(73) Assignee: Codexis, Inc., Redwood City, CA (US)

( * ) Notice: Subject to any disclaimer, the term of this patent is extended or adjusted under 35 U.S.C. 154(b) by 411 days.

(21) Appl. No.: 10/915,927

(22) Filed: Aug. 11, 2004

(65) Prior Publication Data

US 2005/0095619 A1    May 5, 2005

Related U.S. Application Data

(60) Provisional application No. 60/494,300, filed on Aug. 11, 2003, provisional application No. 60/545,657, filed on Feb. 18, 2004.

(51) Int. Cl.
*C12N 9/04* (2006.01)
*C12N 15/00* (2006.01)
*C12N 1/20* (2006.01)
*C12Q 1/32* (2006.01)
*C12Q 1/00* (2006.01)
*C12P 21/04* (2006.01)
*C07H 21/04* (2006.01)
*C12Q 1/68* (2006.01)

(52) U.S. Cl. .............. 435/190; 435/4; 435/6; 435/69.1; 435/71.1; 435/26; 435/252.3; 435/320.1; 435/440; 536/23.2

(58) Field of Classification Search ............... None
See application file for complete search history.

(56) References Cited

U.S. PATENT DOCUMENTS

| | | | |
|---|---|---|---|
| 4,397,952 A | 8/1983 | Hoerschelmann et al. | |
| 4,542,098 A | 9/1985 | Vandecasteele et al. | |
| 4,877,733 A | 10/1989 | Takahashi et al. | |
| 5,114,853 A | 5/1992 | Makino et al. | |
| 5,114,854 A | 5/1992 | Bertholdt | |
| 5,126,256 A | 6/1992 | Ebeling et al. | |
| 5,298,411 A | 3/1994 | Sogabe et al. | |
| 6,001,615 A | 12/1999 | Reeve | |
| 6,344,569 B1 | 2/2002 | Mitsuda et al. | |
| 6,472,544 B1 | 10/2002 | Kizaki et al. | |
| 6,596,879 B2 | 7/2003 | Bosch et al. | |
| 6,645,746 B1 | 11/2003 | Kizaki et al. | |
| 6,689,591 B2 | 2/2004 | Müller et al. | |
| 7,125,693 B2 * | 10/2006 | Davis et al. | 435/128 |
| 7,132,267 B2 * | 11/2006 | Davis et al. | 435/128 |

FOREIGN PATENT DOCUMENTS

EP    1213354 A2    6/2002

| | | |
|---|---|---|
| WO | WO 00/49039 | 8/2000 |
| WO | WO 2004/015132 A2 | 2/2004 |
| WO | WO 2005/045016 A3 | 5/2005 |

OTHER PUBLICATIONS

Lampel et al. Characterization of the developmentally regulated *Bacillus subtilis* glucose dehydrogenase gene. J. Bacteriol. 166 (1), 238-243 (1986).*
Branden et al. (introduction to Protein Structure, Garland Publishing Inc., New York, p. 247, 1991.*
Persson et al. Purification and site-specific immobilization of genetically engineered glucose dehydrogenase on thiopropyl-Sepharose. FEBS Lett. Sep. 17, 1990;270(1-2):41-4.*
Manjon A., et al., "Increased Activity of glucose Dehydrogenase Co-Immobilized With a Redox Mediator in a Bioreactor With Electrochemical NAD+ Regeneration", Biotechnology Letters, vol. 24, No. 15; Aug. 2002, pp. 1227-1232.
Lampel, et al., Apr. 1986, "Characterization of the Developmentally Regulated *Bacillus subtilis* Glucose Dehydrogenase Gene," *J Bacteriol.*, 166(1):238-243.
Manjon, et al., Aug. 2002, "Increased Activity of Glucose Dehydrogenase Co-immobilized with a Redox Mediator in a Bioreactor with Electrochemical NAD+ Regeneration," *Biotechnol. Lett*, 24(15):1227-1232.
Baik et al., 2003, "Significantly enhanced stability of glucose dehydrogenase by directed evolution," Appl. Micro. Biotech. 61:329-355.
Baik et al., 2005, "Cooperative Effect of Two Surface Amino Acid Mutations (Q252L and E170K) in Glucose Dehydrogenase from *Bacillus megaterium* IWG3 on Stabilization of Its Oligomeric State," Appl. Environ. Microbiol. 71(6):3285-3293.
Fortnagel et al., 1986, "Sequence Homologies of Glucose-Dehydogenases of *Bacillus megaterium* and *Bacillus subtilis*," Journal of Theoretical Biology 120(4):489-497.
Heilmann et al., 1988, "Identification and isolation of glucose dehydrogenase genes of *Bacillus megaterium* M1286 and their expression in *Escherichia coli*," Eur J Biochem. 174(3):485-90.
Ramaley et al., 1983 "Glycerol protection and purification of *Bacillus subtilis* glucose dehydrogenase," J. Biol. Chem. 258:12558-12565.
Yamamoto et al., 2001, "Crystal Structure of Glucose Dehydrogenase from *Bacillus megaterium* IWG3 at 1.7Å Resolution," J. Biochem. 129:303-312.
International Search report for PCT/US2004/026194 dated May 10, 2005.
European Search Report for EP04816807.4 dated Jun. 10, 2008.
Written Opinion of Singapore Application No. 200600859-3 dated Aug. 11, 2003.

(Continued)

*Primary Examiner*—Yong D Pak
(74) *Attorney, Agent, or Firm*—Dechert LLP

(57) ABSTRACT

The present invention is directed to glucose dehydrogenase (GDH) polypeptides that have enhanced GDH activity and/or thermostability relative to the backbone wild-type glucose dehydrogenase polypeptide. In addition, the present invention is directed to a polynucleotide that encodes for the GDH polypeptides of the present invention, to nucleic acid sequences comprising the polynucleotides, to expression vectors comprising the polynucleotides operatively linked to a promoter, to host cells transformed to express the GDH polypeptides, and to a method for producing the GDH polypeptides of the present invention.

23 Claims, 4 Drawing Sheets

OTHER PUBLICATIONS

Ivanova et al., 2003, "Genome sequence of *Bacillus cereus* and comparative analysis with *Bacillus anthracis*," *Nature*, 423(6935):87-91.

Maurer et al., 1987, "Reversible pH-Induced Dissociation of Glucose Dehydrogenase from *Bacillus megaterium* II. Kinetics and Mechanism," *Z. Naturforsch.* 42c, 907-915.

Mitamura et al., 1990, "Structure of Isozyme Genes of Glucose Dehydrogenase from *Bacillus megaterium* IAM1030", *J. Ferment. Bioeng.* 70(6):363-369.

Pauly et al., 1975, "D-glucose dehydrogenase from *Bacillus megaterium* M 1286: Purification, Properties and Structure," *Hoppe-Seyler's Z. Physiol. Chem.*, 356(10):1613-23.

Vasantha, et al., 1983, "Isolation of a developmental gene of *Bacillus subtilis* and its expression in *Escherichia coli.*," *Proc. Nat. Acad. Sci. U.S.A.*, 80(3):785-9.

Yamane et al., 1996, "The 25-36 region of the *Bacillus szlbtilis* chromosome: determination of the sequence of a 146 kb segment and identification of 113 genes," *Microbiology* 142:3047-3056.

\* cited by examiner

| SEQ ID NO | WO 200049039 | US 5114853 | S06-3 | JP 04258293 | JP 04258289 | JP 02072878 | EP955375 | EP285949 DE3711881 | EP1213354 | EP1013758 | DE3931716 | AAA22463 (NCBI No) |
|---|---|---|---|---|---|---|---|---|---|---|---|---|
| 78 | 82.8 | 82.0 | 99.2 | 81.6 | 82.0 | 82.0 | 99.2 | 82.0 | 83.1 | 99.2 | 80.8 | 98.1 |
| 76 | 82.8 | 82.0 | 98.9 | 81.6 | 82.0 | 82.0 | 98.9 | 82.0 | 83.1 | 98.9 | 80.8 | 97.7 |
| 74 | 82.8 | 82.4 | 99.6 | 82.0 | 82.0 | 82.4 | 99.6 | 82.0 | 83.5 | 99.6 | 80.8 | 98.5 |
| 72 | 82.0 | 81.2 | 98.1 | 80.8 | 81.2 | 81.2 | 98.1 | 81.2 | 82.4 | 98.1 | 80.1 | 96.9 |
| 70 | 82.4 | 82.0 | 99.2 | 81.6 | 81.6 | 82.0 | 99.2 | 81.6 | 83.1 | 99.2 | 80.5 | 98.1 |
| 68 | 82.4 | 82.0 | 98.9 | 81.6 | 81.6 | 82.0 | 98.9 | 81.6 | 83.1 | 98.9 | 80.5 | 97.7 |
| 66 | 82.0 | 81.2 | 98.1 | 80.8 | 81.2 | 81.2 | 98.1 | 81.2 | 82.4 | 98.1 | 80.5 | 96.9 |
| 64 | 82.4 | 81.6 | 98.5 | 81.2 | 81.6 | 81.6 | 98.5 | 81.6 | 82.8 | 98.5 | 80.5 | 97.3 |
| 62 | 82.0 | 81.6 | 98.5 | 81.2 | 81.2 | 81.6 | 98.5 | 81.2 | 82.8 | 98.5 | 80.5 | 97.3 |
| 60 | 81.6 | 81.2 | 98.1 | 80.8 | 80.8 | 81.2 | 98.1 | 80.8 | 82.4 | 98.1 | 79.7 | 96.9 |
| 58 | 81.6 | 81.2 | 98.5 | 80.8 | 80.8 | 81.2 | 98.5 | 80.8 | 82.4 | 98.5 | 79.7 | 97.3 |
| 56 | 82.8 | 82.4 | 99.6 | 82.0 | 82.0 | 82.4 | 99.6 | 82.0 | 83.5 | 99.6 | 80.8 | 98.5 |
| 54 | 82.8 | 82.4 | 99.2 | 82.0 | 82.0 | 82.4 | 99.2 | 82.0 | 83.5 | 99.2 | 80.8 | 98.1 |
| 52 | 82.8 | 97.3 | 83.5 | 96.9 | 97.3 | 97.3 | 83.5 | 82.0 | 99.2 | 83.5 | 95.4 | 82.8 |
| 50 | 82.4 | 82.0 | 99.6 | 81.6 | 81.6 | 82.0 | 99.6 | 81.6 | 83.1 | 99.6 | 80.8 | 98.5 |
| 48 | 82.8 | 82.0 | 99.6 | 81.6 | 81.6 | 82.0 | 99.6 | 82.0 | 83.1 | 99.6 | 80.8 | 98.5 |
| 46 | 82.4 | 82.0 | 99.6 | 81.6 | 81.6 | 82.0 | 99.6 | 82.0 | 83.1 | 99.6 | 80.5 | 98.5 |
| 44 | 82.4 | 82.4 | 99.6 | 82.0 | 82.0 | 82.4 | 99.6 | 81.6 | 83.1 | 99.6 | 80.5 | 98.5 |
| 40 | 82.8 | 82.4 | 99.2 | 81.6 | 81.6 | 82.0 | 99.2 | 82.0 | 83.1 | 99.2 | 80.8 | 98.1 |
| 38 | 82.4 | 82.0 | 99.6 | 81.6 | 81.6 | 82.0 | 99.6 | 81.6 | 83.1 | 99.6 | 80.5 | 98.5 |

FIG. 2A

| SEQ ID NO | WO 2000049039 | US 5114853 | S06-3 | JP 04258293 | JP 04258289 | JP 02072878 | EP955375 | EP285949 DE3711881 | EP1213354 | EP1013758 | DE3931716 | AAA22463 (NCBI No) |
|---|---|---|---|---|---|---|---|---|---|---|---|---|
| 36 | 82.8 | 82.4 | 99.6 | 82.0 | 82.0 | 82.4 | 99.6 | 82.0 | 83.5 | 99.6 | 80.8 | 98.5 |
| 34 | 82.8 | 82.4 | 99.2 | 82.0 | 82.0 | 82.4 | 99.2 | 82.0 | 83.5 | 99.2 | 80.8 | 98.1 |
| 32 | 82.4 | 82.0 | 99.6 | 81.6 | 81.6 | 82.0 | 99.6 | 81.6 | 83.1 | 99.6 | 80.5 | 98.5 |
| 30 | 82.8 | 82.4 | 99.2 | 82.0 | 82.0 | 82.4 | 99.2 | 82.0 | 83.5 | 99.2 | 80.8 | 98.1 |
| 28 | 82.8 | 82.4 | 99.2 | 82.0 | 82.0 | 82.4 | 99.2 | 82.0 | 83.5 | 99.2 | 80.8 | 98.1 |
| 26 | 82.8 | 82.4 | 99.6 | 82.0 | 82.0 | 82.4 | 99.6 | 82.0 | 83.5 | 99.6 | 80.8 | 98.5 |
| 24 | 82.4 | 82.0 | 99.6 | 81.6 | 81.6 | 82.0 | 99.6 | 81.6 | 83.1 | 99.6 | 80.5 | 98.5 |
| 22 | 82.8 | 82.4 | 99.6 | 82.0 | 82.0 | 82.4 | 99.6 | 82.0 | 83.5 | 99.6 | 80.5 | 98.5 |
| 20 | 82.4 | 82.0 | 99.6 | 81.6 | 81.6 | 82.0 | 99.6 | 81.6 | 83.1 | 99.6 | 80.5 | 98.5 |
| 18 | 82.8 | 82.4 | 99.6 | 82.0 | 82.0 | 82.4 | 99.6 | 82.0 | 83.5 | 99.6 | 80.5 | 98.5 |
| 16 | 82.4 | 82.0 | 99.2 | 81.6 | 81.6 | 82.0 | 99.2 | 81.6 | 83.1 | 99.2 | 80.5 | 98.1 |
| 14 | 82.0 | 81.6 | 99.2 | 81.2 | 81.2 | 81.6 | 99.2 | 81.2 | 82.8 | 99.2 | 80.1 | 98.1 |
| 12 | 82.0 | 81.6 | 99.2 | 81.2 | 81.2 | 81.6 | 99.2 | 81.6 | 82.8 | 99.2 | 80.1 | 98.1 |
| 10 | 82.4 | 82.0 | 99.6 | 81.6 | 81.6 | 82.0 | 99.6 | 81.6 | 83.1 | 99.6 | 80.5 | 98.5 |
| 8 | 82.8 | 82.4 | 99.6 | 82.0 | 82.0 | 82.4 | 99.6 | 82.0 | 83.5 | 99.6 | 80.8 | 98.5 |
| 6 | 82.4 | 82.0 | 99.6 | 81.6 | 81.6 | 82.0 | 99.6 | 81.6 | 83.1 | 99.6 | 80.5 | 98.5 |

GLUCOSE DEHYDROGENASE POLYPEPTIDES AND RELATED POLYNUCLEOTIDES

CROSS REFERENCE TO RELATED APPLICATIONS

This application claims benefit under 35 U.S.C. §119(e) to U.S. provisional application Ser. No. 60/494,300, filed Aug. 11, 2003 and U.S. provisional application Ser. No. 60/545,657, filed Feb. 18, 2004.

SEQUENCE LISTING SUBMISSION ON COMPACT DISC

In addition to the originally filed paper copy, the present application included a Sequence Listing Submitted on compact disc under 37 C.F.R. §§1.821(c) and 1.821(e) and is incorporated herein by reference in its entirety. Four copies of the Sequence Listing, comprising one on each of the three compact discs (CDs) and one originally filed paper copy are provided. Originally filed Copies 1 and 2 on CD are identical to each other and to the originally filed paper copy and to the subsequently filed CRF on CD. Each electronic copy of the Sequence Listing was created on Jul. 30, 2004 with a file size of 511 KB. The file names are as follows: Copy 1—15076U503 SEQ LISTING 1-168.txt; Copy 2—15076U503 SEQ LISTING 1-168.txt; and CRF—15076U503 SEQ LISTING 1-168.txt.

FIELD OF THE INVENTION

The present invention is related to the field of enzymology, and particularly to the field of glucose dehydrogenase enzymology. More specifically, the present invention is directed to glucose dehydrogenase polypeptides having improved enzymatic activity (i.e., high substrate turnover) and stability, and to polynucleotides sequences encoding for the improved glucose dehydrogenase polypeptides. The present invention is useful because the glucose dehydrogenase polypeptides can be coupled to oxido- or reductase enzymes to produce synthetic organic chemicals or precursors in high yields.

BACKGROUND OF THE INVENTION

Glucose dehydrogenase [EC1.1.1.47] or "GDH" catalyzes the conversion of β-glucose and nicotinamide adenine dinucleotide (NAD) to gluconolactone and reduced nicotinamide adenine dinucleotide (NADH). NAD serves as a cofactor in this reaction and may be phosphorylated in the form of NADP. GDH is an important enzyme for use in clinical tests and the food industry. GDH is also applied as a catalyst for chemical conversions where it serves a role in the regeneration of NADH and NADPH in enzymatic carbonyl reductions, such as aldehydes and ketones.

Bacillus species have been an excellent source of GDH. The enzyme from B. megaterium M1286 was purified to homogeneity and found to be a homotetramer of 30,000 DA subunits with pH optimum of 8.0-9.0 depending on buffer conditions and uses either nicotinamide adenine dinucleotide (NAD) or nicotinamide adenine dinucleotide phosphate (NADP) as cofactor (Pauly H. E. and Pfleiderer G., Hoppe Seylers Z. Physiol. Chem. 1975 356:1613-23). The enzyme from Cryptococcus uniguttulatus Y 0033 has a pH optimum of 6.0-8.0, an optimum temperature of 55° C. and a molecular weight of 110 kDa (U.S. Pat. No. 4,877,733). The enzyme from Pseudomonas sp. FH1227 has a pH optimum of 8.5-9.0, an optimum temperature of 55° C. and a molecular weight of 101 kDa (U.S. Pat. No. 5,298,411).

Commercially applied GDHs are primarily derived from microorganisms. Initially, GDH was produced by fermentation of the natural host organisms such as B. megaterium ATCC39118 (U.S. Pat. No. 4,542,098), Bacillus cereus DSM 1644 (U.S. Pat. No. 4,397,952), Cryptococcus uniguttulatus Y 0033 (U.S. Pat. No. 4,877,733) and Pseudomonas sp. FH1227 (U.S. Pat. No. 5,298,411). Since then, GDH encoding genes have been identified, cloned and expressed in heterologous hosts such as Escherichia coli.

The Bacillus subtilis 61297 GDH gene was expressed in E. coli and exhibited the same physicochemical properties as the enzyme produced in its native host (Vasantha et al. Proc. Natl. Acad. Sci. USA 1983 80:785). The gene sequence of the B. subtilis GDH gene was reported by Lampel, K. A., Uratani, B., Chaudhry, R., Ramaley, R. F., and Rudikoff S., "Characterization of the developmentally regulated Bacillus subtilis glucose dehydrogenase gene," J. Bacteriol. 166, 238-243 (1986) and Yamane, K., Kumano, M. and Kurita, K., "The 25 degrees-36 degrees region of the Bacillus subtilis chromosome: determination of the sequence of a 146 kb segment and identification of 113 genes," Microbiology 142 (Pt 11), 3047-3056 (1996), and is found in Genbank under Accession Nos. M12276 and D50453.

Similarly, gene sequences were determined for GDH from B. cereus ATCC14579 (Nature 2003 423:87-91; Genbank Acc. No. AE017013) and B. megaterium (Eur. J. Biochem. 1988 174:485-490, Genbank Acc. No. X12370; J. Ferment. Bioeng. 1990 70:363-369, Genbank Acc. No. D90044). The GDH enzymes from B. subtilis and B. megaterium are approximately 85% homologous (J. Theor. Biol. 1986 120: 489-497).

It has been well established that GDH enzymes suffer from limited stability. Ramaley and Vasantha reported that presence of glycerol in extraction and purification buffers is absolutely necessary to retain activity for GDH from B. subtilis (J. Biol. Chem. 1983 258:12558-12565). The enzyme instability can be largely attributed to the dissociation of the tetramer into its monomers, which is an equilibrium process that is controlled by environmental factors such as pH and ionic strength (Maurer and Pfleiderer, Z. Naturforsch. 1987 42: 907-915). This has lead to the isolation and studies of GDH from other Bacillus sp. such as B. megaterium. For instance, U.S. Pat. Nos. 5,114,853 and 5,126,256 and Baik et al. Appl. Microbiol. Biotechnol. 2003 61:329-335 describe GDH encoding genes from B. megaterium and mutants thereof that exhibit increased thermostability and that can be produced in recombinant E. coli hosts. However, there remains an industrial need for GDH enzymes that not only have increased thermostability but that also have enhanced enzymatic activity. The above referenced publications and patents, and all other publications and patents referenced herein, are hereby incorporated by reference herein in their entirety.

BRIEF SUMMARY OF THE INVENTION

The present invention has multiple aspects. In one aspect, the present invention is directed to a polypeptide having at least 1.5 times, typically 1.5 to about 25 times, more typically from 1.5 to about 11 times, the GDH activity of the wild-type GDH of SEQ ID NO: 2 (such as determined by the method of Example 4) and being selected from the group consisting of:

(a) a polypeptide having an amino acid sequence which has at least 91% homology, preferably at least 95% homology, and more preferably at least 98% homology with the amino acid sequence of SEQ ID NO: 54, 74, 84, 160, 164 or 168 (hereinafter "homologous polypeptides");

(b) a polypeptide encoded by a nucleic acid sequence which hybridizes under medium stringency conditions with either (i) the nucleotide sequence of SEQ ID NO: 53, 73, 83, 159, 163 or 167; (ii) a subsequence of (i) of at least 100 nucleotides, or (iii) a complementary strand of (i) or (ii) (J. Sambrook, E. F. Fritsch, and T. Maniatis, 1989, Molecular Cloning, A Laboratory Manual, 2d edition, Cold Spring Harbor, N.Y.);

(c) a variant of the polypeptide of SEQ ID NO: 54, 74, 84, 160, 164 or 168 comprising a substitution, deletion, and/or insertion of one to six amino acids;

(d) a fragment of (a), (b) or (c) that has from 1.5 to about 11 times the GDH activity of the wild-type GDH of SEQ ID NO: 2; and (e) a polypeptide of (a), (b) or (c) that retains more than 80% of the initial GDH activity after 20 minutes of incubation at 50° C. and pH 7. In one embodiment, the present invention is also directed to a variant GDH polypeptide as described herein in isolated and purified form. In another embodiment, the present invention is directed to a variant GDH polypeptide as described herein in lyophilized form. In yet another embodiment, the present invention is directed to a composition comprising a variant GDH polypeptide as described herein and a suitable carrier, typically a buffer solution, more typically a buffer solution having a pH between 6.0 and 8.0.

The novel GDH polypeptides of the present invention have enhanced GDH activity (>1.5 fold) relative to the backbone GDH polypeptide from *B. subtilis* of SEQ ID NO: 2 and typically vary from SEQ ID NO: 2 by 1-7 amino acid residues, more typically by 1-6 amino acid residues, even more typically by 1-5 amino acid residues, and most typically by 1-4 amino acid residues. For purposes of the present invention, the degree of homology between two amino acid sequences was determined using the Needleman Wunsch global alignment algorithm, i.e., using dynamic programming algorithm for Global Alignment Scoring Matrix: PAM 120 matrix with gap penalties for introducing gap=−22.183 and extending gap=−1.396. The percent identity=number of identical residues between the first sequence and the second sequence divided by the length of first sequence in alignment (with gaps) (p) indicates partial match. See Needleman, S. B. & Wunsch, C. D., "A general method applicable to the search for similarities in the amino acid sequence of two proteins," Journal of Molecular Biology, 48:443-453 (1970).

The various residue positions of the *B. subtilis* GDH polypeptide that have been substituted to yield enhanced GDH activity and/or thermostability are summarized in Table 1 herein. The amino acid sequences for a number of the inventive GDH polypeptides that have demonstrated enhanced GDH activity and/or thermostability at 50° C. are disclosed herein as SEQ ID NOS: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 and 168. The polynucleotide sequences encoding for the above described inventive GDH polypeptides have SEQ ID NOS: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 75, 77, 83, 85, 87, 89, 91, 93, 95, 97, 99, 99, 101, 103, 105, 107, 109, 11, 113, 115, 117, 119, 121, 123, 125, 127, 129, 131, 133, 135, 137, 139, 141, 143, 145, 147, 149, 151, 153, 155, 157, 159, 161, 163, 165 and 167, respectively.

Another GDH polypeptide (SEQ ID NO: 52) of the present invention, which is encoded by the polynucleotide of SEQ ID NO: 51, is based upon the amino acid sequence of GDH (SEQ ID NO: 4) from *B. megaterium* and differs therefrom by six amino acid residues.

In a preferred embodiment, the present invention is directed to the novel glucose dehydrogenase polypeptides of SEQ ID NOS: 54, 74, 84, 160, 164, and 168 that have enhanced glucose dehydrogenase activity and/or enhanced thermostability relative to the wild-type glucose dehydrogenase of SEQ ID NO: 2.

In yet another embodiment, the present invention is directed to polypeptide having glucose dehydrogenase enzyme activity and being selected from the group consisting of a GDH polypeptide having at least 84% sequence identity with SEQ ID NO: 52, a GDH polypeptide having at least 98% sequence identity with SEQ ID NO: 72, and a GDH polypeptide having at least 98% sequence identity with SEQ ID NO: 58.

In its second aspect, the present invention is directed to a polynucleotide sequence that encodes for the correspondingly referenced GDH polypeptide. Given the degeneracy of the genetic code, the present invention is also directed to any polynucleotide that encodes for the above referenced GDH polypeptides of the present invention. In another preferred embodiment, the present invention is directed to certain specific polynucleotides of SEQ ID NOS: 53, 73, 83, 159, 163, and 167 that encode for the novel glucose dehydrogenase polypeptides of SEQ ID NOS: 54, 74, 84, 160, 164 and 168, respectively.

In a third aspect, the present invention is directed to a nucleic acid construct, a vector, or a host cell comprising a polynucleotide sequence encoding a GDH polypeptide of the present invention operatively linked to a promoter.

In a fourth aspect, the present invention is directed to a method of making a GDH polypeptide of the present invention comprising (a) cultivating a host cell comprising a nucleic acid construct comprising a nucleic acid sequence encoding a GDH polypeptide of the present invention under conditions suitable for production of the polypeptide; and (b) recovering the polypeptide.

BRIEF DESCRIPTION OF SEVERAL VIEWS OF THE DRAWINGS

FIGS. 2A-2B in combination provide a table comparing the % amino acid identity of the GDH polypeptides of the present invention versus the GDH polypeptides of the indicated prior art references. In col. 4 of FIG. 2, the GDH polypeptide of *B. subtilis* (S06-3) has the same amino acid sequence as disclosed in EP 955375 (col. 8). To generate FIGS. 2A-2B, alignments were done using dynamic programming algorithm for Global Alignment Scoring Matrix: PAM 120 matrix with gap penalties for introducing gap=−22.183 and extending gap=−1.396. The percent identity=number of identical residues between the first sequence and the second sequence divided by the length of first sequence in alignment (with gaps) (p) indicates partial match. See Needleman, S. B. & Wunsch, 4C. D., "A general method applicable to the search for similarities in the amino acid sequence of two proteins," Journal of Molecular Biology, 48:443-453 (1970).

Figure 1:
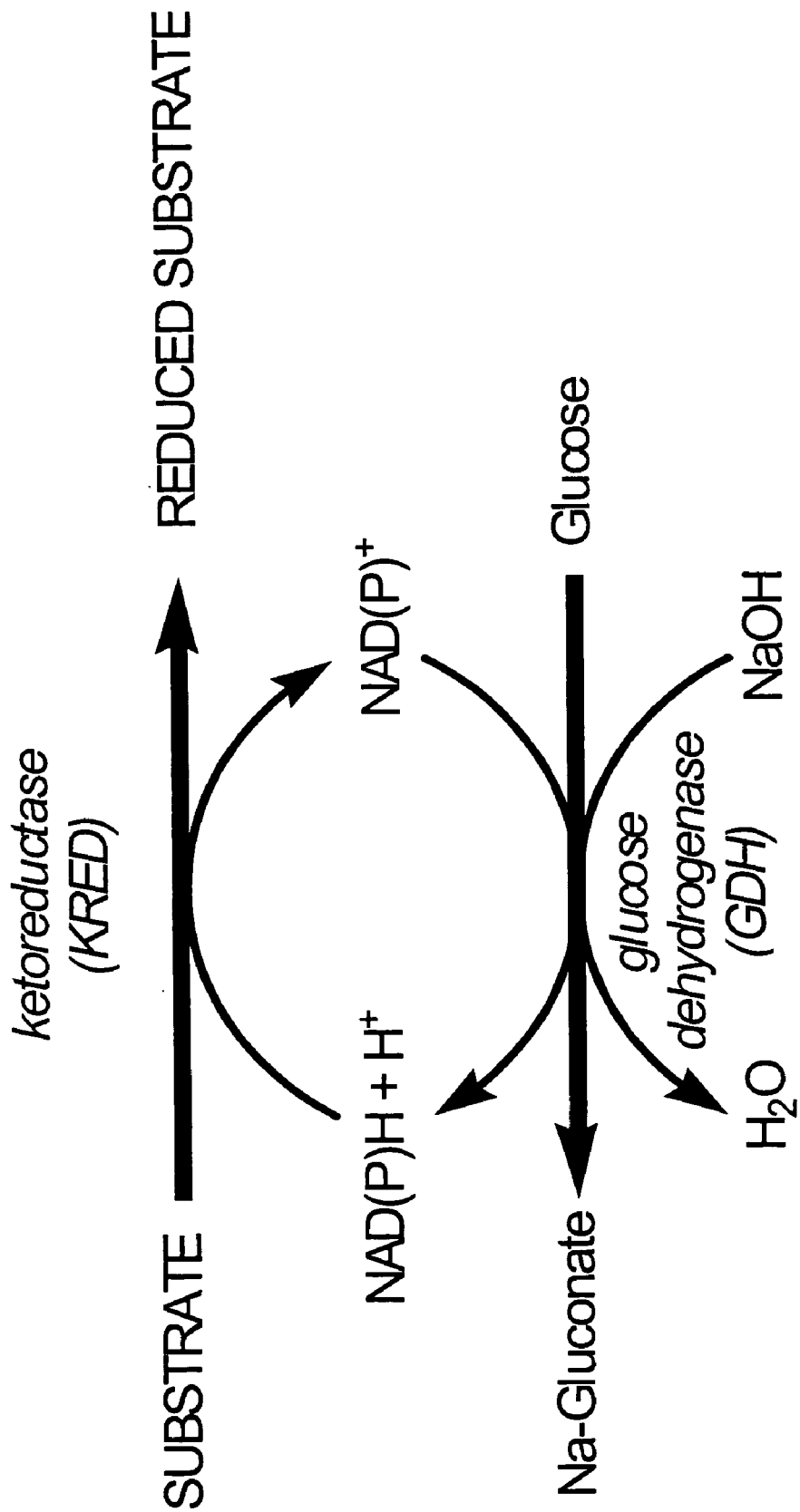
FIG. 1 exemplifies an oxidation-reduction cycle wherein glucose is oxidized by GDH to gluconic acid in the presence of $NAD^+$ (or $NADP^+$) to produce the corresponding reduced form NADH (or NADPH), respectively, which in turn drives the reduction of a substrate to a reduced substrate while being oxidized back to NAD (or NADP) by a reductase. The gluconic acid formed in this reaction is neutralized by sodium hydroxide to sodium-gluconate.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

The present invention has multiple aspects. In one aspect, the present invention is directed to a polypeptide having at least 1.5 times, typically 1.5 to about 25 times, more typically from 1.5 to about 11 times the GDH activity of the wild-type GDH of SEQ ID NO: 2 (such as determined by the method of Example 4) and being selected from the group consisting of:

(a) a polypeptide having an amino acid sequence which has at least 91% homology, preferably at least 95% homology, and more preferably at least 98% homology with the amino acid sequence of SEQ ID NO: 54, 74, 84, 160, 164 or 168 (hereinafter "homologous polypeptides");

(b) a polypeptide encoded by a nucleic acid sequence which hybridizes under medium stringency conditions with either (i) the nucleotide sequence of SEQ ID NO: 53, 73 or 83, (ii) a subsequence of (i) of at least 100 nucleotides, or (iii) a complementary strand of (i) or (ii) (J. Sambrook, E. F. Fritsch, and T. Maniatis, 1989, Molecular Cloning, A Laboratory Manual, 2d edition, Cold Spring Harbor, N.Y.);

(c) a variant of the polypeptide of SEQ ID NO: 54, 74, 84, 160, 164 or 168 comprising a substitution, deletion, and/or insertion of one to six amino acids;

(d) a fragment of (a), (b) or (c) that has from 1.5 to about 11 times the GDH activity of the wild-type GDH of SEQ ID NO: 2; and (e) a polypeptide of (a), (b) or (c) that retains more than 80% of the initial GDH activity after 20 minutes of incubation at 50° C. and pH 7.

Unless otherwise noted, as used throughout this specification, the terms "percent identity," "% identity," "percent identical," and "% identical" are used interchangeably herein to refer to the percent amino acid sequence identity that is determined using the Needleman Wunsch global alignment algorithm, i.e., using dynamic programming algorithm for Global Alignment Scoring Matrix: PAM 120 matrix with gap penalties for introducing gap=−22.183 and extending gap=−1.396. The percent identity=number of identical residues between the first sequence and the second sequence divided by the length of first sequence in alignment (with gaps) (p) indicates partial match. See Needleman, S. B. & Wunsch, C. D., "A general method applicable to the search for similarities in the amino acid sequence of two proteins," Journal of Molecular Biology, 48:443-453 (1970).

As used herein, the terms "glucose dehydrogenase" and "GDH" are used interchangeably herein to refer to a polypeptide that has the ability to catalyze the conversion of glucose and nicotinamide adenine dinucleotide (NAD) to gluconolactone and reduced nicotinamide adenine dinucleotide (NADH). Alternatively, the phosphorylated cofactors NADP and NADPH can replace NAD and NADH in the above reaction. In nature, GDH is made up of four subunits that are loosely held together in a homo-tetramer. Based upon the crystal structure of wild-type *B. megaterium* GDH polypeptide (SEQ ID NO: 4) (Yamamoto et al. J. Biochem. 2001 129:303-312), residue positions 188-217 of the polypeptide define a protein loop region that is involved in $NAD^+$ and glucose binding.

In use, the enhanced GDH polypeptides of the present invention are preferably coupled to a synthetic reaction as a cofactor regeneration system (See FIG. 1) to provide a continuing source of reduced cofactor. As used herein, the term "cofactor" refers to a non-protein compound that operates in combination with an enzyme that catalyzes a reaction of interest. Suitable cofactors employed with the GDH polypeptides of the present invention include NADP (nicotinamide-adenine dinucleotide phosphate) and NAD (nicotinamide adenine dinucleotide).

The term "cofactor regeneration system" refers herein to a set of reactants that participate in a reaction that regenerates a utilized cofactor back to its pre-reaction state. An example is the regeneration of oxidized cofactor regeneration back to reduced cofactor, e.g., NADP to NADPH. The reduced (re-generated) cofactor is then capable of participating in a reaction with a substrate and an enzyme, such as a reducing enzyme, to produce the reduced substrate and the oxidized (utilized) cofactor, which can again be regenerated by the cofactor regeneration system. The above-described operation of the glucose/glucose dehydrogenase cofactor regeneration system is exemplified in FIG. 1.

In FIG. 1, the reaction catalyzed by the reducing enzyme is shown as being coupled to the glucose dehydrogenase cofactor regeneration system. The term "coupled" is used herein to refer to the use of the reduced form of cofactor in the reduction of a substrate, and the concomitant use of the oxidized form of the same cofactor, generated in the aforementioned reaction, in the oxidation of a component (e.g., glucose) of the cofactor regeneration system, which generates the reduced form of the same cofactor. One possible limiting factor in the overall reaction speed in a coupled system is the speed (activity) of the GDH polypeptide in regenerating cofactor.

The GDH polypeptides of the present invention have enhanced GDH activity (such as measured by the method of Example 4) that is 1.5 fold to about 11 fold greater than the GDH activity of the backbone GDH polypeptide from *B. subtilis* of SEQ ID NO: 2, and typically vary from SEQ ID NO: 2 by 1-7 amino acid residues, more typically by 1-6 amino acid residues, even more typically by 1-5 amino acid residues, and most typically by 1-4 amino acid residues. Preferably, the GDH polypeptides of the present invention have enhanced GDH activity that is 2.5 fold to about 11 fold greater than the GDH activity of the backbone GDH polypeptide from *B. subtilis* of SEQ ID NO: 2. More preferably, the GDH polypeptides of the present invention have enhanced thermostability after heat treatment at 50° C. for 20 minutes that is 1.5 fold to about 15 fold greater than the GDH activity of the backbone GDH polypeptide from *B. subtilis* of SEQ ID NO: 2. The thermostability is determined by measuring the residual GDH activity (such as by the method of Example 4) remaining after heat treatment of the GDH polypeptide at 50° C. for 20 minutes.

The amino acid sequences for a number of the inventive GDH polypeptides that have demonstrated enhanced GDH activity and/or thermostability at 50° C. are disclosed herein as SEQ ID NOS: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 and 168. The polynucleotide sequences encoding for the above described inventive GDH polypeptides have SEQ ID NOS: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 75, 77, 83, 85, 87, 89, 91, 93, 95, 97, 99, 99, 101, 103, 105, 107, 109, 11, 113, 115, 117, 119, 121, 123, 125, 127, 129, 131, 133, 135, 137, 139, 141, 143, 145, 147, 149, 151, 153, 155, 157, 159, 161, 163, 165 and 167, respectively.

In yet another aspect, the present invention is directed to GDH polypeptides that have enhanced activity in coupled reactions.

In another embodiment, the present invention is directed to a GDH polypeptide encoded by a nucleic acid sequence which hybridizes under medium stringency conditions with either (i) the nucleotide sequence of SEQ ID NO: 53, 73, 83, 159, 163 or 167 (ii) a subsequence of (i) of at least 100 nucleotides, or (iii) a complementary strand of (i) or (ii) (J. Sambrook, E. F. Fritsch, and T. Maniatis, 1989, Molecular Cloning, A Laboratory Manual, 2d edition, Cold Spring Harbor, N.Y.). For polynucleotides of at least 100 nucleotides in length, low to very high stringency conditions are defined as prehybridization and hybridization at 42° C. in 5×SSPE, 0.3% SDS, 200 mµg/ml sheared and denatured salmon sperm DNA, and either 25% formamide for low stringencies, 35% formamide for medium and medium-high stringencies, or 50% formamide for high and very high stringencies, following standard Southern blotting procedures.

For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

In another embodiment, the present invention is directed to a variant of the polypeptide of SEQ ID NO: 54, 74, 84, 160, 164 or 168 having a substitution, deletion, and/or insertion of one to six amino acids therefrom, and having from 1.5 to about 11 times the GDH activity of the wild-type GDH of SEQ ID NO: 2, such as determined by the method of Example 4. Preferably, amino acid changes are of a minor nature, that is conservative amino acid substitutions that do not significantly affect the folding and/or activity of the protein; small deletions, typically of one to six amino acids; small amino- or carboxyl-terminal extensions; a small linker peptide; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions, which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In another embodiment, the present invention is directed to a fragment of (a), (b) or (c), as described above in the first paragraph of the Detailed Description, that has from 1.5 to about 11 times the GDH activity of the wild-type GDH of SEQ ID NO: 2, such as determined by the method of Example 4. By the term "fragment" is meant that the polypeptide has a deletion of 1 to 10 amino acid residues from the carboxy terminus, the amino terminus, or both. Preferably, the deletion is 1 to 10 residues from the carboxy terminus, more preferably, the deletion is 1 to 5 residues from the carboxy terminus.

In yet another embodiment, the present invention is directed to a GDH polypeptide of (a), (b) or (c), as described above in the first paragraph of the Detailed Description, that retains more than 80% of the initial (pre-incubation) GDH activity after 20 minutes of incubation at 50° C. and pH 7. Preferably, the polypeptides of the invention retain at least 85% of the initial residual activity, more preferably at least 90% residual activity after 20 minutes incubation at 50° C. and pH 7. The initial GDH activity is readily determined by an assay for GDH activity, such as described in Example 4 herein.

Another GDH polypeptide (SEQ ID NO: 52) of the present invention is based upon the amino acid sequence of the GDH polypeptide (SEQ ID NO: 4) from *B. megaterium* and differs therefrom by six amino acid residues. This GDH polypeptide is encoded by the polynucleotide of SEQ ID NO: 51.

In yet another embodiment, the present invention is directed to polypeptide having glucose dehydrogenase enzyme activity and being selected from the group consisting of a GDH polypeptide having at least 84% sequence identity with SEQ ID NO: 52, a GDH polypeptide having at least 98% sequence identity with SEQ ID NO: 72, and a GDH polypeptide having at least 98% sequence identity with SEQ ID NO: 58. These percent identities were obtained by ClustalW analysis (version W 1.8 available form European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty:10; Gap Extension Penalty:0.10; Protein weight matrix: Gonnet series; DNA weight matrix: IUB; Toggle Slow/Fast pairwise alignments=SLOW or FULL Alignment.

Polynucleotides

In its second aspect, the present invention is directed to a polynucleotide sequence that encodes for a GDH polypeptide of the present invention. Given the degeneracy of the genetic code, the present invention is also directed to any polynucleotide that encodes for the above referenced GDH polypeptides of the present invention. In a preferred embodiment, the present invention is directed to certain specific polynucleotides of SEQ ID NOS: 53, 73, 83, 159, 163 and 167 that encode for the novel glucose dehydrogenase polypeptides of SEQ ID NOS: 54, 74, 84, 160, 164 and 168, respectively.

To make the improved GDH polypeptides of the present invention, one starts with one or more wild-type polynucleotides that encode a GDH polypeptide. The term "wild-type" polynucleotide means that the nucleic acid fragment does not comprise any mutations from the form isolated from nature. The term "wild-type" protein means that the protein will be active at a level of activity found in nature and typically will comprise the amino acid sequence as found in nature. Thus, the term "wild type" or "parental sequence" indicates a starting or reference sequence prior to a manipulation of the invention.

Suitable sources of wild-type GDH as a starting material to be improved are readily identified by screening genomic libraries for the GDH activities described herein. See e.g., Example 4. A particularly suitable source of GDH is the *Bacillus* sp. bacteria as found in nature. See Example 1. Using the published glucose dehydrogenase gene sequences for *B. subtilis* (e.g., EP 955375) and *B. megaterium* (e.g., U.S. Pat. No. 5,114,853), primers for amplification of the genes from their respective gene libraries were created using conventional techniques and have the following sequences:

```
B. subtilis forward primer (SEQ ID NO: 79):
5'-GAATTCGCCCATATGTATCCGGATTTAAAAGG-3'

B. subtilis reverse primer (SEQ ID NO: 80):
5'-TGGCCGGATCCTCATTAACCGCGGCCTGGCTGGA-3'

B. megaterium forward primer (SEQ ID NO: 81):
5'-GAATTCGCGCATATGTATAAAGATTTAGAAGG-3'

B. megaterium reverse primer (SEQ ID NO: 82):
5'-GGCCGGATCGTCATTATCCGCGTCCTGCTTTGGA-3'
```

Using a forward and reverse primer pair in a conventional polymerase chain reaction (PCR) to amplify the appropriate portion of the gene from *B. subtilis* and *B. megaterium*, several PCR products were obtained. Each PCR product was cloned into an expression vector and operatively linked behind a lac promoter. Upon screening the clones for GDH activity (e.g., by the assay of Example 4), several clones were found to express active GDH and these genes were sequenced. A first DNA sequence (SEQ ID NO: 1) designated as S06-3 and encoding a GDH polypeptide identical to the published *Bacillus subtilis* GDH (SEQ ID NO: 2) was obtained from *Bacillus subtilis*. A second DNA sequence (SEQ ID NO: 3), designated as M02-6 and encoding a GDH polypeptide that was 98.5% identical to the published *Bacillus megaterium* GDH (SEQ ID NO: 4), was obtained from *Bacillus megaterium*. These DNA sequences were utilized as the starting material for developing the improved polypeptides and polynucleotides of the present invention.

In addition to the PCR primers described above, other PCR primers of different lengths could be used as well. See, e.g., Innis et al., 1990, PCR: A Guide to Methods and Application, Academic Press, New York. Other conventional nucleic acid amplification procedures such as ligase chain reaction (LCR), ligated activated transcription (LAT) and nucleic acid sequence-based amplification (NASBA) could also be used.

Once a suitable starting material has been identified, a non-naturally occurring and mutated and/or evolved enzyme, having unknown glucose dehydrogenase activity is readily generated using any one of the well-known mutagenesis or directed evolution methods. See, e.g., Ling, et al., "Approaches to DNA mutagenesis: an overview," *Anal. Biochem.*, 254(2):157-78 (1997); Dale, et al., "Oligonucleotide-directed random mutagenesis using the phosphorothioate method," *Methods Mol. Biol.*, 57:369-74 (1996); Smith, "In vitro mutagenesis," *Ann. Rev. Genet.*, 19:423-462 (1985); Botstein, et al., "Strategies and applications of in vitro mutagenesis," *Science*, 229:1193-1201 (1985); Carter, "Site-directed mutagenesis," *Biochem. J.*, 237:1-7 (1986); Kramer, et al., "Point Mismatch Repair," *Cell*, 38:879-887 (1984); Wells, et al., "Cassette mutagenesis: an efficient method for generation of multiple mutations at defined sites," *Gene*, 34:315-323 (1985); Minshull, et al., "Protein evolution by molecular breeding," *Current Opinion in Chemical Biology*, 3:284-290 (1999); Christians, et al., "Directed evolution of thymidine kinase for AZT phosphorylation using DNA family shuffling," *Nature Biotechnology*, 17:259-264 (1999); Crameri, et al., "DNA shuffling of a family of genes from diverse species accelerates directed evolution," *Nature*, 391: 288-291; Crameri, et al., "Molecular evolution of an arsenate detoxification pathway by DNA shuffling," *Nature Biotechnology*, 15:436-438 (1997); Zhang, et al., "Directed evolution of an effective fucosidase from a galactosidase by DNA shuffling and screening," *Proceedings of the National Academy of Sciences U.S.A.*, 94:45-4-4509; Crameri, et al., "Improved green fluorescent protein by molecular evolution using DNA shuffling," *Nature Biotechnology* 14:315-319 (1996); Stemmer, "Rapid evolution of a protein in vitro by DNA shuffling," *Nature*, 370:389-391 (1994); Stemmer, "DNA shuffling by random fragmentation and reassembly: In vitro recombination for molecular evolution," *Proceedings of the National Academy of Sciences, U.S.A.*, 91:10747-10751 (1994); WO 95/22625; WO 97/0078; WO 97/35966; WO 98/27230; WO 00/42651; WO 01/75767 and U.S. Pat. No. 6,537,746 which issued to Arnold, et al. on Mar. 25, 2003 and is entitled "Method for creating polynucleotide and polypeptide sequences."

Any of these methods can be applied to generate GDH polynucleotides. To maximize any diversity, several of the above-described techniques can be used sequentially. Typically, a library of variant polynucleotides is created by one mutagenic or evolutionary technique and their expression products are screened to find the polypeptides having the highest GDH activity. Then, a second mutagenic or evolutionary technique is applied to polynucleotides encoding the most active polypeptides to create a second library, which in turn is screened for GDH activity by the same technique. The process of mutating and screening can be repeated as many times as needed, including the insertion of point mutations, to arrive at a polynucleotide that encodes a polypeptide with the desired activity, thermostability, and cofactor preference.

Alternatively, polynucleotides and oligonucleotides of the invention can be prepared by standard solid-phase methods, according to known synthetic methods. Typically, fragments of up to about 100 bases are individually synthesized, then joined (e.g., by enzymatic or chemical litigation methods, or polymerase mediated methods) to form essentially any desired continuous sequence. For example, polynucleotides and oligonucleotides of the invention can be prepared by chemical synthesis using, e.g., the classical phosphoramidite method described by Beaucage et al. (1981) *Tetrahedron Letters* 22:1859-69, or the method described by Matthes et al. (1984) *EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company, Midland, Tex., The Great American Gene Company (Ramona, Calif.), Express-Gen Inc., Chicago, Ill., Operon Technologies Inc. (Alameda, Calif.), and many others. Similarly, peptides and antibodies can be custom ordered from any of a variety of sources, such as PeptidoGenic (pkim@ccnet.com), HTI Bio-products, Inc. (http://www.htibio.com), BMA Biomedicals Ltd. (U.K.), Bio.Synthesis, Inc., and many others.

Polynucleotides may also be synthesized by well-known techniques as described in the technical literature. See, e.g., Carruthers et al., *Cold Spring Harbor Symp. Quant. Biol.*

47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

General texts which describe molecular biological techniques useful herein, including mutagenesis, include Berger and Kimmel, *Guide to Molecular Cloning Techniques Methods in Enzymology*, volume 152 Academic Press, Inc., San Diego, Calif. ("Berger"); Sambrook et al., *Molecular Cloning—A Laboratory Manual* (2nd Ed.), volumes 1-3, Cold Spring Harbor Laboratory, Cold Spring Harbor, N.Y., 1989 ("Sambrook"); and *Current Protocols in Molecular Biology*, F. M. Ausubel et al., eds., Current Protocols, a joint venture between Greene Publishing Associates, Inc. and John Wiley & Sons, Inc. (supplemented through 2000) ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guided to Methods and Applications* (Innis et al., eds.) Academic Press Inc. San Diego, Calif. (1990); Arnheim & Levinson (Oct. 1, 1990) *Chemical and Engineering News* 36-47; *The Journal Of NIH Research* (1991) 3:81-94; Kwoh et al. (1989) *Proc. Natl. Acad. Sci. USA* 86:1173; Guatelli et al. (1990) *Proc. Natl. Acad. Sci. USA* 87:1874; Lomeli et al. (1989) *J. Clin. Chem.* 35:1826; Landegren et al., (1988) *Science* 241:1077-1080; Van Brunt (1990) *Biotechnology* 8:291-294; Wu and Wallace, (1989) *Gene* 4:560; Barringer et al. (1990) *Gene* 89:117, and Sooknanan and Malek (1995) *Biotechnology* 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369:684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

It will be appreciated by those skilled in the art due to the degeneracy of the genetic code, a multitude of nucleotide sequences encoding GDH polypeptides of the invention may be produced, some of which bear substantial identity to the nucleic acid sequences explicitly disclosed herein.

In the present case, several round No. 1 libraries were created by applying a variety of mutagenic techniques to the coding region of the *B. subtilis* gdh gene (SEQ ID NO: 1) or to the coding region of the *B. megaterium* gdh gene (SEQ ID NO: 3), as obtained by PCR.

To obtain expression of the variant gene encoding a GDH, the variant gene was first operatively linked to one or more heterologous regulatory sequences that control gene expression to create a nucleic acid construct, such as an expression vector or expression cassette. Thereafter, the resulting nucleic acid construct, such as an expression vector or expression cassette, was inserted into an appropriate host cell for ultimate expression of the GDH polypeptide encoded by the shuffled gene. A "nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. Thus, in one aspect, the present invention is directed to a nucleic acid construct comprising a polynucleotide encoding a GDH polypeptide of the present invention.

The term "nucleic acid construct" is synonymous with the term "expression cassette" when the nucleic acid construct contains all the control sequences required for expression of a coding sequence of the present invention. The term "coding sequence" is defined herein as a nucleic acid sequence, which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated polynucleotide encoding a GDH polypeptide of the present invention may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

The term "control sequence" is defined herein to include all components, which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence. The "promoter sequence" is a relatively short nucleic acid sequence that is recognized by a host cell for expression of the longer coding region that follows. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

For bacterial host cells, suitable promoters for directing the transcription of the nucleic acid constructs of the present invention, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, Proceedings of the National Academy of Sciences USA 75: 3727-3731), as well as the tac promoter (De- Boer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

For filamentous fungal host cells, suitable promoters for directing the transcription of the nucleic acid constructs of the present invention include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator, which is functional in the host cell of choice, may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosph-ate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention. Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence that is functional in the host cell of choice may be used in the present invention. Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region that directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothernophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora* thermophile lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the GDH polypeptide of the present invention would be operably linked with the regulatory sequence.

Expression Vectors

In another aspect, the present invention is also directed to a recombinant expression vector comprising a polynucleotide of the present invention (which encodes a GDH polypeptide of the present invention), and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A, the origins of replication of plasmids pBR322, pUC19, pACYC177, which has the P15A origin of replication), or pACYC184 which permit replication in *E. coli*; and pUB110, pE194, pTA1060, or pAMβ1 which permit replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proceedings of the National Academy of Sciences USA 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant nucleic acid construct and expression vectors of the present invention are well known to one skilled in the art (see, e.g., J. Sambrook, E. F. Fritsch, and T. Maniatis, 1989, Molecular Cloning, A Laboratory Manual, 2d edition, Cold Spring Harbor, N.Y.).

Many of the expression vectors for use in the present invention are commercially available. Suitable commercial expression vectors include p3xFLAG™ expression vectors from Sigma-Aldrich® Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII® SK(-) and pBK-CMV, which are commercially available from Stratagene, LaJolla Calif., and plasmids that are derived from pBR322 (Gibco BRL®), pUC (Gibco BRL®), pREP4, pCEP4 (Invitrogene®) or pPoly (Lathe et al., 1987, Gene 57, 193-201).

Host Cells

Host cells for use in expressing the expression vectors of the present invention include but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are well known in the art.

By way of example, *Escherichia coli* W3110 was transformed by an expression vector for expressing the shuffled genes of the present invention. The expression vector was created by operatively linking a variant gene of the present invention to the lac promoter under control of the laI repressor gene. The expression vector also contained the P15A origin of replication and the chloroamphenicol resistance gene. The transformed *Escherichia coli* W3110 was cultured under appropriate culture medium containing chloroamphenicol such that only transformed *E. coli* cells that expressed the expression vector survived. See e.g., Example 1.

Purification

Once the GDH polypeptides were expressed by the variant genes in *E. coli*, the polypeptides are purified from the cells and or the culture medium using any one or more of the well known techniques for protein purification, including lysozyme treatment, sonication, filtration, salting, ultra-centrifugation, affinity chromatography, and the like. Suitable solutions for high efficiency extraction of proteins from bacteria, such as *E. coli*, are commercially available under the trade name CelLytic B®from Sigma-Aldrich® of St. Louis Mo. A suitable process for purifying GDH polypeptides sufficiently from cell lysate for applications in a chemical process is disclosed in Example 3 herein.

Screening

Screening clones of the GDH polypeptides from the expression libraries for enhanced GDH activity is typically performed using the standard biochemistry technique of monitoring the rate of formation of NADH or NADPH, via an increase in absorbance or fluorescence. Such a procedure is described in Example 4 herein.

After screening the libraries after the first round of mutations, an improved GDH polypeptide, which had the mutation I165T relative to the *B. subtilis* GDH backbone of SEQ ID NO: 2, provided a 2.6 fold increase in initial GDH activity relative to the wild-type *B. subtilis* GDH (SEQ ID NO: 2). Thereafter, additional rounds of directed evolution were performed and the resulting exemplary GDH polypeptides of the present invention are listed in Table 1 below along with their mutations and activity relative to the wild-type (w-t) *B. subtilis* GDH backbone of SEQ ID NO: 2:

TABLE 1

| GDH Peptide No. | Mutations | X-fold Initial GDH Activity over w-t GDH from *B. subtilis* | Increased Thermostability @ 50° C., 20 min |
|---|---|---|---|
| SEQ ID NO: 84 | I165M, V209A, I242V | *** | No |
| SEQ ID NO: 52 | V209A | * | No |
| SEQ ID NO: 54 | I165M, P194T | ** | Yes |
| SEQ ID NO: 56 | I165T | ** | Yes |
| SEQ ID NO: 64 | I165M, V209A, I242V, Q252L | ** | Yes |
| SEQ ID NO: 74 | I165L | ** | Yes |
| SEQ ID NO: 160 | I165M, P194T, A197K, K204E, K206R | *** | Yes |
| SEQ ID NO: 164 | I165M, E170K, P194T, A197K, K204E, K206R, E222D, S237C | *** | Yes |
| SEQ ID NO: 168 | A16T, I165M, P194T, A197K, K204E, K206R | *** | Yes |

* 1.5-2.4 fold increase
** 2.5-3.4 fold increase
*** 3.5-5.5 fold increase

Comparing the GDH polypeptides of SEQ ID NOS: 64 and 84 in Table 1 above, it is seen that the Q252L mutation conferred heat stability on the GDH polypeptide, while reducing some initial GDH activity.

The GDH polypeptide of SEQ ID NO: 74, which has the single change I165L relative to the *B. subtilis* GDH backbone of SEQ ID NO: 2, provides a 5 fold increase in initial GDH activity, and a 13 fold increase in activity in a coupled chemistry process relative to the wild-type *B. subtilis* GDH (SEQ ID NO: 2).

More preferred GDH polypeptides of the present invention are those polypeptides having 95% homology, more preferably 97% homology, and even more preferred 100% homology with the polypeptides of SEQ ID NOs: 160, 164 and 168. As shown above, each of these polypeptides has from 5-8 mutations but has the following five mutations in common: I165M, P194T, A197K, K204E and K206R. Thus, stated in other terms, one embodiment of the present invention is directed to a GDH polypeptide of SEQ ID NO: 2 having from 5-8 residue substitutions wherein five of the residue substitution are I165M, P194T, A197K, K204E, and K206R.

Only a very few (≦0.5%) of the mutations to the wild-type *B. subtilis* GDH (SEQ ID NO: 2) backbone were found to be beneficial. Specifically, for every 1000 clones screened, there occurred only 3-5 single point or double point mutations that were beneficial. In fact, many of the mutations were found to be detrimental. For example, Y253C rendered the GDH polypeptide inactive, whereas Q252L slightly reduced the initial GDH activity wild-type *B. subtilis* GDH (SEQ ID NO: 2). Interestingly, the beneficial effects of one mutation were not found to be additive with the beneficial effects of another mutation. Thus, for example, it was discovered that the combination of a first mutation that increased GDH activity 2 fold compared to the wild-type activity, with a second mutation at a second residue position that increased GDH activity 3 fold compared to the wild-type activity most often did not result in a GDH polypeptide that had a 5 or 6 fold increase in GDH activity.

The GDH polypeptides of the present invention have the activities described herein, as well as other desirable properties, e.g., altered temperature and/or pH optimums, solvent resistance (e.g., butyl acetate), and the like. Moreover, the GDH polynucleotide may be mutated or evolved to generate libraries that can be screened to identify those modified GDH polypeptides having the ability to preferentially accept other compounds as cofactors, such as, for example, NADP (also referred to as NADP$^+$).

The polynucleotides encoding the GDH polypeptides of the present invention may be codon optimized for optimal production from the host organism selected for expression. Those having ordinary skill in the art will recognize that tables and other references providing codon preference information for a wide range of organisms are readily available. See e.g., Henaut and Danchin, "*Escherichia coli* and *Salmonella*," Neidhardt, et al. Eds., ASM Press, Washington D.C., p. 2047-2066 (1996).

Screening for transformed cells that express GDH is, in general, a two-step process. First, one physically separates the cells and then determines which cells do and do not possess a desired property. Selection is a form of screening in which identification and physical separation are achieved simultaneously by expression of a selection marker, which, in some genetic circumstances, allows cells expressing the marker to survive while other cells die (or vice versa). Exemplary screening markers include luciferase, β-galactosidase, and green fluorescent protein. Selection markers include drug and toxin resistance genes, such as resistance to chloramphenicol, ampicillin and the like. Although spontaneous selection can and does occur in the course of natural evolution, in the present methods selection is performed by man.

The GDH polynucleotides generated by the mutagenesis or directed evolution method are screened in accordance with the protocol described in Example 4 to identify those having enhanced activity that are suitable for inclusion as an improved GDH polypeptide of the present invention.

The following sequence summarizes the diversity of the GDH polypeptides of the present invention relative to the wild type *B. subtilis* GDH polypeptide of SEQ ID NO: 2, as also disclosed in EP 955375, wherein one or more of the amino acid residues designated as "X" followed by the residue number are replaced to the GDH polypeptides of the present invention:

The diversity of changes at various residue positions for the GDH polypeptides of the present invention are shown to the right of the arrow in Table 2 below and relative amino acid residues of wild-type GDH of SEQ ID NO: 2 (EP 055375) which are shown to the left of the arrow:

TABLE 2

| | |
|---|---|
| $X_{11}$: | A → D |
| $X_{16}$: | A → T |
| $X_{46}$: | N → D |
| $X_{47}$: | E → D, K |
| $X_{54}$: | K → R |
| $X_{63}$: | Q → R |
| $X_{68}$: | K → N |
| $X_{75}$: | I → V |
| $X_{92}$: | N → S |
| $X_{95}$: | L → F |
| $X_{96}$: | E → A |
| $X_{114}$: | G → S |
| $X_{165}$: | I → M, L, V, T |
| $X_{170}$: | E → K |
| $X_{178}$: | P → Q |
| $X_{194}$: | P → T |
| $X_{197}$: | A → K |
| $X_{198}$: | E → A, D, G, K, L |
| $X_{200}$: | F → M, Y |
| $X_{201}$: | A → G, L, S, T |
| $X_{202}$: | D → N |
| $X_{203}$: | P → D, N, R, S |
| $X_{204}$: | K → D, E, L, N, T, Q |
| $X_{205}$: | Q → N |
| $X_{206}$: | K → R |
| $X_{209}$: | V → A |
| $X_{210}$: | E → A, K |
| $X_{211}$: | S → G, T |
| $X_{212}$: | M → K |
| $X_{216}$: | G → L |
| $X_{219}$: | G → A |
| $X_{220}$: | E → Q |
| $X_{222}$: | E → D |
| $X_{234}$: | K → E, S |
| $X_{237}$: | S → C |
| $X_{242}$: | I → V |
| $X_{252}$: | Q → L |
| $X_{253}$: | Y → C |

EXAMPLE 1

Construction of Expression Constructs for Expression of Glucose Dehydrogenase

The genes for the glucose dehydrogenase were amplified using the polymerase chain reaction (PCR) from genomic DNA preparations of *Bacillus subtilis* and *Bacillus megaterium*. The primers for the amplification reactions were (SEQ ID NO: 169)
M Y P D L K G K V V $X_{11}$ I T G A $X_{16}$ S G L G K A M A I R F G K E Q A K V V I N Y Y S N K Q D P $X_{46}$ $X_{47}$ V K E E V I $X_{54}$ A G G E A V V V $X_{63}$ G D V T $X_{68}$ E E D V K N $X_{75}$ V Q T A I K E F G T L D I M I N $X_{92}$ A G $X_{95}$ $X_{96}$ N P V P S H E M P L K D W D K V I $X_{114}$ T N L T G A F L G S R E A I K Y F V E N D I K G N V I N M S S V H E V I P W P L F V H Y A A S K G G $X_{165}$ K L M T $X_{170}$ T L A L E Y A $X_{178}$ K G I R V N N I G P G A I N T $X_{194}$ I N $X_{197}$ $X_{198}$ K $X_{200}$ $X_{201}$ $X_{202}$ $X_{203}$ $X_{204}$ $X_{205}$ $X_{206}$ A D $X_{209}$ $X_{210}$ $X_{211}$ $X_{212}$ I P M $X_{216}$ Y I $X_{219}$ $X_{220}$ P $X_{222}$ E I A A V A A W L A S $X_{234}$ E A $X_{237}$ Y V T G $X_{242}$ T L F A D G G M T $X_{252}$ $X_{253}$ P S F Q A G R G.

designed using the published *B. subtilis* and *B. megaterium* glucose dehydrogenase gene sequences, and were as follows:

```
B. subtilis forward primer (SEQ ID NO: 79):
5'-GAATTCGCCCATATGTATCCGGATTTAAAAGG-3'

B. subtilis reverse primer (SEQ ID NO: 80):
5'-TGGCCGGATCCTCATTAACCGCGGCCTGCCTGGA-3'

B. megaterium forward primer (SEQ ID NO: 81):
5'-GAATTCGCCCATATGTATAAAGATTTAGAAGG-3'

B. megaterium reverse primer (SEQ ID NO: 82):
5'-GGCCGGATCCTCATTATCCGCGTCCTGCTTGGA-3'
```

Figure 3:
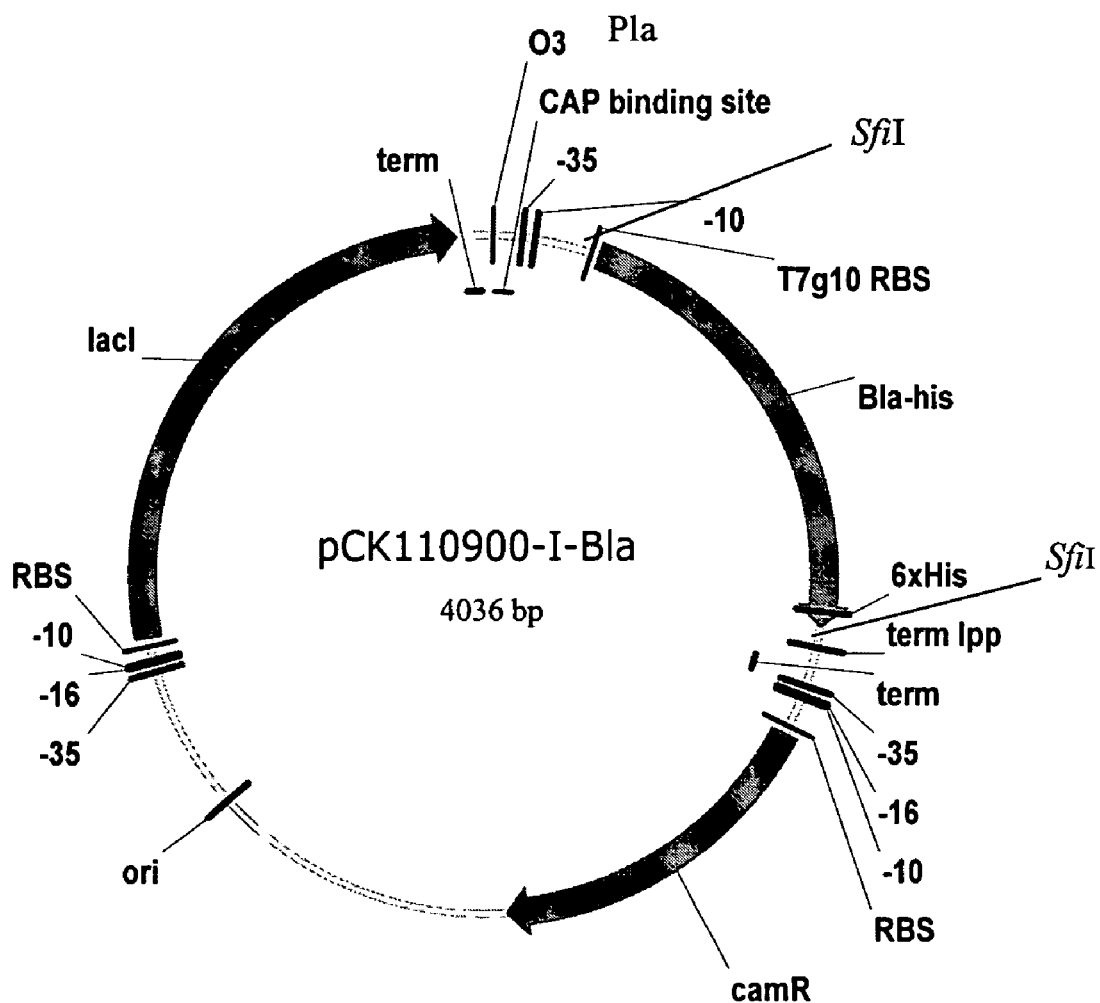
FIG. 3 is a 4036 by expression vector (pCK110900) of the present invention comprising a P15A origin of replication (P15A ori), a lad repressor, a CAP binding site, a lac promoter (lac), a T7 ribosomal binding site (T7g10 RBS), and a chloramphenicol resistance gene (camR).

The PCR products were cloned into an expression vector of FIG. 3 behind a lac promoter under control of the lad repressor gene, creating plasmids pGDHS06 or pGDHM02. The expression vector contained the P15A origin of replication (P15A ori) and the chloramphenicol resistances gene (camR). Several clones were found to express active GDH and these genes were sequenced to confirm their sequences (see SEQ ID NOS: 1 (Glucose dehydrogenase S06-3) and 3 (Glucose dehydrogenase M02-6)).

EXAMPLE 2

Production of GDH

In an aerated agitated fermentor, 10.0 L of growth medium containing 0.528 g/L ammonium sulphate, 7.5 g/L of dipotassium hydrogen phosphate trihydrate, 3.7 g/L of potassium dihydrogen phosphate, 2 g/L of Tastone-154 yeast extract, 0.05 g/L ferrous sulphate, and 3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L sodium borate decahydrate and 0.5 g/L EDTA, was brought to a temperature of 30° C.

The fermentor was inoculated with a late exponential culture of *Escherichia coli* W3110 (pGDHS06 or pGDHM12) grown in a shake flask containing LB, 1% glucose (Sigma Chemical Co., St. Louis, Mo.), and 30 µg/ml chloramphenicol (Sigma Chemical Co., St. Louis, Mo.) to a starting optical density at 600 nm ($OD_{600}$) of 0.5 to 2.0. The fermentor was agitated at 500-1500 rpm and air was supplied to the fermentation vessel at 1.0-15.0 L/min, and the pH of the culture was controlled at 7.0 by addition of 20% v/v ammonium hydroxide. After the culture reached an $OD_{600}$ of 40, the temperature was reduced to 25° C. and the expression of glucose dehydrogenase was induced by the addition of isopropyl-β-D-thiogalactoside (IPTG) (Sigma Chemical Corp., St. Louis, Mo.) to a final concentration of 1 mM. The culture was grown for another 15 hours. After the induction, the cells were harvested by centrifugation and washed with 10 mM potassium phosphate buffer, pH 7.0. The cell paste was used directly in the downstream recovery process or was stored at −80° C. until use.

EXAMPLE 3

GDH Enzyme Preparation

The cell paste was washed by suspending 1 volume wet weight of cell paste in 3 volumes of 100 mM Tris/sulfate (pH 7.2) followed by centrifugation at 5000 g for 40 minutes in a Sorval 12 BP. The washed cell paste was suspended in 2 volumes of 100 mM Tris/sulfate (pH 7.2). The intracellular GDH was released from the cells by passing the suspension through a homogenizer in two passes using a pressure of 14,000 psig for the first pass and 8,000 psig for the second pass. The homogenate was centrifuged at 10,000 rpm in a Beckman lab centrifuge for 60 minutes. The supernatant was decanted and dispensed in shallow containers, frozen at −20° C. and lyophilized.

EXAMPLE 4

GDH Enzyme Activity Assay

Cells were grown overnight at 30 C in 2×YT with 0.5% glucose and 30 ug/ml chloramphenicol. This culture was then diluted 20-fold into fresh LB containing 30 ug/ml chloramphenicol and after 2 hours of growth at 37° C., 1 mM IPTG (isopropyl thiogalactoside) was added. The culture (0.3 ml) was allowed to grow another 4-5 hours at 37° C.

Lysis buffer contains 100 mM triethanolamine buffer (pH 7.0), 2 mg/ml PMBS (polymixin B sulfate), 1 mg/ml lysozyme, 1 mM PMSF (phenyl methyl sulfonyl fluoride).

Cells were pelleted via centrifugation and lysed in 0.2 ml lysis buffer by shaking at room temperature for 1.5 hours.

An aqueous assay mix was made that was 100 mM triethanolamine buffer (pH 7.0), 0.1 to 0.2 mM NADPH or NADH, and 100 mM glucose. A solvent mixture consisting of 1 part ethyl-4-chloro-acetoacetate (ECAA) and 2 parts butyl acetate was added to the assay mixture to form a reaction mixture. The ratio of solvent mixture to assay mixture was 1:2, respectively. To test thermostability, the undiluted lysate was heated at 50° C. and then added to the reaction mixture. The reaction was initiated by adding the diluted glucose dehydrogenate enzyme as a predissolved solution in 100 mM triethanolamine buffer (pH 7.0). The course of reaction was followed by measurement of the increase of absorbance at 340 nm or by the fluorescent emission of light at 440 nm as a function of time. The results were plotted as Absorbance units or relative fluorescent units (RFU) (NADPH or NADH) vs. time, and the slope of the plot determined (Absorbance units/min or RFU/min).

EXAMPLE 5

KRED/GDH Coupled Chemistry Assay

To a 100 mL vessel equipped with a pH electrode-controlled automatic titrator was charged a solution of glucose (7.5 g) in 100 mM triethanolamine pH 7 buffer (25 mL). To this solution were charged the two enzymes (100 mg KRED; 50 mg GDH) and NADP (6.25 mg). ("KRED" is ketoreductase or carbonyl reductase class (EC1.1.1.184) and is useful for the synthesis of optically active alcohols from the corresponding prochiral ketone substrate. Butyl acetate (10 ml) was then charged. Finally, ethyl 4-chloroacetoacetate (6 g) in butyl acetate (10 mL) was charged to the vessel. 4M NaOH is added dropwise on demand by the automatic titrator (a pH of 6.85 was set as a lower limit) to constantly adjust the pH to 7.0. The reaction was complete when no more caustic was needed. The reaction rates were determined by measuring the amount of base added per unit time or by taking samples of the reaction mixture, extracting the sample 3 times with an equal volume of ethyl acetate, and analyzing the combined organic layers by gas chromatography to determine the amount of ethyl-S-4-chloro-3-hydroxybutyrate produced per unit time.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A non-naturally occurring polypeptide capable of converting glucose and nicotinamide adenine dinucleotide (NAD) or nicotinamide adenine dinucleotide phosphate (NADP) to gluconolactone and reduced NADH or reduced NADPH with at least 1.5 times the initial glucose dehydrogenase (GDH) activity of the wild-type GDH of SEQ ID NO: 2 and which comprises an amino acid sequence that is at least 95% identical to SEQ ID NO:54 and has at least one amino acid substitution at residue position 165, 194 or 204 relative to SEQ ID NO:2.

2. The non-naturally occurring polypeptide of claim 1, wherein the polypeptide comprises an amino acid sequence that is at least 98% identical to SEQ ID NO:54.

3. The non-naturally occurring polypeptide of claim 1, wherein the amino acid sequence comprises methionine, leucine, valine, or threonine at residue position 165.

4. The non-naturally occurring polypeptide of claim 1, wherein the amino acid sequence comprises leucine at residue position 165.

5. The non-naturally occurring polypeptide of claim 1, wherein the amino acid sequence comprises threonine at residue position 165.

6. The non-naturally occurring polypeptide of claim 1, wherein the amino acid sequence comprises threonine at residue position 194.

7. The non-naturally occurring polypeptide of claim 1, wherein the amino acid sequence comprises glutamic acid at residue position 204.

8. The non-naturally occurring polypeptide of claim 1, wherein the amino acid sequence comprises methionine at residue position 165 and threonine at residue position 194.

9. The non-naturally occurring polypeptide of claim 1 or 8, wherein the amino acid sequence further comprises an amino acid substitution at residue position 252.

10. The non-naturally occurring polypeptide of claim 9, wherein the amino acid sequence comprises leucine at residue position 252.

11. The non-naturally occurring polypeptide of claim 1, wherein the amino acid sequence comprises methionine at residue position 165, threonine at residue position 194, lysine at residue position 197, glutamic acid at residue position 204, and arginine at residue position 206.

12. The non-naturally occurring polypeptide of claim 1, wherein the polypeptide further comprises a substitution, deletion, and/or insertion of one to six amino acids with respect to SEQ ID NO: 54, 74, 84, 160, 164, or 168.

13. The non-naturally occurring polypeptide of claim 1, wherein the polypeptide comprises the amino acid sequence of SEQ ID NO: 54, 68, 76, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

14. The non-naturally occurring polypeptide of claim 1, wherein the polypeptide comprises the amino acid sequence of SEQ ID NO: 54, 58, 72, 74, or 84.

15. The non-naturally occurring polypeptide of claim 1 which retains more than 80% of the initial GDH activity after 20 minutes of incubation at 50° C. and pH 7.

16. The non-naturally occurring polypeptide of claim 1, which is capable of converting glucose and nicotinamide adenine dinucleotide (NAD) or nicotinamide adenine dinucleotide phosphate (NADP) to gluconolactone and reduced NADH or reduced NADPH with at least 2.5 times the glucose dehydrogenase (GDH) of the wild-type GDH of SEQ ID NO:2, and wherein the amino acid sequence comprises SEQ ID NO: 54, 56, 64, or 74.

17. The non-naturally occurring polypeptide of claim 1, which is capable of converting glucose and nicotinamide adenine dinucleotide (NAD) or nicotinamide adenine dinucleotide phosphate (NADP) to gluconolactone and reduced NADH or reduced NADPH with at least 3.5 times the glucose dehydrogenase (GDH) activity of the wild-type GDH of SEQ ID NO: 2, and wherein the amino acid sequence comprises SEQ ID NO: 84, 160, 164, or 168.

18. The non-naturally occurring polypeptide of claim 1, which is isolated.

19. The non-naturally occurring polypeptide of claim 1, which is in lyophilized form.

20. A composition comprising the non-naturally occurring polypeptide of claim 1 and a suitable carrier.

21. A fragment of a non-naturally occurring polypeptide of claim 1 which is capable of converting glucose and nicotinamide adenine dinucleotide (NAD) or nicotinamide adenine dinucleotide phosphate (NADP) to gluconolactone and reduced NADH or reduced NADPH with at least from 1.5 to about 11 times the GDH activity of the wild-type GDH of SEQ ID NO:2.

22. The polypeptide fragment of claim 21, comprising a fragment of SEQ ID NO: 54, 58, 72, 74, or 84.

23. The polypeptide fragment of claim 21, comprising a fragment of SEQ ID NO: 54, 68, 76, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

* * * * *

SEQUENCE LISTING

```
<160> NUMBER OF SEQ ID NOS: 169

<210> SEQ ID NO 1
<211> LENGTH: 786
<212> TYPE: DNA
<213> ORGANISM: Bacillus subtilis
<220> FEATURE:
<221> NAME/KEY: misc_feature
<223> OTHER INFORMATION: based upon B. subtilis GDH backbone  (S06-3orf)
<220> FEATURE:
<221> NAME/KEY: CDS
<222> LOCATION: (1)..(786)

<400> SEQUENCE: 1 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggc ctc gga aag gcg atg gcc att cgc ttc ggc aag gag cag gca        96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
                100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
        130                 135                 140 agt gtg cac gaa gtg att cct tgg ccg tta ttt gtc cac tat gcg gca       480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac       528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat       624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
    210                 215                 220
```

```
gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa                                             786
Gln Ala Gly Arg Gly
        260
```

<210> SEQ ID NO 2
<211> LENGTH: 261
<212> TYPE: PRT
<213> ORGANISM: Bacillus subtilis

<400> SEQUENCE: 2

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 3
<211> LENGTH: 786
<212> TYPE: DNA
<213> ORGANISM: Bacillus megaterium
<220> FEATURE:
<221> NAME/KEY: misc_feature
<223> OTHER INFORMATION: (M02-6orf)

<220> FEATURE:
<221> NAME/KEY: CDS
<222> LOCATION: (1)..(786)

<400> SEQUENCE: 3

| | | | | | | | | | | | | | | | | |
|---|---|---|---|---|---|---|---|---|---|---|---|---|---|---|---|---|
| atg | tat | aaa | gat | tta | gaa | gga | aaa | gta | gtt | gtc | ata | aca | ggt | tca | tct | 48 |
| Met | Tyr | Lys | Asp | Leu | Glu | Gly | Lys | Val | Val | Val | Ile | Thr | Gly | Ser | Ser | |
| 1 | | | | 5 | | | | | 10 | | | | | 15 | | |
| acc | ggt | tta | gga | aaa | gca | atg | gcg | att | cgt | ttt | gcg | aca | gaa | aaa | gct | 96 |
| Thr | Gly | Leu | Gly | Lys | Ala | Met | Ala | Ile | Arg | Phe | Ala | Thr | Glu | Lys | Ala | |
| | | | 20 | | | | | 25 | | | | | 30 | | | |
| aaa | gta | gtt | gtg | aat | tat | cgt | tcg | aaa | gaa | gaa | gaa | gct | aac | agc | gtt | 144 |
| Lys | Val | Val | Val | Asn | Tyr | Arg | Ser | Lys | Glu | Glu | Glu | Ala | Asn | Ser | Val | |
| | | | | 35 | | | | | 40 | | | | | 45 | | |
| tta | gaa | gaa | att | aaa | aaa | gtc | ggc | gga | gag | gca | att | gcg | gtt | aaa | ggt | 192 |
| Leu | Glu | Glu | Ile | Lys | Lys | Val | Gly | Gly | Glu | Ala | Ile | Ala | Val | Lys | Gly | |
| | 50 | | | | | 55 | | | | | 60 | | | | | |
| gac | gta | aca | gtt | gag | tct | gac | gtg | atc | aat | tta | gtt | caa | tct | gct | att | 240 |
| Asp | Val | Thr | Val | Glu | Ser | Asp | Val | Ile | Asn | Leu | Val | Gln | Ser | Ala | Ile | |
| 65 | | | | | 70 | | | | | 75 | | | | | 80 | |
| aaa | gaa | ttt | gga | aag | tta | gat | gtt | atg | att | aat | aac | gca | gga | atg | gaa | 288 |
| Lys | Glu | Phe | Gly | Lys | Leu | Asp | Val | Met | Ile | Asn | Asn | Ala | Gly | Met | Glu | |
| | | | | 85 | | | | | 90 | | | | | 95 | | |
| aat | ccg | gtt | tca | tct | cat | gaa | atg | tct | tta | agc | gat | tgg | aat | aaa | gta | 336 |
| Asn | Pro | Val | Ser | Ser | His | Glu | Met | Ser | Leu | Ser | Asp | Trp | Asn | Lys | Val | |
| | | | 100 | | | | | 105 | | | | | 110 | | | |
| att | gat | acg | aac | tta | acg | gga | gca | ttt | tta | gga | agc | cgt | gaa | gcg | att | 384 |
| Ile | Asp | Thr | Asn | Leu | Thr | Gly | Ala | Phe | Leu | Gly | Ser | Arg | Glu | Ala | Ile | |
| | | | | 115 | | | | | 120 | | | | | 125 | | |
| aaa | tat | ttc | gtg | gaa | aat | gat | att | aag | gga | aca | gtt | att | aat | atg | tcg | 432 |
| Lys | Tyr | Phe | Val | Glu | Asn | Asp | Ile | Lys | Gly | Thr | Val | Ile | Asn | Met | Ser | |
| | 130 | | | | | 135 | | | | | 140 | | | | | |
| agt | gtt | cat | gag | aaa | att | cct | tgg | cca | tta | ttt | gtt | cat | tac | gca | gca | 480 |
| Ser | Val | His | Glu | Lys | Ile | Pro | Trp | Pro | Leu | Phe | Val | His | Tyr | Ala | Ala | |
| 145 | | | | | 150 | | | | | 155 | | | | | 160 | |
| agt | aaa | ggt | ggc | atg | aag | ctc | atg | act | gaa | aca | ctt | gca | tta | gaa | tat | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gct | cca | aaa | ggt | att | cgt | gta | aat | aac | att | ggg | ccg | gga | gcg | att | aat | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| aca | ccg | att | aac | gct | gag | aaa | ttt | gct | gat | cct | aag | cag | cgc | gca | gat | 624 |
| Thr | Pro | Ile | Asn | Ala | Glu | Lys | Phe | Ala | Asp | Pro | Lys | Gln | Arg | Ala | Asp | |
| | | | | 195 | | | | | 200 | | | | | 205 | | |
| gta | gaa | agc | atg | att | cca | atg | gga | tac | atc | gga | gag | ccg | gaa | gaa | att | 672 |
| Val | Glu | Ser | Met | Ile | Pro | Met | Gly | Tyr | Ile | Gly | Glu | Pro | Glu | Glu | Ile | |
| | 210 | | | | | 215 | | | | | 220 | | | | | |
| gca | gcg | gtt | gct | gca | tgg | cta | gct | tct | tca | gaa | gca | agt | tat | gta | aca | 720 |
| Ala | Ala | Val | Ala | Ala | Trp | Leu | Ala | Ser | Ser | Glu | Ala | Ser | Tyr | Val | Thr | |
| 225 | | | | | 230 | | | | | 235 | | | | | 240 | |
| ggg | att | acg | ctc | ttt | gct | gac | ggc | ggt | atg | aca | cag | tac | cca | tca | ttc | 768 |
| Gly | Ile | Thr | Leu | Phe | Ala | Asp | Gly | Gly | Met | Thr | Gln | Tyr | Pro | Ser | Phe | |
| | | | | 245 | | | | | 250 | | | | | 255 | | |
| caa | gca | gga | cgc | gga | taa | | | | | | | | | | | 786 |
| Gln | Ala | Gly | Arg | Gly | | | | | | | | | | | | |
| | | 260 | | | | | | | | | | | | | | |

<210> SEQ ID NO 4
<211> LENGTH: 261
<212> TYPE: PRT
<213> ORGANISM: Bacillus megaterium

<400> SEQUENCE: 4

Met Tyr Lys Asp Leu Glu Gly Lys Val Val Ile Thr Gly Ser Ser
1               5                   10                  15

Thr Gly Leu Gly Lys Ala Met Ala Ile Arg Phe Ala Thr Glu Lys Ala
            20                  25                  30

Lys Val Val Asn Tyr Arg Ser Lys Glu Glu Ala Asn Ser Val
        35                  40                  45

Leu Glu Glu Ile Lys Lys Val Gly Gly Glu Ala Ile Ala Val Lys Gly
    50                  55                  60

Asp Val Thr Val Glu Ser Asp Val Ile Asn Leu Val Gln Ser Ala Ile
65                  70                  75                  80

Lys Glu Phe Gly Lys Leu Asp Val Met Ile Asn Asn Ala Gly Met Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

Lys Tyr Phe Val Glu Asn Asp Ile Lys Gly Thr Val Ile Asn Met Ser
130                 135                 140

Ser Val His Glu Lys Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Ser Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 5
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 5 atg tat ccg gat tta aaa gga aaa gtc gtc gct att aca gga gct gct    48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca    96
Ser Gly Leu Gly Lys Ala Met Ala Ile Arg Phe Gly Lys Glu Gln Ala
            20                  25                  30

```
aaa gtg gtt atc aac tat tat agt aat aaa caa gat ccg aac gag gta        144
Lys Val Val Ile Asn Tyr Tyr Ser Asn Lys Gln Asp Pro Asn Glu Val
             35                  40                  45 aaa gaa gag gtc atc aag gcg ggt gaa gct gtt gtc gtc caa gga            192
Lys Glu Glu Val Ile Lys Ala Gly Glu Ala Val Val Val Gln Gly
 50                  55                  60 gat gtc acg aaa gag gaa gat gta aaa aat atc gtg caa acg gca att        240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa        288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc        336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att        384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc        432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca        480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac        528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac        576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat        624
Thr Pro Ile Asn Ala Glu Lys Phe Ala Asp Pro Lys Gln Lys Ala Asp
            195                 200                 205 gca gaa agc atg att cca atg gga tat atc ggc gaa ccg gag gag atc        672
Ala Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt taa tga                                            789
Gln Ala Gly Arg Gly
            260
```

<210> SEQ ID NO 6
<211> LENGTH: 261
<212> TYPE: PRT
<213> ORGANISM: Artificial
<220> FEATURE:
<223> OTHER INFORMATION: derived from bacillus

<400> SEQUENCE: 6

```
Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
             20                  25                  30

Lys Val Val Ile Asn Tyr Tyr Ser Asn Lys Gln Asp Pro Asn Glu Val
             35                  40                  45
```

```
Lys Glu Glu Val Ile Lys Ala Gly Gly Glu Ala Val Val Gln Gly
             50                  55                  60
Asp Val Thr Lys Glu Glu Asp Val Lys Asn Ile Val Gln Thr Ala Ile
 65                  70                  75                  80
Lys Glu Phe Gly Thr Leu Asp Ile Met Ile Asn Asn Ala Gly Leu Glu
                 85                  90                  95
Asn Pro Val Pro Ser His Glu Met Pro Leu Lys Asp Trp Asp Lys Val
            100                 105                 110
Ile Gly Thr Asn Leu Thr Gly Ala Phe Leu Gly Ser Arg Glu Ala Ile
        115                 120                 125
Lys Tyr Phe Val Glu Asn Asp Ile Lys Gly Asn Val Ile Asn Met Ser
130                 135                 140
Ser Val His Glu Val Ile Pro Trp Pro Leu Phe Val His Tyr Ala Ala
145                 150                 155                 160
Ser Lys Gly Gly Ile Lys Leu Met Thr Glu Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Glu Lys Phe Ala Asp Pro Lys Gln Lys Ala Asp
        195                 200                 205
Ala Glu Ser Met Ile Pro Met Gly Tyr Ile Gly Glu Pro Glu Glu Ile
210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Gln Tyr Pro Ser Phe
                245                 250                 255
Gln Ala Gly Arg Gly
            260

<210> SEQ ID NO 7
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 7 atg tat ccg gat tta aaa gga aaa gtc gtc gct att aca gga gct gct      48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
     50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80
```

```
aag gag ttc ggc aca ctc gat att atg att aat aat gcc ggt ctt gaa    288
Lys Glu Phe Gly Thr Leu Asp Ile Met Ile Asn Asn Ala Gly Leu Glu
                85                  90                  95 aat cct gtg cca tcg cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg aca aag ctg atg aca gaa aca tta gcg ttg gaa tac    528
Ser Lys Gly Gly Thr Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat    624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa tga                                        789
Gln Ala Gly Arg Gly
            260

<210> SEQ ID NO 8
<211> LENGTH: 261
<212> TYPE: PRT
<213> ORGANISM: Artificial
<220> FEATURE:
<223> OTHER INFORMATION: derived from bacillus

<400> SEQUENCE: 8

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

L

```
Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Thr Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 9
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 9 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125
```

-continued

```
aaa tat ttc gta gaa aac gat atc aag gga aat gtc att aac atg tcc        432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca        480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac        528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac        576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat        624
Thr Pro Ile Asn Ala Glu Lys Phe Ala Asp Pro Lys Gln Lys Ala Asp
        195                 200                 205 gca gaa agc atg att cca atg gga tat atc ggc gaa ccg gag gag atc        672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt taa tga                                            789
Gln Ala Gly Arg Gly
            260
```

<210> SEQ ID NO 10
<211> LENGTH: 261
<212> TYPE: PRT
<213> ORGANISM: Artificial
<220> FEATURE:
<223> OTHER INFORMATION: derived from bacillus

<400> SEQUENCE: 10

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175
```

```
Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 11
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 11
```

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |

```
tca ggg ctc gga aag gcg atg gcc att cgc ttc ggc aag gag cag gca    96
Ser Gly Leu Gly Lys Ala Met Ala Ile Arg Phe Gly Lys Glu Gln Ala
        20                  25                  30 aaa gtg gtt atc aac tat tat agt aat aaa caa gat ccg aac gag gta   144
Lys Val Val Ile Asn Tyr Tyr Ser Asn Lys Gln Asp Pro Asn Glu Val
    35                  40                  45 aaa gaa gag gtc atc aag gcg ggc ggt gaa gct gtt gtc gtc caa gga   192
Lys Glu Glu Val Ile Lys Ala Gly Gly Glu Ala Val Val Val Gln Gly
50                  55                  60 gat gtc acg aaa gag gaa gat gta aaa aat atc gtg caa acg gca att   240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa   288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc   336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att   384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc   432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca   480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac   528
Ser Lys Gly Gly Ile Lys Leu Met Thr Glu Thr Leu Ala Leu Glu Tyr
                165                 170                 175
```

```
gcg ccg aag ggc att cgc gtc aat aat att ggg cca ggt gcg atc aac    576
Ala Pro Lys Gly Ile Arg Val Asn Asn Ile Gly Pro Gly Ala Ile Asn
        180                 185                 190 acg cca atc aat gct gac aaa ttc gct gac cct aaa cag aaa gct gat    624
Thr Pro Ile Asn Ala Asp Lys Phe Ala Asp Pro Lys Gln Lys Ala Asp
    195                 200                 205 gta gaa agc aag att cca atg gga tat atc ggc gaa ccg gag gag atc    672
Val Glu Ser Lys Ile Pro Met Gly Tyr Ile Gly Glu Pro Glu Glu Ile
210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa tga                                        789
Gln Ala Gly Arg Gly
                260
```

<210> SEQ ID NO 12
<211> LENGTH: 261
<212> TYPE: PRT
<213> ORGANISM: Artificial
<220> FEATURE:
<223> OTHER INFORMATION: derived from bacillus

<400> SEQUENCE: 12

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Asp Lys Phe Ala Asp Pro Lys Gln Lys Ala Asp
        195                 200                 205

Val Glu Ser Lys Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240
```

```
Gly Ile Thr Leu Phe Ala Asp Gly Gly Met Thr Gln Tyr Pro Ser Phe
            245                 250                 255

Gln Ala Gly Arg Gly
            260

<210> SEQ ID NO 13
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 13 atg tat ccg gat tta aaa gga aaa gtc gtc gct att aca gga gct gct     48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca     96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta    144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa    288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac    528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg cca atc aat gct gac aaa ttc gct gac cct aaa cag aaa gct gat    624
Thr Pro Ile Asn Ala Asp Lys Phe Ala Asp Pro Lys Gln Lys Ala Asp
        195                 200                 205 gta gaa agc aag att cca atg gga tat atc ggc gaa ccg gag gag atc    672
Val Glu Ser Lys Ile Pro Met Gly Tyr Ile Gly Glu Pro Glu Glu Ile
    210                 215                 220
```

```
gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
            245                 250                 255 cag gca ggc cgc ggt taa tga                                        789
Gln Ala Gly Arg Gly
        260
```

<210> SEQ ID NO 14
<211> LENGTH: 261
<212> TYPE: PRT
<213> ORGANISM: Artificial
<220> FEATURE:
<223> OTHER INFORMATION: derived from bacillus

<400> SEQUENCE: 14

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Asp Lys Phe Ala Asp Pro Lys Gln Lys Ala Asp
        195                 200                 205

Val Glu Ser Lys Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 15
<211> LENGTH: 789
<212> TYPE: DNA
<213> ORGANISM: Artificial

```
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 15 atg tat ccg gat tta aaa gga aaa gtc gtc gat att aca gga gct gct        48
Met Tyr Pro Asp Leu Lys Gly Lys Val Val Asp Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca       480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac       528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat       624
Thr Pro Ile Asn Ala Glu Lys Phe Ala Asp Pro Lys Gln Lys Ala Asp
        195                 200                 205 gca gaa agc atg att cca atg gga tat atc ggc gaa ccg gag gag atc       672
Ala Glu Ser Met Ile Pro Met Gly Tyr Ile Gly Glu Pro Glu Glu Ile
    210                 215                 220 gcc gca gta gca gcc tgg ctt gct tcg aag gaa gca agc tac gtc aca       720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc       768
Gly Ile Thr Leu Phe Ala Asp Gly Gly Met Thr Gln Tyr Pro Ser Phe
                245                 250                 255 cag gca ggc cgc ggt taa tga                                           789
Gln Ala Gly Arg Gly
            260
```

<210> SEQ ID NO 16
<211> LENGTH: 261
<212> TYPE: PRT
<213> ORGANISM: Artificial
<220> FEATURE:
<223> OTHER INFORMATION: derived from bacillus

<400> SEQUENCE: 16

```
Met Tyr Pro Asp Leu Lys Gly Lys Val Val Asp Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 17
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 17

```
atg tat ccg gat tta aaa gga aaa gtc gtc gct att aca gga gct gct    48
Met Tyr Pro Asp Leu Lys Gly Lys Val Val Ala Ile Thr Gly Ala Ala
1               5                   10                  15
```

| | | | | |
|---|---|---|---|---|
| tca ggg ctc gga aag gcg atg gcc att cgc ttc ggc aag gag cag gca | | | | 96 |
| Ser Gly Leu Gly Lys Ala Met Ala Ile Arg Phe Gly Lys Glu Gln Ala | | | | |
| 20 | 25 | 30 | | |
| aaa gtg gtt atc aac tat tat agt aat aaa caa gat ccg aac gag gta | | | | 144 |
| Lys Val Val Ile Asn Tyr Tyr Ser Asn Lys Gln Asp Pro Asn Glu Val | | | | |
| 35 | 40 | 45 | | |
| aaa gaa gag gtc atc aag gcg ggc ggt gaa gct gtt gtc gtc caa gga | | | | 192 |
| Lys Glu Glu Val Ile Lys Ala Gly Gly Glu Ala Val Val Val Gln Gly | | | | |
| 50 | 55 | 60 | | |
| gat gtc acg aaa gag gaa gat gta aaa aat atc gtg caa acg gca att | | | | 240 |
| Asp Val Thr Lys Glu Glu Asp Val Lys Asn Ile Val Gln Thr Ala Ile | | | | |
| 65 | 70 | 75 | 80 | |
| aag gag ttc ggc aca ctc gat att atg att aat aat gcc ggt ttt gaa | | | | 288 |
| Lys Glu Phe Gly Thr Leu Asp Ile Met Ile Asn Asn Ala Gly Phe Glu | | | | |
| 85 | 90 | 95 | | |
| aat cct gtg cca tct cac gaa atg ccg ctc aag gat tgg gat aaa gtc | | | | 336 |
| Asn Pro Val Pro Ser His Glu Met Pro Leu Lys Asp Trp Asp Lys Val | | | | |
| 100 | 105 | 110 | | |
| atc ggc acg aac tta acg ggt gcc ttt tta gga agc cgt gaa gcg att | | | | 384 |
| Ile Gly Thr Asn Leu Thr Gly Ala Phe Leu Gly Ser Arg Glu Ala Ile | | | | |
| 115 | 120 | 125 | | |
| aaa tat ttc gta gaa aac gat atc aag gga aat gtc att aac atg tcc | | | | 432 |
| Lys Tyr Phe Val Glu Asn Asp Ile Lys Gly Asn Val Ile Asn Met Ser | | | | |
| 130 | 135 | 140 | | |
| agt gtg cac gaa gtg att cct tgg ccg tta ttt gtc cac tat gcg gca | | | | 480 |
| Ser Val His Glu Val Ile Pro Trp Pro Leu Phe Val His Tyr Ala Ala | | | | |
| 145 | 150 | 155 | 160 | |
| agt aaa ggc ggg ata aag ctg atg aca gaa aca tta gcg ttg gaa tac | | | | 528 |
| Ser Lys Gly Gly Ile Lys Leu Met Thr Glu Thr Leu Ala Leu Glu Tyr | | | | |
| 165 | 170 | 175 | | |
| gcg ccg aag ggc att cgc gtc aat aat att ggg cca ggt gcg atc aac | | | | 576 |
| Ala Pro Lys Gly Ile Arg Val Asn Asn Ile Gly Pro Gly Ala Ile Asn | | | | |
| 180 | 185 | 190 | | |
| acg cca atc aat gct gaa aaa ttc gct gac cct aaa cag aaa gct gat | | | | 624 |
| Thr Pro Ile Asn Ala Glu Lys Phe Ala Asp Pro Lys Gln Lys Ala Asp | | | | |
| 195 | 200 | 205 | | |
| gta gaa agc atg att cca atg gga tat atc ggc gaa ccg gag gag atc | | | | 672 |
| Val Glu Ser Met Ile Pro Met Gly Tyr Ile Gly Glu Pro Glu Glu Ile | | | | |
| 210 | 215 | 220 | | |
| gcc gca gta gca gcc tgg ctt gct tcg aag gaa gcc agc tac gtc aca | | | | 720 |
| Ala Ala Val Ala Ala Trp Leu Ala Ser Lys Glu Ala Ser Tyr Val Thr | | | | |
| 225 | 230 | 235 | 240 | |
| ggc atc acg tta ttc gcg gac ggc ggt atg aca caa tat cct tca ttc | | | | 768 |
| Gly Ile Thr Leu Phe Ala Asp Gly Gly Met Thr Gln Tyr Pro Ser Phe | | | | |
| 245 | 250 | 255 | | |
| cag gca ggc cgc ggt taa | | | | 786 |
| Gln Ala Gly Arg Gly | | | | |
| 260 | | | | |

```
<210> SEQ ID NO 18
<211> LENGTH: 261
<212> TYPE: PRT
<213> ORGANISM: Artificial
<220> FEATURE:
<223> OTHER INFORMATION: derived from bacillus

<400> SEQUENCE: 18
```

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

```
Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Phe Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 19
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 19

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60
```

| | | | | | | | | | | | | | | | |
|---|---|---|---|---|---|---|---|---|---|---|---|---|---|---|---|
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | 70 | | | | 75 | | | | 80 | | | | |

```
gat gtc acg aaa gag gaa gat gta aaa aat atc gtg caa acg gca att      240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac      528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct gaa aaa tac gct gac cct aaa cag aaa gct gat      624
Thr Pro Ile Asn Ala Glu Lys Tyr Ala Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 20
<211> LENGTH: 261
<212> TYPE: PRT
<213> ORGANISM: Artificial
<220> FEATURE:
<223> OTHER INFORMATION: derived from bacillus

<400> SEQUENCE: 20

```
Met Tyr Pro Asp Leu Lys Gly Lys Val Val Ala Ile Thr Gly Ala Ala
  1               5                  10                  15

Ser Gly Leu Gly Lys Ala Met Ala Ile Arg Phe Gly Lys Glu Gln Ala
                 20                  25                  30

Lys Val Val Ile Asn Tyr Tyr Ser Asn Lys Gln Asp Pro Asn Glu Val
             35                  40                  45

Lys Glu Glu Val Ile Lys Ala Gly Gly Glu Ala Val Val Gln Gly
         50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95
```

```
                Asn Pro Val Pro Ser His Glu Met Pro Leu Lys Asp Trp Asp Lys Val
                                100                 105                 110

Ile Gly Thr Asn Leu Thr Gly Ala Phe Leu Gly Ser Arg Glu Ala Ile
                            115                 120                 125

Lys Tyr Phe Val Glu Asn Asp Ile Lys Gly Asn Val Ile Asn Met Ser
                        130                 135                 140

Ser Val His Glu Val Ile Pro Trp Pro Leu Phe Val His Tyr Ala Ala
                145                 150                 155                 160

Ser Lys Gly Gly Ile Lys Leu Met Thr Glu Thr Leu Ala Leu Glu Tyr
                                165                 170                 175

Ala Pro Lys Gly Ile Arg Val Asn Asn Ile Gly Pro Gly Ala Ile Asn
                            180                 185                 190

Thr Pro Ile Asn Ala Glu Lys Tyr Ala Asp Pro Lys Gln Lys Ala Asp
                        195                 200                 205

Val Glu Ser Met Ile Pro Met Gly Tyr Ile Gly Glu Pro Glu Glu Ile
                    210                 215                 220

Ala Ala Val Ala Ala Trp Leu Ala Ser Lys Glu Ala Ser Tyr Val Thr
                225                 230                 235                 240

Gly Ile Thr Leu Phe Ala Asp Gly Gly Met Thr Gln Tyr Pro Ser Phe
                                245                 250                 255

Gln Ala Gly Arg Gly
                            260

<210> SEQ ID NO 21
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 21 atg tat ccg gat tta aaa gga aaa gtc gtc gct att aca gga gca gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ttt gaa     288
Lys Glu Phe Gly Thr Leu Asp Ile Met Ile Asn Asn Ala Gly Phe Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110
```

```
atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac    528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat    624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa                                            786
Gln Ala Gly Arg Gly
            260
```

<210> SEQ ID NO 22
<211> LENGTH: 261
<212> TYPE: PRT
<213> ORGANISM: Artificial
<220> FEATURE:
<223> OTHER INFORMATION: derived from bacillus

<400> SEQUENCE: 22

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Phe Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160
```

```
Ser Lys Gly Gly Ile Lys Leu Met Thr Glu Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
            245                 250                 255

Gln Ala Gly Arg Gly
            260
```

<210> SEQ ID NO 23
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 23

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160
```

```
agt aaa ggc ggg ata aag ctg atg aca gaa aca tta gcg ttg gaa tac       528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg cca atc aat gct aaa aaa ttc gct gac cct aaa cag aaa gct gat       624
Thr Pro Ile Asn Ala Lys Lys Phe Ala Asp Pro Lys Gln Lys Ala Asp
        195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca       720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc       768
Gly Ile Thr Leu Phe Ala Asp Gly Gly Met Thr Gln Tyr Pro Ser Phe
                245                 250                 255 cag gca ggc cgc ggt taa                                               786
Gln Ala Gly Arg Gly
                260
```

<210> SEQ ID NO 24
<211> LENGTH: 261
<212> TYPE: PRT
<213> ORGANISM: Artificial
<220> FEATURE:
<223> OTHER INFORMATION: derived from bacillus

<400> SEQUENCE: 24

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Lys Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220
```

```
Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
            245                 250                 255

Gln Ala Gly Arg Gly
        260

<210> SEQ ID NO 25
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 25 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca       480
Ser Val His Glu Val Ile Pro Trp Pro Leu Phe Val His Tyr Ala Ala
145                 150                 155                 160 agt aaa ggc ggg tta aag ctg atg aca gaa aca tta gcg ttg gaa tac       528
Ser Lys Gly Gly Leu Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat       624
Thr Pro Ile Asn Ala Glu Lys Phe Ala Asp Pro Lys Gln Lys Ala Asp
        195                 200                 205
```

```
gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 26
<211> LENGTH: 261
<212> TYPE: PRT
<213> ORGANISM: Artificial
<220> FEATURE:
<223> OTHER INFORMATION: derived from bacillus

<400> SEQUENCE: 26

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Leu Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 27
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 27

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | | 35 | | | | | 40 | | | | | 45 | | | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| 50 | | | | | 55 | | | | | 60 | | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| 130 | | | | | 135 | | | | | 140 | | | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| acg | cca | atc | aat | gct | gaa | aaa | ttc | gct | gac | cct | aaa | cag | aaa | gct | gat | 624 |
| Thr | Pro | Ile | Asn | Ala | Glu | Lys | Phe | Ala | Asp | Pro | Lys | Gln | Lys | Ala | Asp | |
| | | 195 | | | | | 200 | | | | | 205 | | | | |
| gta | gca | agc | atg | att | cca | atg | gga | tat | atc | ggc | gaa | ccg | gag | gag | atc | 672 |
| Val | Ala | Ser | Met | Ile | Pro | Met | Gly | Tyr | Ile | Gly | Glu | Pro | Glu | Glu | Ile | |
| 210 | | | | | 215 | | | | | 220 | | | | | | |
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr | |
| 225 | | | | | 230 | | | | | 235 | | | | | 240 | |

```
ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
            245                 250                 255 cag gca ggc cgt ggt taa                                             786
Gln Ala Gly Arg Gly
        260
```

<210> SEQ ID NO 28
<211> LENGTH: 261
<212> TYPE: PRT
<213> ORGANISM: Artificial
<220> FEATURE:
<223> OTHER INFORMATION: derived from bacillus

<400> SEQUENCE: 28

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Ala Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
        260
```

<210> SEQ ID NO 29
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone

```
<220> FEATURE:
<221> NAME/KEY: CDS
<222> LOCATION: (1)..(786)

<400> SEQUENCE: 29 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tcg ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg tta aag ctg atg aca gaa aca tta gcg ttg gaa tac     528
Ser Lys Gly Gly Leu Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat     624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg gag gaa gcc agc tac gtc aca     720
Ala Ala Val Ala Ala Trp Leu Ala Ser Glu Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa                                             786
Gln Ala Gly Arg Gly
            260

<210> SEQ ID NO 30
<211> LENGTH: 261
<212> TYPE: PRT
<213> ORGANISM: Artificial
```

```
<220> FEATURE:
<223> OTHER INFORMATION: derived from bacillus

<400> SEQUENCE: 30

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Leu Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Glu Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 31
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 31 atg tat ccg gat tta aaa gga aaa gtc gtc gct att aca gga gct gct     48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca     96
Ser Gly Leu Gly Lys Ala Met Ala Ile Arg Phe Gly Lys Glu Gln Ala
            20                  25                  30
```

```
aaa gtg gtt atc aac tat tat agt aat aaa caa gat ccg aac gag gta     144
Lys Val Val Ile Asn Tyr Tyr Ser Asn Lys Gln Asp Pro Asn Glu Val
             35                  40                  45 aaa gaa gag gtc atc aag gcg ggt gaa gct gtt gtc gtc caa gga         192
Lys Glu Glu Val Ile Lys Ala Gly Glu Ala Val Val Val Gln Gly
 50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac     528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg aca atc aat gct gaa aaa ttc gct gac cct aaa cag aaa gct gat     624
Thr Thr Ile Asn Ala Glu Lys Phe Ala Asp Pro Lys Gln Lys Ala Asp
            195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa                                             786
Gln Ala Gly Arg Gly
            260

<210> SEQ ID NO 32
<211> LENGTH: 261
<212> TYPE: PRT
<213> ORGANISM: Artificial
<220> FEATURE:
<223> OTHER INFORMATION: derived from bacillus

<400> SEQUENCE: 32

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45
```

```
Lys Glu Glu Val Ile Lys Ala Gly Gly Glu Ala Val Val Gln Gly
     50                  55                  60
Asp Val Thr Lys Glu Glu Asp Val Lys Asn Ile Val Gln Thr Ala Ile
 65                  70                  75                  80
Lys Glu Phe Gly Thr Leu Asp Ile Met Ile Asn Asn Ala Gly Leu Glu
                 85                  90                  95
Asn Pro Val Pro Ser His Glu Met Pro Leu Lys Asp Trp Asp Lys Val
             100                 105                 110
Ile Gly Thr Asn Leu Thr Gly Ala Phe Leu Gly Ser Arg Glu Ala Ile
         115                 120                 125
Lys Tyr Phe Val Glu Asn Asp Ile Lys Gly Asn Val Ile Asn Met Ser
130                 135                 140
Ser Val His Glu Val Ile Pro Trp Pro Leu Phe Val His Tyr Ala Ala
145                 150                 155                 160
Ser Lys Gly Gly Ile Lys Leu Met Thr Glu Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Thr Ile Asn Ala Glu Lys Phe Ala Asp Pro Lys Gln Lys Ala Asp
        195                 200                 205
Val Glu Ser Met Ile Pro Met Gly Tyr Ile Gly Glu Pro Glu Glu Ile
210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Gln Tyr Pro Ser Phe
                245                 250                 255
Gln Ala Gly Arg Gly
            260

<210> SEQ ID NO 33
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 33 atg tat ccg gat tta aaa gga aaa gtc gtc gct att aca gga gct gct      48
Met Tyr Pro Asp Leu Lys Gly Lys Val Val Ala Ile Thr Gly Ala Ala
 1               5                  10                  15 tcg ggg ctc gga aag gcg atg gcc att cgc ttc ggc aag gag cag gca      96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
     50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80
```

```
aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
           100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
               115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
       130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg tta aag ctg atg aca gaa aca tta gcg ttg gaa tac      528
Ser Lys Gly Gly Leu Lys Leu Met Thr Glu Thr Leu Ala Leu Glu Tyr
               165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
       180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
   195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
210                 215                 220 gcc gca gta gca gcc tgg ctt gct tcg gag gaa gcc agc tac gtc aca      720
Ala Ala Val Ala Ala Trp Leu Ala Ser Glu Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
               245                 250                 255 cag gca ggc cgc ggt taa                                              786
Gln Ala Gly Arg Gly
           260

<210> SEQ ID NO 34
<211> LENGTH: 261
<212> TYPE: PRT
<213> ORGANISM: Artificial
<220> FEATURE:
<223> OTHER INFORMATION: derived from bacillus

<400> SEQUENCE: 34

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Th

```
Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Leu Lys Leu Met Thr Glu Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Glu Glu Ala Ser Tyr Val Thr
225                 230                 235                 240

Gly Ile Thr Leu Phe Ala Asp Gly Gly Met Thr Gln Tyr Pro Ser Phe
            245                 250                 255

Gln Ala Gly Arg Gly
            260
```

<210> SEQ ID NO 35
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 35

```
atg tat ccg gat tta aaa gga aaa gtc gtc gcc att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca cta gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
```

```
Lys Tyr Phe Val Glu Asn Asp Ile Lys Gly Asn Val Ile Asn Met Ser
        130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg gta aag ctg atg aca gaa aca tta gcg ttg gaa tac      528
Ser Lys Gly Gly Val Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
210                 215                 220 gcc gca gtg gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 36
<211> LENGTH: 261
<212> TYPE: PRT
<213> ORGANISM: Artificial
<220> FEATURE:
<223> OTHER INFORMATION: derived from bacillus

<400> SEQUENCE: 36

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Val Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
```

```
                    180                 185                 190
Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 37
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 37
```

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | | | | 35 | | | | | 40 | | | | | 45 | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| | 50 | | | | | 55 | | | | | 60 | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | | | 115 | | | | | 120 | | | | | 125 | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | ata | aag | ctg | atg | aca | gaa | aca | tta | gcg | ttg | gaa | tac | 528 |
| Ser | Lys | Gly | Gly | Ile | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |

-continued

```
                     180                 185                 190
acg cca atc aat gct gaa aaa ttc gct gac cct aaa cag aaa gct gat        624
Thr Pro Ile Asn Ala Glu Lys Phe Ala Asp Pro Lys Gln Lys Ala Asp
        195                 200                 205 gca gaa agc atg att cca atg ggg tat atc ggc gaa ccg gag gag atc        672
Ala Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt taa tga                                            789
Gln Ala Gly Arg Gly
                260
```

<210> SEQ ID NO 38
<211> LENGTH: 261
<212> TYPE: PRT
<213> ORGANISM: Artificial
<220> FEATURE:
<223> OTHER INFORMATION: derived from bacillus

<400> SEQUENCE: 38

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255
```

Gln Ala Gly Arg Gly
        260

<210> SEQ ID NO 39
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 39

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat gtc gtg caa acg gca att     240
Asp Val Thr Lys Glu Glu Asp Val Lys Asn Val Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg ttg ttt gtc cac tat gcg gca     480
Ser Val His Glu Val Ile Pro Trp Pro Leu Phe Val His Tyr Ala Ala
145                 150                 155                 160 agt aaa ggc ggg gta aag ctg atg aca gaa aca tta gcg ttg gaa tac     528
Ser Lys Gly Gly Val Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat     624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240
```

```
ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
            245                 250                 255 cag gca ggc cgc ggt taa tga                                        789
Gln Ala Gly Arg Gly
            260
```

<210> SEQ ID NO 40
<211> LENGTH: 261
<212> TYPE: PRT
<213> ORGANISM: Artificial
<220> FEATURE:
<223> OTHER INFORMATION: derived from bacillus

<400> SEQUENCE: 40

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Val Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Val Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 41
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 41

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | | 35 | | | | | 40 | | | | | 45 | | | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| | 50 | | | | | 55 | | | | | 60 | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | | 115 | | | | | 120 | | | | | 125 | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | | 130 | | | | | 135 | | | | | 140 | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | ata | aag | ctg | atg | aca | gaa | aca | tta | gcg | ttg | gaa | tac | 528 |
| Ser | Lys | Gly | Gly | Ile | Lys | Leu | Met | Thr | Glu | Thr | Leu | Ala | Leu | Glu | Tyr | |
| | | | | 165 | | | | | 170 | | | | | 175 | | |
| gcg | cag | aag | ggc | att | cgc | gtc | aat | aat | att | ggg | cca | ggt | gcg | atc | aac | 576 |
| Ala | Gln | Lys | Gly | Ile | Arg | Val | Asn | Asn | Ile | Gly | Pro | Gly | Ala | Ile | Asn | |
| | | 180 | | | | | 185 | | | | | 190 | | | | |
| acg | cca | atc | aat | gct | gaa | aaa | ttc | gct | gac | cct | aaa | cag | aaa | gct | gat | 624 |
| Thr | Pro | Ile | Asn | Ala | Glu | Lys | Phe | Ala | Asp | Pro | Lys | Gln | Lys | Ala | Asp | |
| | | 195 | | | | | 200 | | | | | 205 | | | | |
| gta | gaa | agc | atg | att | cca | atg | gga | tat | atc | ggc | gaa | cca | gag | gag | atc | 672 |
| Val | Glu | Ser | Met | Ile | Pro | Met | Gly | Tyr | Ile | Gly | Glu | Pro | Glu | Glu | Ile | |
| | 210 | | | | | 215 | | | | | 220 | | | | | |
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr | |
| 225 | | | | | 230 | | | | | 235 | | | | | 240 | |
| ggc | atc | acg | tta | ttc | gcg | gac | ggc | ggt | atg | aca | caa | tat | cct | tca | ttc | 768 |
| Gly | Ile | Thr | Leu | Phe | Ala | Asp | Gly | Gly | Met | Thr | Gln | Tyr | Pro | Ser | Phe | |
| | | | | 245 | | | | | 250 | | | | | 255 | | |
| cag | gca | ggc | cgc | ggt | taa | tga | | | | | | | | | | 789 |
| Gln | Ala | Gly | Arg | Gly | | | | | | | | | | | | |
| | | | | 260 | | | | | | | | | | | | |

<210> SEQ ID NO 42
<211> LENGTH: 261
<212> TYPE: PRT

<213> ORGANISM: Artificial
<220> FEATURE:
<223> OTHER INFORMATION: derived from bacillus

<400> SEQUENCE: 42

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Gln Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 43
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 43 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala

```
                    20                  25                  30
aaa gtg gtt atc aac tat tat agt aat aaa caa gat ccg aac gag gta    144
Lys Val Val Ile Asn Tyr Tyr Ser Asn Lys Gln Asp Pro Asn Glu Val
             35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa    288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac    528
Ser Lys Gly Gly Ile Lys Leu Met Thr Glu Thr Leu Ala Leu Glu Tyr
                165                 170                 175 gcg cag aag ggc att cgc gtc aat aat att ggg cca ggt gcg atc aac    576
Ala Gln Lys Gly Ile Arg Val Asn Asn Ile Gly Pro Gly Ala Ile Asn
            180                 185                 190 acg cca atc aat gct gaa aaa ttc gct gac cct aaa cag aaa gct gat    624
Thr Pro Ile Asn Ala Glu Lys Phe Ala Asp Pro Lys Gln Lys Ala Asp
            195                 200                 205 gta gaa agc atg att cca atg gga tat atc ggc gaa cca gag gag atc    672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa tga                                        789
Gln Ala Gly Arg Gly
            260

<210> SEQ ID NO 44
<211> LENGTH: 261
<212> TYPE: PRT
<213> ORGANISM: Artificial
<220> FEATURE:
<223> OTHER INFORMATION: derived from bacillus

<400> SEQUENCE: 44

Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
             20                  25                  30

Lys Val Val Ile Asn Tyr Tyr Ser Asn Lys Gln Asp Pro Asn Glu Val
```

```
            35                  40                  45
Lys Glu Glu Val Ile Lys Ala Gly Gly Glu Ala Val Val Gln Gly
 50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Gln Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260
```

<210> SEQ ID NO 45
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 45

```
atg tat ccg gat tta aaa gga aaa gtc gtc gct att aca gga gct gct        48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
     50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
 65                  70                  75                  80
```

```
aag gag ttc ggc aca ctc gat att atg att aat aat gcc ggt ctt gca      288
Lys Glu Phe Gly Thr Leu Asp Ile Met Ile Asn Asn Ala Gly Leu Ala
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac      528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 46
<211> LENGTH: 261
<212> TYPE: PRT
<213> ORGANISM: Artificial
<220> FEATURE:
<223> OTHER INFORMATION: derived from bacillus

<400> SEQUENCE: 46

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Ala
                85                  90                  95

Asn Pro Val Pro Ser His Glu Met Pro Leu Lys Asp Trp Asp Lys Val
            100                 105                 110
```

```
Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 47
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 47 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
                100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
            115                 120                 125
```

-continued

```
aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac      528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca cta tat cct tca ttc      768
Gly Ile Thr Leu Phe Ala Asp Gly Gly Met Thr Leu Tyr Pro Ser Phe
                245                 250                 255 cag gca ggc cgc ggt taa                                              786
Gln Ala Gly Arg Gly
            260
```

<210> SEQ ID NO 48
<211> LENGTH: 261
<212> TYPE: PRT
<213> ORGANISM: Artificial
<220> FEATURE:
<223> OTHER INFORMATION: derived from bacillus

<400> SEQUENCE: 48

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175
```

```
Ala Pro Lys Gly Ile Arg Val Asn Asn Ile Gly Pro Gly Ala Ile Asn
        180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 49
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 49
```

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | 20 | | | | | 25 | | | | | 30 | | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | 35 | | | | | 40 | | | | | 45 | | | | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| 50 | | | | | 55 | | | | | 60 | | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | 70 | | | | | 75 | | | | | 80 | | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | ata | aag | ctg | atg | aca | gaa | aca | tta | gcg | ttg | gaa | tac | 528 |
| Ser | Lys | Gly | Gly | Ile | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |

```
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat       624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca       720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tgt cct tca ttc       768
Gly Ile Thr Leu Phe Ala Asp Gly Gly Met Thr Gln Cys Pro Ser Phe
                245                 250                 255 cag gca ggc cgc ggt taa                                               786
Gln Ala Gly Arg Gly
            260

<210> SEQ ID NO 50
<211> LENGTH: 261
<212> TYPE: PRT
<213> ORGANISM: Artificial
<220> FEATURE:
<223> OTHER INFORMATION: derived from bacillus

<400> SEQUENCE: 50

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Cys Pro Ser Phe
```

```
                    245                 250                 255
Gln Ala Gly Arg Gly
            260

<210> SEQ ID NO 51
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. megaterium GDH backbone
<220> FEATURE:
<221> NAME/KEY: CDS
<222> LOCATION: (1)..(786)

<400> SEQUENCE: 51 atg tat aaa gat tta gaa gga aaa gta gtt gtc ata aca ggt tca tct        48
Met Tyr Lys Asp Leu Glu Gly Lys Val Val Val Ile Thr Gly Ser Ser
1               5                   10                  15 acc ggt tta gga aaa gca atg gcg att cgt ttt gcg aca gaa aaa gct        96
Thr Gly Leu Gly Lys Ala Met Ala Ile Arg Phe Ala Thr Glu Lys Ala
            20                  25                  30 aaa gta gtt gtg aat tat cgt tcg aaa gaa gaa gaa gct aac agc gtt       144
Lys Val Val Val Asn Tyr Arg Ser Lys Glu Glu Glu Ala Asn Ser Val
        35                  40                  45 tta gaa gaa att aaa aaa gtc ggc gga gag gca att gcg gtt aaa ggt       192
Leu Glu Glu Ile Lys Lys Val Gly Gly Glu Ala Ile Ala Val Lys Gly
    50                  55                  60 gac gta aca gtt gag tct gac gtg atc aat tta gtt caa tct gct att       240
Asp Val Thr Val Glu Ser Asp Val Ile Asn Leu Val Gln Ser Ala Ile
65                  70                  75                  80 aaa gaa ttt gga aag tta gat gtt atg att aat aac gca gga atg gaa       288
Lys Glu Phe Gly Lys Leu Asp Val Met Ile Asn Asn Ala Gly Met Glu
                85                  90                  95 aat ccg gtt tca tct cat gaa atg tct tta agc gat tgg aat aaa gta       336
Asn Pro Val Ser Ser His Glu Met Ser Leu Ser Asp Trp Asn Lys Val
            100                 105                 110 att gat acg aac tta acg gga gca ttt tta gga agc cgt gaa gcg att       384
Ile Asp Thr Asn Leu Thr Gly Ala Phe Leu Gly Ser Arg Glu Ala Ile
        115                 120                 125 aaa tat ttc gtg gaa aat gat att aag gga aca gtt att aat atg tcg       432
Lys Tyr Phe Val Glu Asn Asp Ile Lys Gly Thr Val Ile Asn Met Ser
    130                 135                 140 agt gtt cat gag aaa att cct tgg cca tta ttt gtt cat tac gca gca       480
Ser Val His Glu Lys Ile Pro Trp Pro Leu Phe Val His Tyr Ala Ala
145                 150                 155                 160 agt aaa ggt ggc atg aag ctc atg act gaa aca ctt gca tta gaa tat       528
Ser Lys Gly Gly Met Lys Leu Met Thr Glu Thr Leu Ala Leu Glu Tyr
                165                 170                 175 gcc cca aaa ggt att cgt gta aat aac att ggg ccg gga gcg att aat       576
Ala Pro Lys Gly Ile Arg Val Asn Asn Ile Gly Pro Gly Ala Ile Asn
            180                 185                 190 aca ccg att aac gct gag aaa ttt gct gat cct aag cag cgc gca gat       624
Thr Pro Ile Asn Ala Glu Lys Phe Ala Asp Pro Lys Gln Arg Ala Asp
        195                 200                 205 gcc gaa agc atg att cca atg gga tac atc gga gag ccg gaa gaa att       672
Ala Glu Ser Met Ile Pro Met Gly Tyr Ile Gly Glu Pro Glu Glu Ile
    210                 215                 220 gca gcg gtt gct gca tgg cta gct tct tca gaa gca agt tat gta aca       720
Ala Ala Val Ala Ala Trp Leu Ala Ser Ser Glu Ala Ser Tyr Val Thr
```

```
ggg att acg ctc ttt gct gac ggc ggt atg aca cag tac cca tca ttc         768
Gly Ile Thr Leu Phe Ala Asp Gly Gly Met Thr Gln Tyr Pro Ser Phe
            245                 250                 255 caa gca gga cgc gga taa                                                 786
Gln Ala Gly Arg Gly
        260
```

<210> SEQ ID NO 52
<211> LENGTH: 261
<212> TYPE: PRT
<213> ORGANISM: Artificial
<220> FEATURE:
<223> OTHER INFORMATION: derived from bacillus

<400> SEQUENCE: 52

```
Met Tyr Lys Asp Leu Glu Gly Lys Val Val Ile Thr Gly Ser Ser
1               5                   10                  15

Thr Gly Leu Gly Lys Ala Met Ala Ile Arg Phe Ala Thr Glu Lys Ala
            20                  25                  30

Lys Val Val Asn Tyr Arg Ser Lys Glu Glu Ala Asn Ser Val
        35                  40                  45

Leu Glu Glu Ile Lys Lys Val Gly Gly Glu Ala Ile Ala Val Lys Gly
50                  55                  60

Asp Val Thr Val Glu Ser Asp Val Ile Asn Leu Val Gln Ser Ala Ile
65              70                  75                  80

Lys Glu Phe Gly Lys Leu Asp Val Met Ile Asn Asn Ala Gly Met Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

Lys Tyr Phe Val Glu Asn Asp Ile Lys Gly Thr Val Ile Asn Met Ser
130                 135                 140

Ser Val His Glu Lys Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Ala Glu Ser Met Ile Pro Met Gly Tyr Ile Gly Glu Pro Glu Glu Ile
210                 215                 220

Ala Ala Val Ala Ala Trp Leu Ala Ser Ser Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 53
<211> LENGTH: 789
<212> TYPE: DNA
<213> ORGANISM: Artificial
<220> FEATURE:
<223> OTHER INFORMATION: derived from bacillus
<220> FEATURE:

<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 53

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat     624
Thr Thr Ile Asn Ala Glu Lys Phe Ala Asp Pro Lys Gln Lys Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa tga                                          789
Gln Ala Gly Arg Gly
            260
```

<210> SEQ ID NO 54
<211> LENGTH: 261

<212> TYPE: PRT
<213> ORGANISM: Artificial
<220> FEATURE:
<223> OTHER INFORMATION: derived from bacillus

<400> SEQUENCE: 54

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 55
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 55 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96

```
                Ser Gly Leu Gly Lys Ala Met Ala Ile Arg Phe Gly Lys Glu Gln Ala
                                20                  25                  30 aaa gtg gtt atc aac tat tat agt aat aaa caa gat ccg aac gag gta           144
Lys Val Val Ile Asn Tyr Tyr Ser Asn Lys Gln Asp Pro Asn Glu Val
             35                  40                  45 aaa gaa gag gtc atc aag gcg ggc ggt gaa gct gtt gtc gtc caa gga           192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att           240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa           288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc           336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att           384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc           432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca           480
Ser Val His Glu Val Ile Pro Trp Pro Leu Phe Val His Tyr Ala Ala
145                 150                 155                 160 agt aaa ggc ggg aca aag ctg atg aca gaa aca tta gcg ttg gaa tac           528
Ser Lys Gly Gly Thr Lys Leu Met Thr Glu Thr Leu Ala Leu Glu Tyr
                165                 170                 175 gcg ccg aag ggc att cgc gtc aat aat att ggg cca ggt gcg atc aac           576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat           624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc           672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca           720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc           768
Gly Ile Thr Leu Phe Ala Asp Gly Gly Met Thr Gln Tyr Pro Ser Phe
                245                 250                 255 cag gca ggc cgc ggt taa tga                                               789
Gln Ala Gly Arg Gly
            260
```

<210> SEQ ID NO 56
<211> LENGTH: 261
<212> TYPE: PRT
<213> ORGANISM: Artificial
<220> FEATURE:
<223> OTHER INFORMATION: derived from bacillus

<400> SEQUENCE: 56

```
Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
                20                  25                  30
```

```
Lys Val Val Ile Asn Tyr Tyr Ser Asn Lys Gln Asp Pro Asn Glu Val
         35                  40                  45

Lys Glu Glu Val Ile Lys Ala Gly Gly Glu Ala Val Val Val Gln Gly
     50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
             100                 105                 110

Ile Gly Thr Asn Leu Thr Gly Ala Phe Leu Gly Ser Arg Glu Ala Ile
         115                 120                 125

Lys Tyr Phe Val Glu Asn Asp Ile Lys Gly Asn Val Ile Asn Met Ser
     130                 135                 140

Ser Val His Glu Val Ile Pro Trp Pro Leu Phe Val His Tyr Ala Ala
145                 150                 155                 160

Ser Lys Gly Gly Thr Lys Leu Met Thr Glu Thr Leu Ala Leu Glu Tyr
                 165                 170                 175

Ala Pro Lys Gly Ile Arg Val Asn Asn Ile Gly Pro Gly Ala Ile Asn
             180                 185                 190

Thr Pro Ile Asn Ala Glu Lys Phe Ala Asp Pro Lys Gln Lys Ala Asp
         195                 200                 205

Val Glu Ser Met Ile Pro Met Gly Tyr Ile Gly Glu Pro Glu Glu Ile
     210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                 245                 250                 255

Gln Ala Gly Arg Gly
             260

<210> SEQ ID NO 57
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 57 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
     50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
```

```
                65                  70                  75                  80
aag gag ttc ggc aca ctc gat att atg att aat aat gcc ggt ctt gaa        288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc        336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att        384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc        432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca        480
Ser Val His Glu Val Ile Pro Trp Pro Leu Phe Val His Tyr Ala Ala
145                 150                 155                 160 agt aaa ggc ggg aca aag ctg atg aca gaa aca tta gcg ttg gaa tac        528
Ser Lys Gly Gly Thr Lys Leu Met Thr Glu Thr Leu Ala Leu Glu Tyr
                165                 170                 175 gcg ccg aag ggc att cgc gtc aat aat att ggg cca ggt gcg atc aac        576
Ala Pro Lys Gly Ile Arg Val Asn Asn Ile Gly Pro Gly Ala Ile Asn
            180                 185                 190 acg cca atc aat gct aag aaa tat gct gac cct aaa cag aaa gct gat        624
Thr Pro Ile Asn Ala Lys Lys Tyr Ala Asp Pro Lys Gln Lys Ala Asp
        195                 200                 205 gcc gaa agc atg att cca atg gga tat atc ggc gaa ccg gag gag atc        672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg ttg ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt taa tga                                             789
Gln Ala Gly Arg Gly
            260

<210> SEQ ID NO 58
<211> LENGTH: 261
<212> TYPE: PRT
<213> ORGANISM: Artificial
<220> FEATURE:
<223> OTHER INFORMATION: derived from bacillus

<400> SEQUENCE: 58

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
```

```
                    100                 105                 110
Ile Gly Thr Asn Leu Thr Gly Ala Phe Leu Gly Ser Arg Glu Ala Ile
            115                 120                 125
Lys Tyr Phe Val Glu Asn Asp Ile Lys Gly Asn Val Ile Asn Met Ser
        130                 135                 140
Ser Val His Glu Val Ile Pro Trp Pro Leu Phe Val His Tyr Ala Ala
145                 150                 155                 160
Ser Lys Gly Gly Thr Lys Leu Met Thr Glu Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Lys Lys Tyr Ala Asp Pro Lys Gln Lys Ala Asp
        195                 200                 205
Ala Glu Ser Met Ile Pro Met Gly Tyr Ile Gly Glu Pro Glu Glu Ile
    210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Gln Tyr Pro Ser Phe
                245                 250                 255
Gln Ala Gly Arg Gly
            260

<210> SEQ ID NO 59
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 59 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125
```

```
aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct aag aaa tat gct gac cct aaa cag aaa gct gat      624
Thr Pro Ile Asn Ala Lys Lys Tyr Ala Asp Pro Lys Gln Lys Ala Asp
        195                 200                 205 gcc gaa agc atg att cca atg gga tat atc ggc gaa ccg gag gag atc      672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc gtc acg tta ttc gcg gac ggc ggt atg aca caa tat cct tca ttc      768
Gly Val Thr Leu Phe Ala Asp Gly Gly Met Thr Gln Tyr Pro Ser Phe
                245                 250                 255 cag gca ggc cgc ggt taa tga                                          789
Gln Ala Gly Arg Gly
            260
```

<210> SEQ ID NO 60
<211> LENGTH: 261
<212> TYPE: PRT
<213> ORGANISM: Artificial
<220> FEATURE:
<223> OTHER INFORMATION: derived from bacillus

<400> SEQUENCE: 60

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175
```

```
Ala Pro Lys Gly Ile Arg Val Asn Asn Ile Gly Pro Gly Ala Ile Asn
            180                 185                 190

Thr Pro Ile Asn Ala Lys Lys Tyr Ala Asp Pro Lys Gln Lys Ala Asp
            195                 200             205

Ala Glu Ser Met Ile Pro Met Gly Tyr Ile Gly Pro Glu Glu Ile
        210                 215                 220

Ala Ala Val Ala Ala Trp Leu Ala Ser Lys Glu Ala Ser Tyr Val Thr
225                 230                 235                 240

Gly Val Thr Leu Phe Ala Asp Gly Gly Met Thr Gln Tyr Pro Ser Phe
                245                 250                 255

Gln Ala Gly Arg Gly
            260

<210> SEQ ID NO 61
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 61 atg tat ccg gat tta aaa gga aaa gtc gtc gct att aca gga gct gct     48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca     96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta    144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gca    288
Lys Glu Phe Gly Thr Leu Asp Ile Met Ile Asn Asn Ala Gly Leu Ala
                85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac    528
Ser Lys Gly Gly Met Lys Leu Met Thr Glu Thr Leu Ala Leu Glu Tyr
                165                 170                 175
```

```
gcg ccg aag ggc att cgc gtc aat aat att ggg cca ggt gcg atc aac      576
Ala Pro Lys Gly Ile Arg Val Asn Asn Ile Gly Pro Gly Ala Ile Asn
        180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
        195                 200                 205 gcc gaa agc atg att cca atg gga tat atc ggc gaa ccg gag gag atc      672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc gtc acg tta ttc gcg gac ggc ggt atg aca caa tat cct tca ttc      768
Gly Val Thr Leu Phe Ala Asp Gly Gly Met Thr Gln Tyr Pro Ser Phe
                245                 250                 255 cag gca ggc cgc ggt taa tga                                          789
Gln Ala Gly Arg Gly
        260
```

<210> SEQ ID NO 62
<211> LENGTH: 261
<212> TYPE: PRT
<213> ORGANISM: Artificial
<220> FEATURE:
<223> OTHER INFORMATION: derived from bacillus

<400> SEQUENCE: 62

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Ala
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240
```

```
Gly Val Thr Leu Phe Ala Asp Gly Gly Met Thr Gln Tyr Pro Ser Phe
                245                 250                 255
Gln Ala Gly Arg Gly
            260

<210> SEQ ID NO 63
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 63 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat     624
Thr Pro Ile Asn Ala Glu Lys Phe Ala Asp Pro Lys Gln Lys Ala Asp
        195                 200                 205 gcc gaa agc atg att cca atg gga tat atc ggc gaa ccg gag gag atc     672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
```

```
Ala Ala Val Ala Ala Trp Leu Ala Ser Lys Glu Ala Ser Tyr Val Thr
225                 230                 235                 240 ggc gtc acg tta ttc gcg gac ggc ggt atg aca cta tat cct tca ttc       768
Gly Val Thr Leu Phe Ala Asp Gly Gly Met Thr Leu Tyr Pro Ser Phe
                245                 250                 255 cag gca ggc cgc ggt taa tga                                           789
Gln Ala Gly Arg Gly
            260
```

<210> SEQ ID NO 64
<211> LENGTH: 261
<212> TYPE: PRT
<213> ORGANISM: Artificial
<220> FEATURE:
<223> OTHER INFORMATION: derived from bacillus

<400> SEQUENCE: 64

```
Met Tyr Pro Asp Leu Lys Gly Lys Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Ser Asn Lys Gln Asp Pro Asn Glu Val
            35                  40                  45

Lys Glu Glu Val Ile Lys Ala Gly Gly Glu Ala Val Val Gln Gly
50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Val Thr Leu Phe Ala Asp Gly Gly Met Thr Leu Tyr Pro Ser Phe
                245                 250                 255

Gln Ala Gly Arg Gly
            260
```

<210> SEQ ID NO 65
<211> LENGTH: 789
<212> TYPE: DNA
<213> ORGANISM: Artificial
<220> FEATURE:
<223> OTHER INFORMATION: derived from bacillus

```
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 65 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gca     288
Lys Glu Phe Gly Thr Leu Asp Ile Met Ile Asn Asn Ala Gly Leu Ala
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat     624
Thr Pro Ile Asn Ala Glu Lys Phe Ala Asp Pro Lys Gln Lys Ala Asp
        195                 200                 205 gcc gaa agc atg att cca atg gga tat atc ggc gaa ccg gag gag atc     672
Ala Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc gtc acg tta ttc gcg gac ggc ggt atg aca cta tat cct tca ttc     768
Gly Val Thr Leu Phe Ala Asp Gly Gly Met Thr Leu Tyr Pro Ser Phe
                245                 250                 255 cag gca ggc cgc ggt taa tga                                         789
Gln Ala Gly Arg Gly
            260

<210> SEQ ID NO 66
```

```
<211> LENGTH: 261
<212> TYPE: PRT
<213> ORGANISM: Artificial
<220> FEATURE:
<223> OTHER INFORMATION: derived from bacillus

<400> SEQUENCE: 66

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Ala
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Val Thr Leu Phe Ala Asp Gly Gly Met Thr Leu Tyr Pro Ser Phe
                245                 250                 255

Gln Ala Gly Arg Gly
            260

<210> SEQ ID NO 67
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 67 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15
```

```
tca ggg ctc gga aag gcg atg gcc att cgc ttc ggc aag gag cag gca      96
Ser Gly Leu Gly Lys Ala Met Ala Ile Arg Phe Gly Lys Glu Gln Ala
         20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
             35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80 aag gag ttc ggc aca ctc gat att atg att aat agt gcc ggt ctt gaa     288
Lys Glu Phe Gly Thr Leu Asp Ile Met Ile Asn Ser Ala Gly Leu Glu
                 85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat     624
Thr Thr Ile Asn Ala Glu Lys Phe Ala Asp Pro Lys Gln Lys Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa tga                                         789
Gln Ala Gly Arg Gly
            260

<210> SEQ ID NO 68
<211> LENGTH: 261
<212> TYPE: PRT
<213> ORGANISM: Artificial
<220> FEATURE:
<223> OTHER INFORMATION: derived from bacillus

<400> SEQUENCE: 68

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30
```

-continued

```
Lys Val Val Ile Asn Tyr Tyr Ser Asn Lys Gln Asp Pro Asn Glu Val
             35                  40                  45

Lys Glu Glu Val Ile Lys Ala Gly Gly Glu Ala Val Val Gln Gly
 50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Ser Ala Gly Leu Glu
                 85                  90                  95

Asn Pro Val Pro Ser His Glu Met Pro Leu Lys Asp Trp Asp Lys Val
             100                 105                 110

Ile Gly Thr Asn Leu Thr Gly Ala Phe Leu Gly Ser Arg Glu Ala Ile
         115                 120                 125

Lys Tyr Phe Val Glu Asn Asp Ile Lys Gly Asn Val Ile Asn Met Ser
 130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                 165                 170                 175

Ala Pro Lys Gly Ile Arg Val Asn Asn Ile Gly Pro Gly Ala Ile Asn
             180                 185                 190

Thr Thr Ile Asn Ala Glu Lys Phe Ala Asp Pro Lys Gln Lys Ala Asp
         195                 200                 205

Val Glu Ser Met Ile Pro Met Gly Tyr Ile Gly Glu Pro Glu Glu Ile
 210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                 245                 250                 255

Gln Ala Gly Arg Gly
             260
```

<210> SEQ ID NO 69
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 69

```
atg tat ccg gat tta aaa gga aaa gtc gtc gct att aca gga gct gct      48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att     240
```

```
Asp Val Thr Lys Glu Glu Asp Val Lys Asn Ile Val Gln Thr Ala Ile
 65                  70                  75                  80 aag gag ttc ggc aca ctc gat att atg att aat agt gcc ggt ctt gaa    288
Lys Glu Phe Gly Thr Leu Asp Ile Met Ile Asn Ser Ala Gly Leu Glu
                 85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg aca aag ctg atg aca gaa aca tta gcg ttg gaa tac    528
Ser Lys Gly Gly Thr Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat    624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa tga                                        789
Gln Ala Gly Arg Gly
            260

<210> SEQ ID NO 70
<211> LENGTH: 261
<212> TYPE: PRT
<213> ORGANISM: Artificial
<220> FEATURE:
<223> OTHER INFORMATION: derived from bacillus

<400> SEQUENCE: 70

Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Ser Ala Gly Leu Glu
                 85                  90                  95
```

```
Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Thr Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 71
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 71

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat agt gcc ggt ctt gaa     288
Lys Glu Phe Gly Thr Leu Asp Ile Met Ile Asn Ser Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
```

```
aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
        195                 200                 205 gcc gaa agc atg att cca atg gga tat atc ggc gaa ccg gag gag atc      672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc gtc acg tta ttc gcg gac ggc ggt atg aca cta tat cct tca ttc      768
Gly Val Thr Leu Phe Ala Asp Gly Gly Met Thr Leu Tyr Pro Ser Phe
                245                 250                 255 cag gca ggc cgc ggt taa tga                                          789
Gln Ala Gly Arg Gly
                260

<210> SEQ ID NO 72
<211> LENGTH: 261
<212> TYPE: PRT
<213> ORGANISM: Artificial
<220> FEATURE:
<223> OTHER INFORMATION: derived from bacillus

<400> SEQUENCE: 72

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Ser Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
```

```
                165                 170                 175
Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Val Thr Leu Phe Ala Asp Gly Gly Met Thr Leu Tyr Pro Ser Phe
                245                 250                 255

Gln Ala Gly Arg Gly
            260

<210> SEQ ID NO 73
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 73 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg ctt aag ctg atg aca gaa aca tta gcg ttg gaa tac     528
Ser Lys Gly Gly Leu Lys Leu Met Thr Glu Thr Leu Ala Leu Glu Tyr
                165                 170                 175
```

```
gcg ccg aag ggc att cgc gtc aat aat att ggg cca ggt gcg atc aac        576
Ala Pro Lys Gly Ile Arg Val Asn Asn Ile Gly Pro Gly Ala Ile Asn
        180                 185                 190 acg cca atc aat gct gaa aaa ttc gct gac cct aaa cag aaa gct gat        624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc        672
Val Glu Ser Met Ile Pro Met Gly Tyr Ile Gly Glu Pro Glu Glu Ile
        210                 215                 220 gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt taa tga                                            789
Gln Ala Gly Arg Gly
                260
```

<210> SEQ ID NO 74
<211> LENGTH: 261
<212> TYPE: PRT
<213> ORGANISM: Artificial
<220> FEATURE:
<223> OTHER INFORMATION: derived from bacillus

<400> SEQUENCE: 74

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Leu Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240
```

```
Gly Ile Thr Leu Phe Ala Asp Gly Gly Met Thr Gln Tyr Pro Ser Phe
            245                 250                 255
Gln Ala Gly Arg Gly
            260

<210> SEQ ID NO 75
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 75 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
                100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
        130                 135                 140 agt gtg cac gaa gtg att cct tgg ccg tta ttt gtc cac tat gcg gca       480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac       528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat       624
Thr Thr Ile Asn Ala Glu Lys Phe Ala Asp Pro Lys Gln Lys Ala Asp
        195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
    210                 215                 220
```

```
gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca cta tat cct tca ttc    768
Gly Ile Thr Leu Phe Ala Asp Gly Gly Met Thr Leu Tyr Pro Ser Phe
                245                 250                 255 cag gca ggc cgc ggt taa tga                                        789
Gln Ala Gly Arg Gly
            260
```

<210> SEQ ID NO 76
<211> LENGTH: 261
<212> TYPE: PRT
<213> ORGANISM: Artificial
<220> FEATURE:
<223> OTHER INFORMATION: derived from bacillus

<400> SEQUENCE: 76

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 77
<211> LENGTH: 789
<212> TYPE: DNA
<213> ORGANISM: Artificial
<220> FEATURE:

<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 77

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
                100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg ctt aag ctg atg aca gaa aca tta gcg ttg gaa tac     528
Ser Lys Gly Gly Leu Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
                180                 185                 190 acg cca atc aat gct gaa aaa ttc gct gac cct aaa cag aaa gct gat     624
Thr Pro Ile Asn Ala Glu Lys Phe Ala Asp Pro Lys Gln Lys Ala Asp
            195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca cta tat cct tca ttc     768
Gly Ile Thr Leu Phe Ala Asp Gly Gly Met Thr Leu Tyr Pro Ser Phe
                245                 250                 255 cag gca ggc cgc ggt taa tga                                         789
Gln Ala Gly Arg Gly
                260
```

<210> SEQ ID NO 78
<211> LENGTH: 261
<212> TYPE: PRT
<213> ORGANISM: Artificial
<220> FEATURE:
<223> OTHER INFORMATION: derived from bacillus

<400> SEQUENCE: 78

```
Met Tyr Pro Asp Leu Lys Gly Lys Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Leu Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 79
<211> LENGTH: 32
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: B subtilus GDH forward primer

<400> SEQUENCE: 79
gaattcgccc atatgtatcc ggatttaaaa gg          32

<210> SEQ ID NO 80
<211> LENGTH: 34
<212> TYPE: DNA

-continued

<210> SEQ ID NO 80
<211> LENGTH: 34
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: B subtilus reverse GDH primer

<400> SEQUENCE: 80
tggccggatc ctcattaacc gcggcctgcc tgga                               34

<210> SEQ ID NO 81
<211> LENGTH: 32
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: B. megaterium GDH forward primer

<400> SEQUENCE: 81
gaattcgccc atatgtataa agatttagaa gg                                 32

<210> SEQ ID NO 82
<211> LENGTH: 33
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: B. megaterium GDH reverse primer

<400> SEQUENCE: 82
ggccggatcc tcattatccg cgtcctgctt gga                                33

<210> SEQ ID NO 83
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 83

```
atg tat ccg gat tta aaa gga aaa gtc gtc gct att aca gga gct gct    48
Met Tyr Pro Asp Leu Lys Gly Lys Val Val Ala Ile Thr Gly Ala Ala
1               5                  10                  15 tca ggg ctc gga aag gcg atg gcc att cgc ttc ggc aag gag cag gca    96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta   144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga   192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att   240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa   288
Lys Glu Phe Gly Thr Leu Asp Ile Met Ile Asn Asn Ala Gly Leu Glu
```

```
aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat     624
Thr Pro Ile Asn Ala Glu Lys Phe Ala Asp Pro Lys Gln Lys Ala Asp
        195                 200                 205 gcc gaa agc atg att cca atg gga tat atc ggc gaa ccg gag gag atc     672
Ala Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc gtc acg tta ttc gcg gac ggc ggt atg aca caa tat cct tca ttc     768
Gly Val Thr Leu Phe Ala Asp Gly Gly Met Thr Gln Tyr Pro Ser Phe
                245                 250                 255 cag gca ggc cgc ggt taa tga                                         789
Gln Ala Gly Arg Gly
            260
```

<210> SEQ ID NO 84
<211> LENGTH: 261
<212> TYPE: PRT
<213> ORGANISM: Artificial
<220> FEATURE:
<223> OTHER INFORMATION: derived from bacillus

<400> SEQUENCE: 84

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125
```

```
Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Ala Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Val Thr Leu Phe Ala Asp Gly Gly Met Thr Gln Tyr Pro Ser Phe
                245                 250                 255

Gln Ala Gly Arg Gly
            260

<210> SEQ ID NO 85
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 85 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg ccg tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140
```

```
agt gtg cac gaa gtg att cct tgg ccg tta ttt gtc cac tat gcg gca        480
Ser Val His Glu Val Ile Pro Trp Pro Leu Phe Val His Tyr Ala Ala
145                 150                 155                 160 agt aaa ggc ggg ctt aag ctg atg aca gaa aca tta gcg ttg gaa tac        528
Ser Lys Gly Gly Leu Lys Leu Met Thr Glu Thr Leu Ala Leu Glu Tyr
                165                 170                 175 gcg ccg aag ggc att cgc gtc aat aat att ggg cca ggt gcg atc aac        576
Ala Pro Lys Gly Ile Arg Val Asn Asn Ile Gly Pro Gly Ala Ile Asn
            180                 185                 190 acg cca atc aat gct gaa aaa ttc act gac cct aaa cag aaa gct gat        624
Thr Pro Ile Asn Ala Glu Lys Phe Thr Asp Pro Lys Gln Lys Ala Asp
        195                 200                 205 gta gaa agc atg att cca atg gga tat atc ggc gaa ccg gag gag atc        672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt taa                                                786
Gln Ala Gly Arg Gly
            260
```

<210> SEQ ID NO 86
<211> LENGTH: 261
<212> TYPE: PRT
<213> ORGANISM: Artificial
<220> FEATURE:
<223> OTHER INFORMATION: derived from bacillus

<400> SEQUENCE: 86

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Leu Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190
```

```
Thr Pro Ile Asn Ala Glu Lys Phe Thr Asp Pro Lys Gln Lys Ala Asp
        195                 200                 205

Val Glu Ser Met Ile Pro Met Gly Tyr Ile Gly Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 87
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 87
```

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | gac | gag | gta | 144 |
| Lys | Val | Val | Ile | Asn | Tyr | Tyr | Ser | Asn | Lys | Gln | Asp | Pro | Asp | Glu | Val | |
| | | | | 35 | | | | | 40 | | | | | 45 | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| | | 50 | | | | | 55 | | | | | 60 | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | | | 115 | | | | | 120 | | | | | 125 | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | | | 130 | | | | | 135 | | | | | 140 | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |

-continued

```
acg acg atc aat gct gag aaa ttt gct gac cct aaa cag aaa gct gat      624
Thr Thr Ile Asn Ala Glu Lys Phe Ala Asp Pro Lys Gln Lys Ala Asp
        195                 200                 205 gta gaa agc atg att cca atg ggt tat atc ggc gaa ccg gag gag atc      672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 88
<211> LENGTH: 261
<212> TYPE: PRT
<213> ORGANISM: Artificial
<220> FEATURE:
<223> OTHER INFORMATION: derived from bacillus

<400> SEQUENCE: 88

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asp Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
```

<210> SEQ ID NO 89
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 89

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| 130 | | | | | 135 | | | | | 140 | | | | | | |

| | | | | | | | | | | | | | | | | |
|---|---|---|---|---|---|---|---|---|---|---|---|---|---|---|---|---|
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| acg | acg | atc | aat | gct | gag | aaa | ttt | gct | gac | cct | aaa | cag | aaa | gct | gat | 624 |
| Thr | Thr | Ile | Asn | Ala | Glu | Lys | Phe | Ala | Asp | Pro | Lys | Gln | Lys | Ala | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| gta | gaa | agc | atg | att | cca | atg | ctt | tat | atc | ggt | gaa | ccg | gag | gag | atc | 672 |
| Val | Glu | Ser | Met | Ile | Pro | Met | Leu | Tyr | Ile | Gly | Glu | Pro | Glu | Glu | Ile | |
| 210 | | | | | 215 | | | | | 220 | | | | | | |

| | | | | | | | | | | | | | | | | |
|---|---|---|---|---|---|---|---|---|---|---|---|---|---|---|---|---|
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggc | atc | acg | tta | ttc | gcg | gac | ggc | ggt | atg | aca | caa | tat | cct | tca | ttc | 768 |

-continued

```
Gly Ile Thr Leu Phe Ala Asp Gly Gly Met Thr Gln Tyr Pro Ser Phe
            245                 250                 255 cag gca ggc cgc ggt taa                                          786
Gln Ala Gly Arg Gly
            260

<210> SEQ ID NO 90
<211> LENGTH: 261
<212> TYPE: PRT
<213> ORGANISM: Artificial
<220> FEATURE:
<223> OTHER INFORMATION: derived from bacillus

<400> SEQUENCE: 90

Met Tyr Pro Asp Leu Lys Gly Lys Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
        195                 200                 205

Val Glu Ser Met Ile Pro Met Leu Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 91
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
```

<221> NAME/KEY: CDS
<222> LOCATION: (1)..(786)

<400> SEQUENCE: 91

```
atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc act ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca       480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac       528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg acg atc aat gct gag aaa ttt gct gac cct ctg cag aaa gct gat       624
Thr Thr Ile Asn Ala Glu Lys Phe Ala Asp Pro Leu Gln Lys Ala Asp
        195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca       720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc       768
Gly Ile Thr Leu Phe Ala Asp Gly Gly Met Thr Gln Tyr Pro Ser Phe
                245                 250                 255 cag gca ggc cgc ggt taa                                               786
Gln Ala Gly Arg Gly
            260
```

<210> SEQ ID NO 92
<211> LENGTH: 261
<212> TYPE: PRT
<213> ORGANISM: Artificial
<220> FEATURE:

<223> OTHER INFORMATION: derived from bacillus

<400> SEQUENCE: 92

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Leu Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 93
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 93

```
atg tat ccg gat tta aaa gga aaa gtc gtc gct att aca gga gct gct    48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca    96
Ser Gly Leu Gly Lys Ala Met Ala Ile Arg Phe Gly Lys Glu Gln Ala
            20                  25                  30
```

```
aaa gtg gtt atc aac tat tat agt aat aaa caa gat ccg aac gag gta      144
Lys Val Val Ile Asn Tyr Tyr Ser Asn Lys Gln Asp Pro Asn Glu Val
         35                  40                  45 aaa gaa gag gtc atc aag gcg ggt gaa gct gtt gtc gtc caa gga          192
Lys Glu Glu Val Ile Lys Ala Gly Glu Ala Val Val Val Gln Gly
 50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat      624
Thr Thr Ile Asn Ala Glu Lys Phe Ala Asp Pro Lys Gln Lys Ala Asp
            195                 200                 205 gta gaa act atg att cca atg gga tat atc ggc gaa ccg gag gag atc      672
Val Glu Thr Met Ile Pro Met Gly Tyr Ile Gly Glu Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 94
<211> LENGTH: 261
<212> TYPE: PRT
<213> ORGANISM: Artificial
<220> FEATURE:
<223> OTHER INFORMATION: derived from bacillus

<400> SEQUENCE: 94

Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
         35                  40                  45
```

```
Lys Glu Glu Val Ile Lys Ala Gly Gly Glu Ala Val Val Gln Gly
 50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
            195                 200                 205

Val Glu Thr Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 95
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 95 atg tat ccg gat tta aaa gga aaa gtc gtc gct att aca gga gct gct        48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa       288
```

```
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat gct gag aaa ttt gct gac agg aaa cag aaa gct gat      624
Thr Thr Ile Asn Ala Glu Lys Phe Ala Asp Arg Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 96
<211> LENGTH: 261
<212> TYPE: PRT
<213> ORGANISM: Artificial
<220> FEATURE:
<223> OTHER INFORMATION: derived from bacillus

<400> SEQUENCE: 96

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
```

```
                115                 120                 125
Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Arg Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260

<210> SEQ ID NO 97
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 97 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
```

```
            130                 135                 140
agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat     624
Thr Thr Ile Asn Ala Glu Lys Phe Ala Asp Pro Lys Gln Lys Ala Asp
        195                 200                 205 gta aaa agc atg att cca atg gga tat atc ggc gaa ccg gag gag atc     672
Val Lys Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa                                             786
Gln Ala Gly Arg Gly
            260

<210> SEQ ID NO 98
<211> LENGTH: 261
<212> TYPE: PRT
<213> ORGANISM: Artificial
<220> FEATURE:
<223> OTHER INFORMATION: derived from bacillus

<400> SEQUENCE: 98

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190
```

```
Thr Thr Ile Asn Ala Glu Lys Phe Ala Asp Pro Lys Gln Lys Ala Asp
        195                 200                 205

Val Lys Ser Met Ile Pro Met Gly Tyr Ile Gly Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 99
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 99 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat att aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca       480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac       528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190
```

```
acg acg atc aat gct gct aaa ttt gct gac cct aaa cag aaa gct gat     624
Thr Thr Ile Asn Ala Ala Lys Phe Ala Asp Pro Lys Gln Lys Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
            245                 250                 255 cag gca ggc cgc ggt taa                                             786
Gln Ala Gly Arg Gly
            260

<210> SEQ ID NO 100
<211> LENGTH: 261
<212> TYPE: PRT
<213> ORGANISM: Artificial
<220> FEATURE:
<223> OTHER INFORMATION: derived from bacillus

<400> SEQUENCE: 100

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Ala Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255
```

Gln Ala Gly Arg Gly
        260

<210> SEQ ID NO 101
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 101

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | 20 | | | | | 25 | | | | | 30 | | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | 35 | | | | | 40 | | | | | 45 | | | | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| 50 | | | | | 55 | | | | | 60 | | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| acg | acg | atc | aat | gct | gag | aaa | ttt | gct | gac | aat | aaa | cag | aaa | gct | gat | 624 |
| Thr | Thr | Ile | Asn | Ala | Glu | Lys | Phe | Ala | Asp | Asn | Lys | Gln | Lys | Ala | Asp | |
| | | 195 | | | | | 200 | | | | | 205 | | | | |
| gta | gaa | agc | atg | att | cca | atg | gga | tat | atc | ggc | gaa | ccg | gag | gag | atc | 672 |
| Val | Glu | Ser | Met | Ile | Pro | Met | Gly | Tyr | Ile | Gly | Glu | Pro | Glu | Glu | Ile | |
| | 210 | | | | | 215 | | | | | 220 | | | | | |
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr | |
| 225 | | | | | 230 | | | | | 235 | | | | | 240 | |

```
ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
            245                 250                 255 cag gca ggc cgc ggt taa                                              786
Gln Ala Gly Arg Gly
        260
```

<210> SEQ ID NO 102
<211> LENGTH: 261
<212> TYPE: PRT
<213> ORGANISM: Artificial
<220> FEATURE:
<223> OTHER INFORMATION: derived from bacillus

<400> SEQUENCE: 102

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Asn Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 103
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone

```
<220> FEATURE:
<221> NAME/KEY: CDS
<222> LOCATION: (1)..(786)

<400> SEQUENCE: 103 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat gct gag aaa ttt gct gac gat aaa cag aaa gct gat      624
Thr Thr Ile Asn Ala Glu Lys Phe Ala Asp Asp Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 104
<211> LENGTH: 261
<212> TYPE: PRT
<213> ORGANISM: Artificial
```

```
<220> FEATURE:
<223> OTHER INFORMATION: derived from bacillus

<400> SEQUENCE: 104

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Asp Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 105
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 105 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30
```

| | | |
|---|---|---|
| aaa gtg gtt atc aac tat tat agt aat aaa caa gat ccg aac gag gta<br>Lys Val Val Ile Asn Tyr Tyr Ser Asn Lys Gln Asp Pro Asn Glu Val<br>35 40 45 | | 144 |
| aaa gaa gag gtc atc aag gcg ggc ggt gaa gct gtt gtc gtc caa gga<br>Lys Glu Glu Val Ile Lys Ala Gly Gly Glu Ala Val Val Val Gln Gly<br>50 55 60 | | 192 |
| gat gtc acg aaa gag gaa gat gta aaa aat atc gtg caa acg gca att<br>Asp Val Thr Lys Glu Glu Asp Val Lys Asn Ile Val Gln Thr Ala Ile<br>65 70 75 80 | | 240 |
| aag gag ttc ggc aca ctc gat att atg att aat aat gcc ggt ctt gaa<br>Lys Glu Phe Gly Thr Leu Asp Ile Met Ile Asn Asn Ala Gly Leu Glu<br>85 90 95 | | 288 |
| aat cct gtg cca tct cac gaa atg ccg ctc aag gat tgg gat aaa gtc<br>Asn Pro Val Pro Ser His Glu Met Pro Leu Lys Asp Trp Asp Lys Val<br>100 105 110 | | 336 |
| atc ggc acg aac tta acg ggt gcc ttt tta gga agc cgt gaa gcg att<br>Ile Gly Thr Asn Leu Thr Gly Ala Phe Leu Gly Ser Arg Glu Ala Ile<br>115 120 125 | | 384 |
| aaa tat ttc gta gaa aac gat atc aag gga aat gtc att aac atg tcc<br>Lys Tyr Phe Val Glu Asn Asp Ile Lys Gly Asn Val Ile Asn Met Ser<br>130 135 140 | | 432 |
| agt gtg cac gaa gtg att cct tgg ccg tta ttt gtc cac tat gcg gca<br>Ser Val His Glu Val Ile Pro Trp Pro Leu Phe Val His Tyr Ala Ala<br>145 150 155 160 | | 480 |
| agt aaa ggc ggg atg aag ctg atg aca gaa aca tta gcg ttg gaa tac<br>Ser Lys Gly Gly Met Lys Leu Met Thr Glu Thr Leu Ala Leu Glu Tyr<br>165 170 175 | | 528 |
| gcg ccg aag ggc att cgc gtc aat aat att ggg cca ggt gcg atc aac<br>Ala Pro Lys Gly Ile Arg Val Asn Asn Ile Gly Pro Gly Ala Ile Asn<br>180 185 190 | | 576 |
| acg acg atc aat gct ggt aaa ttt gct gac cct aaa cag aaa gct gat<br>Thr Thr Ile Asn Ala Gly Lys Phe Ala Asp Pro Lys Gln Lys Ala Asp<br>195 200 205 | | 624 |
| gta gaa agc atg att cca atg gga tat atc ggc gaa ccg gag gag atc<br>Val Glu Ser Met Ile Pro Met Gly Tyr Ile Gly Glu Pro Glu Glu Ile<br>210 215 220 | | 672 |
| gcc gca gta gca gcc tgg ctt gct tcg aag gaa gcc agc tac gtc aca<br>Ala Ala Val Ala Ala Trp Leu Ala Ser Lys Glu Ala Ser Tyr Val Thr<br>225 230 235 240 | | 720 |
| ggc atc acg tta ttc gcg gac ggc ggt atg aca caa tat cct tca ttc<br>Gly Ile Thr Leu Phe Ala Asp Gly Gly Met Thr Gln Tyr Pro Ser Phe<br>245 250 255 | | 768 |
| cag gca ggc cgc ggt taa<br>Gln Ala Gly Arg Gly<br>260 | | 786 |

<210> SEQ ID NO 106
<211> LENGTH: 261
<212> TYPE: PRT
<213> ORGANISM: Artificial
<220> FEATURE:
<223> OTHER INFORMATION: derived from bacillus

<400> SEQUENCE: 106

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
                35                  40                  45

```
Lys Glu Glu Val Ile Lys Ala Gly Gly Glu Ala Val Val Gln Gly
     50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Gly Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 107
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 107 atg tat ccg gat tta aaa gga aaa gtc gtc gct att aca gga gct gct      48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80
```

| | | |
|---|---|---|
| aag gag ttc ggc aca ctc gat att atg att aat aat gcc ggt ctt gaa<br>Lys Glu Phe Gly Thr Leu Asp Ile Met Ile Asn Asn Ala Gly Leu Glu<br>85 90 95 | | 288 |
| aat cct gtg cca tct cac gaa atg ccg ctc aag gat tgg gat aaa gtc<br>Asn Pro Val Pro Ser His Glu Met Pro Leu Lys Asp Trp Asp Lys Val<br>100 105 110 | | 336 |
| atc ggc acg aac tta acg ggt gcc ttt tta gga agc cgt gaa gcg att<br>Ile Gly Thr Asn Leu Thr Gly Ala Phe Leu Gly Ser Arg Glu Ala Ile<br>115 120 125 | | 384 |
| aaa tat ttc gta gaa aac gat atc aag gga aat gtc att aac atg tcc<br>Lys Tyr Phe Val Glu Asn Asp Ile Lys Gly Asn Val Ile Asn Met Ser<br>130 135 140 | | 432 |
| agt gtg cac gaa gtg att cct tgg ccg tta ttt gtc cac tat gcg gca<br>Ser Val His Glu Val Ile Pro Trp Pro Leu Phe Val His Tyr Ala Ala<br>145 150 155 160 | | 480 |
| agt aaa ggc ggg atg aag ctg atg acg gaa aca tta gcg ttg gaa tac<br>Ser Lys Gly Gly Met Lys Leu Met Thr Glu Thr Leu Ala Leu Glu Tyr<br>165 170 175 | | 528 |
| gcg ccg aag ggc att cgc gtc aat aat att ggg cca ggt gcg atc aac<br>Ala Pro Lys Gly Ile Arg Val Asn Asn Ile Gly Pro Gly Ala Ile Asn<br>180 185 190 | | 576 |
| acg acg atc aat gct ttg aaa ttt gct gac cct aaa cag aaa gct gat<br>Thr Thr Ile Asn Ala Leu Lys Phe Ala Asp Pro Lys Gln Lys Ala Asp<br>195 200 205 | | 624 |
| gta gaa agc atg att cca atg gga tat atc ggc gaa ccg gag gag atc<br>Val Glu Ser Met Ile Pro Met Gly Tyr Ile Gly Glu Pro Glu Glu Ile<br>210 215 220 | | 672 |
| gcc gca gta gca gcc tgg ctt gct tcg aag gaa gcc agc tac gtc aca<br>Ala Ala Val Ala Ala Trp Leu Ala Ser Lys Glu Ala Ser Tyr Val Thr<br>225 230 235 240 | | 720 |
| ggc atc acg tta ttc gcg gac ggc ggt atg aca caa tat cct tca ttc<br>Gly Ile Thr Leu Phe Ala Asp Gly Gly Met Thr Gln Tyr Pro Ser Phe<br>245 250 255 | | 768 |
| cag gca ggc cgc ggt taa<br>Gln Ala Gly Arg Gly<br>260 | | 786 |

<210> SEQ ID NO 108
<211> LENGTH: 261
<212> TYPE: PRT
<213> ORGANISM: Artificial
<220> FEATURE:
<223> OTHER INFORMATION: derived from bacillus

<400> SEQUENCE: 108

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

-continued

```
Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Leu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

```
<210> SEQ ID NO 109
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 109
```

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
```

```
Lys Tyr Phe Val Glu Asn Asp Ile Lys Gly Asn Val Ile Asn Met Ser
            130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat      624
Thr Thr Ile Asn Ala Glu Lys Phe Ala Asp Pro Lys Gln Lys Ala Asp
        195                 200                 205 gta gaa agc atg att cca atg gga tat atc gct gaa ccg gag gag atc      672
Val Glu Ser Met Ile Pro Met Gly Tyr Ile Ala Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 110
<211> LENGTH: 261
<212> TYPE: PRT
<213> ORGANISM: Artificial
<220> FEATURE:
<223> OTHER INFORMATION: derived from bacillus

<400> SEQUENCE: 110

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
```

-continued

```
                  180                 185                 190
Thr Thr Ile Asn Ala Glu Lys Phe Ala Asp Pro Lys Gln Lys Ala Asp
        195                 200                 205

Val Glu Ser Met Ile Pro Met Gly Tyr Ile Ala Glu Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 111
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 111 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                  10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
    50                  55                  60 gat gtc acg aat gag gaa gat gta aaa aat atc gtg caa acg gca att      240
Asp Val Thr Asn Glu Glu Asp Val Lys Asn Ile Val Gln Thr Ala Ile
65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
```

```
                   180                 185                 190
acg acg atc aat gct gag aaa ttt gct aat cct aaa cag aaa gct gat    624
Thr Thr Ile Asn Ala Glu Lys Phe Ala Asn Pro Lys Gln Lys Ala Asp
        195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa                                            786
Gln Ala Gly Arg Gly
                260
```

<210> SEQ ID NO 112
<211> LENGTH: 261
<212> TYPE: PRT
<213> ORGANISM: Artificial
<220> FEATURE:
<223> OTHER INFORMATION: derived from bacillus

<400> SEQUENCE: 112

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Gln Gly
        50                  55                  60

Asp Val Thr Asn Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asn Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255
```

```
Gln Ala Gly Arg Gly
        260

<210> SEQ ID NO 113
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 113 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat gct gag aaa atg gct gac cct aaa cag aaa gct gat     624
Thr Thr Ile Asn Ala Glu Lys Met Ala Asp Pro Lys Gln Lys Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240
```

```
ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
            245                 250                 255 cag gca ggc cgc ggt taa                                              786
Gln Ala Gly Arg Gly
        260

<210> SEQ ID NO 114
<211> LENGTH: 261
<212> TYPE: PRT
<213> ORGANISM: Artificial
<220> FEATURE:
<223> OTHER INFORMATION: derived from bacillus

<400> SEQUENCE: 114

Met Tyr Pro Asp Leu Lys Gly Lys Val Val Ala Ile Thr Gly Ala Ala
1               5                  10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Met Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 115
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
```

<223> OTHER INFORMATION: based upon B. subtilis GDH backbone
<220> FEATURE:
<221> NAME/KEY: CDS
<222> LOCATION: (1)..(786)

<400> SEQUENCE: 115

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |

| tca | ggg | ctc | gga | aag | gcg | atg | gcc | att | cgc | ttc | ggc | aag | gag | cag | gca | 96 |
|---|---|---|---|---|---|---|---|---|---|---|---|---|---|---|---|---|
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |

| aaa | gtg | gtt | atc | aac | tat | tat | agt | aat | aaa | caa | gat | ccg | aac | gag | gta | 144 |
|---|---|---|---|---|---|---|---|---|---|---|---|---|---|---|---|---|
| Lys | Val | Val | Ile | Asn | Tyr | Tyr | Ser | Asn | Lys | Gln | Asp | Pro | Asn | Glu | Val | |
| | | | 35 | | | | | 40 | | | | | 45 | | | |

| aaa | gaa | gag | gtc | atc | aag | gcg | ggc | ggt | gaa | gct | gtt | gtc | gtc | caa | gga | 192 |
|---|---|---|---|---|---|---|---|---|---|---|---|---|---|---|---|---|
| Lys | Glu | Glu | Val | Ile | Lys | Ala | Gly | Gly | Glu | Ala | Val | Val | Val | Gln | Gly | |
| | 50 | | | | | 55 | | | | | 60 | | | | | |

| gat | gtc | acg | aaa | gag | gaa | gat | gta | aaa | aat | atc | gtg | caa | acg | gca | att | 240 |
|---|---|---|---|---|---|---|---|---|---|---|---|---|---|---|---|---|
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |

| aag | gag | ttc | ggc | aca | ctc | gat | att | atg | att | aat | aat | gcc | ggt | ctt | gaa | 288 |
|---|---|---|---|---|---|---|---|---|---|---|---|---|---|---|---|---|
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |

| aat | cct | gtg | cca | tct | cac | gaa | atg | ccg | ctc | aag | gat | tgg | gat | aaa | gtc | 336 |
|---|---|---|---|---|---|---|---|---|---|---|---|---|---|---|---|---|
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |

| atc | ggc | acg | aac | tta | acg | ggt | gcc | ttt | tta | gga | agc | cgt | gaa | gcg | att | 384 |
|---|---|---|---|---|---|---|---|---|---|---|---|---|---|---|---|---|
| Ile | Gly | Thr | Asn | Leu | Thr | Gly | Ala | Phe | Leu | Gly | Ser | Arg | Glu | Ala | Ile | |
| | | | 115 | | | | | 120 | | | | | 125 | | | |

| aaa | tat | ttc | gta | gaa | aac | gat | atc | aag | gga | aat | gtc | att | aac | atg | tcc | 432 |
|---|---|---|---|---|---|---|---|---|---|---|---|---|---|---|---|---|
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |

| agt | gtg | cac | gaa | gtg | att | cct | tgg | ccg | tta | ttt | gtc | cac | tat | gcg | gca | 480 |
|---|---|---|---|---|---|---|---|---|---|---|---|---|---|---|---|---|
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |

| agt | aaa | ggc | ggg | atg | aag | ctg | atg | aca | gaa | aca | tta | gcg | ttg | gaa | tac | 528 |
|---|---|---|---|---|---|---|---|---|---|---|---|---|---|---|---|---|
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |

| gcg | ccg | aag | ggc | att | cgc | gtc | aat | aat | att | ggg | cca | ggt | gcg | atc | aac | 576 |
|---|---|---|---|---|---|---|---|---|---|---|---|---|---|---|---|---|
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |

| acg | acg | atc | aat | gct | gag | aaa | ttt | gct | gac | cct | aaa | cag | aaa | gct | gat | 624 |
|---|---|---|---|---|---|---|---|---|---|---|---|---|---|---|---|---|
| Thr | Thr | Ile | Asn | Ala | Glu | Lys | Phe | Ala | Asp | Pro | Lys | Gln | Lys | Ala | Asp | |
| | | | 195 | | | | | 200 | | | | | 205 | | | |

| gta | gaa | ggt | atg | att | cca | atg | gga | tat | atc | ggc | gaa | ccg | gag | gag | atc | 672 |
|---|---|---|---|---|---|---|---|---|---|---|---|---|---|---|---|---|
| Val | Glu | Gly | Met | Ile | Pro | Met | Gly | Tyr | Ile | Gly | Glu | Pro | Glu | Glu | Ile | |
| | 210 | | | | | 215 | | | | | 220 | | | | | |

| gcc | gca | gta | gca | gcc | tgg | ctt | gct | tcg | aag | gaa | gcc | agc | tac | gtc | aca | 720 |
|---|---|---|---|---|---|---|---|---|---|---|---|---|---|---|---|---|
| Ala | Ala | Val | Ala | Ala | Trp | Leu | Ala | Ser | Lys | Glu | Ala | Ser | Tyr | Val | Thr | |
| 225 | | | | | 230 | | | | | 235 | | | | | 240 | |

| ggc | atc | acg | tta | ttc | gcg | gac | ggc | ggt | atg | aca | caa | tat | cct | tca | ttc | 768 |
|---|---|---|---|---|---|---|---|---|---|---|---|---|---|---|---|---|
| Gly | Ile | Thr | Leu | Phe | Ala | Asp | Gly | Gly | Met | Thr | Gln | Tyr | Pro | Ser | Phe | |
| | | | | 245 | | | | | 250 | | | | | 255 | | |

| cag | gca | ggc | cgc | ggt | taa | | | | | | | | | | | 786 |
|---|---|---|---|---|---|---|---|---|---|---|---|---|---|---|---|---|
| Gln | Ala | Gly | Arg | Gly | | | | | | | | | | | | |
| | | 260 | | | | | | | | | | | | | | |

<210> SEQ ID NO 116
<211> LENGTH: 261
<212> TYPE: PRT

<213> ORGANISM: Artificial
<220> FEATURE:
<223> OTHER INFORMATION: derived from bacillus

<400> SEQUENCE: 116

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
        195                 200                 205

Val Glu Gly Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 117
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 117 atg tat ccg gat tta aaa gga aaa gtc gtc gct att aca gga gct gct    48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca    96
Ser Gly Leu Gly Lys Ala Met Ala Ile Arg Phe Gly Lys Glu Gln Ala -continued

```
                    20                  25                  30
aaa gtg gtt atc aac tat tat agt aat aaa caa gat ccg aac gag gta    144
Lys Val Val Ile Asn Tyr Tyr Ser Asn Lys Gln Asp Pro Asn Glu Val
             35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa    288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac    528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
            180                 185                 190 acg acg atc aat aag gag aaa ttt gct gac cct aaa cag aaa gct gat    624
Thr Thr Ile Asn Lys Glu Lys Phe Ala Asp Pro Lys Gln Lys Ala Asp
            195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa                                            786
Gln Ala Gly Arg Gly
            260

<210> SEQ ID NO 118
<211> LENGTH: 261
<212> TYPE: PRT
<213> ORGANISM: Artificial
<220> FEATURE:
<223> OTHER INFORMATION: derived from bacillus

<400> SEQUENCE: 118

Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
```

-continued

```
                35                  40                  45
Lys Glu Glu Val Ile Lys Ala Gly Gly Glu Ala Val Val Gln Gly
 50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
                115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
                180                 185                 190

Thr Thr Ile Asn Lys Glu Lys Phe Ala Asp Pro Lys Gln Lys Ala Asp
                195                 200                 205

Val Glu Ser Met Ile Pro Met Gly Tyr Ile Gly Glu Pro Glu Glu Ile
                210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260

<210> SEQ ID NO 119
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 119 atg tat ccg gat tta aaa gga aaa gtc gtc gct att aca gga gct gct        48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac aag gta      144
Lys Val Val Ile Asn Tyr Tyr Ser Asn Lys Gln Asp Pro Asn Lys Val
            35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
65                  70                  75                  80
```

```
aag gag ttc ggc aca ctc gat att atg att aat aat gcc ggt ctt gaa      288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat gct gag aaa ttt ggg gac cct aaa cag aaa gct gat      624
Thr Thr Ile Asn Ala Glu Lys Phe Gly Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 120
<211> LENGTH: 261
<212> TYPE: PRT
<213> ORGANISM: Artificial
<220> FEATURE:
<223> OTHER INFORMATION: derived from bacillus

<400> SEQUENCE: 120

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Lys Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110
```

```
Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Gly Asp Pro Lys Gln Lys Ala Asp
        195                 200                 205

Val Glu Ser Met Ile Pro Met Gly Tyr Ile Gly Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 121
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 121 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125
```

-continued

| | | |
|---|---|---|
| aaa tat ttc gta gaa aac gat atc aag gga aat gtc att aac atg tcc<br>Lys Tyr Phe Val Glu Asn Asp Ile Lys Gly Asn Val Ile Asn Met Ser<br>130                         135                              140 | 432 |
| agt gtg cac gaa gtg att cct tgg ccg tta ttt gtc cac tat gcg gca<br>Ser Val His Glu Val Ile Pro Trp Pro Leu Phe Val His Tyr Ala Ala<br>145                         150                         155                         160 | 480 |
| agt aaa ggc ggg atg aag ctg atg aca gaa aca tta gcg ttg gaa tac<br>Ser Lys Gly Gly Met Lys Leu Met Thr Glu Thr Leu Ala Leu Glu Tyr<br>                       165                         170                         175 | 528 |
| gcg ccg aag ggc att cgc gtc aat aat att ggg cca ggt gcg atc aac<br>Ala Pro Lys Gly Ile Arg Val Asn Asn Ile Gly Pro Gly Ala Ile Asn<br>         180                          185                         190 | 576 |
| acg acg atc aat gct gag aaa ttt gct gac cct cag cag aaa gct gat<br>Thr Thr Ile Asn Ala Glu Lys Phe Ala Asp Pro Gln Gln Lys Ala Asp<br>         195                          200                         205 | 624 |
| gta gaa agc atg att cca atg gga tat atc ggc gaa ccg gag gag atc<br>Val Glu Ser Met Ile Pro Met Gly Tyr Ile Gly Glu Pro Glu Glu Ile<br>210                         215                             220 | 672 |
| gcc gca gta gca gcc tgg ctt gct tcg aag gaa gcc agc tac gtc aca<br>Ala Ala Val Ala Ala Trp Leu Ala Ser Lys Glu Ala Ser Tyr Val Thr<br>225                         230                         235                         240 | 720 |
| ggc atc acg tta ttc gcg gac ggc ggt atg aca caa tat cct tca ttc<br>Gly Ile Thr Leu Phe Ala Asp Gly Gly Met Thr Gln Tyr Pro Ser Phe<br>                       245                         250                         255 | 768 |
| cag gca ggc cgc ggt taa<br>Gln Ala Gly Arg Gly<br>         260 | 786 |

<210> SEQ ID NO 122
<211> LENGTH: 261
<212> TYPE: PRT
<213> ORGANISM: Artificial
<220> FEATURE:
<223> OTHER INFORMATION: derived from bacillus

<400> SEQUENCE: 122

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

```
Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Gln Gln Lys Ala Asp
                195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 123
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 123
```

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |

```
tca ggg ctc gga aag gcg atg gcc att cgc ttc ggc aag gag cag gca     96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta    144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa    288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac    528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
```

```
Ala Pro Lys Gly Ile Arg Val Asn Asn Ile Gly Pro Gly Ala Ile Asn
            180                 185                 190 acg acg atc aat gct gag aaa ttt agt gac cct aaa cag aaa gct gat      624
Thr Thr Ile Asn Ala Glu Lys Phe Ser Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 124
<211> LENGTH: 261
<212> TYPE: PRT
<213> ORGANISM: Artificial
<220> FEATURE:
<223> OTHER INFORMATION: derived from bacillus

<400> SEQUENCE: 124

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
            85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ser Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
```

Gln Ala Gly Arg Gly
        260

<210> SEQ ID NO 125
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 125

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | | 35 | | | | | 40 | | | | | 45 | | | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| | 50 | | | | | 55 | | | | | 60 | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| acg | acg | atc | aat | gct | gag | aaa | ttt | gct | gac | cct | act | cag | aaa | gct | gat | 624 |
| Thr | Thr | Ile | Asn | Ala | Glu | Lys | Phe | Ala | Asp | Pro | Thr | Gln | Lys | Ala | Asp | |
| | | 195 | | | | | 200 | | | | | 205 | | | | |
| gta | gaa | agc | atg | att | cca | atg | gga | tat | atc | ggc | gaa | ccg | gag | gag | atc | 672 |
| Val | Glu | Ser | Met | Ile | Pro | Met | Gly | Tyr | Ile | Gly | Glu | Pro | Glu | Glu | Ile | |
| | 210 | | | | | 215 | | | | | 220 | | | | | |
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr | |

```
                225                 230                 235                 240
ggc atc acg tta ttc gcg gac ggc ggt atg aca caa tat cct tca ttc              768
Gly Ile Thr Leu Phe Ala Asp Gly Gly Met Thr Gln Tyr Pro Ser Phe
                245                 250                 255 cag gca ggc cgc ggt taa                                                      786
Gln Ala Gly Arg Gly
        260
```

<210> SEQ ID NO 126
<211> LENGTH: 261
<212> TYPE: PRT
<213> ORGANISM: Artificial
<220> FEATURE:
<223> OTHER INFORMATION: derived from bacillus

<400> SEQUENCE: 126

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Thr Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 127
<211> LENGTH: 786
<212> TYPE: DNA
<213> ORGANISM: Artificial
<220> FEATURE:
<223> OTHER INFORMATION: derived from bacillus
<220> FEATURE:

```
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 127
```

| | | | | | | | | | | | | | | | | |
|---|---|---|---|---|---|---|---|---|---|---|---|---|---|---|---|---|
| atg | tat | ccg | gat | tta | aaa | gga | aaa | gtc | gtc | gct | att | aca | gga | gct | gct | 48 |
| Met | Tyr | Pro | Asp | Leu | Lys | Gly | Lys | Val | Val | Ala | Ile | Thr | Gly | Ala | Ala | |
| 1 | | | | 5 | | | | | 10 | | | | | 15 | | |
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | | 20 | | | | | 25 | | | | | 30 | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | 35 | | | | | 40 | | | | | 45 | | | | | |
| aaa | gaa | gag | gtc | atc | agg | gcg | ggc | ggt | gaa | gct | gtt | gtc | gtc | caa | gga | 192 |
| Lys | Glu | Glu | Val | Ile | Arg | Ala | Gly | Gly | Glu | Ala | Val | Val | Val | Gln | Gly | |
| | 50 | | | | | 55 | | | | | 60 | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | | 70 | | | | | 75 | | | | | 80 | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| acg | acg | atc | aat | gct | gag | aaa | ttt | ttg | gac | cct | aaa | cag | aaa | gct | gat | 624 |
| Thr | Thr | Ile | Asn | Ala | Glu | Lys | Phe | Leu | Asp | Pro | Lys | Gln | Lys | Ala | Asp | |
| | | 195 | | | | | 200 | | | | | 205 | | | | |
| gta | gaa | agc | atg | att | cca | atg | gga | tat | atc | ggc | gaa | ccg | gag | gag | atc | 672 |
| Val | Glu | Ser | Met | Ile | Pro | Met | Gly | Tyr | Ile | Gly | Glu | Pro | Glu | Glu | Ile | |
| | 210 | | | | | 215 | | | | | 220 | | | | | |
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr | |
| 225 | | | | | 230 | | | | | 235 | | | | | 240 | |
| ggc | atc | acg | tta | ttc | gcg | gac | ggc | ggt | atg | aca | caa | tat | cct | tca | ttc | 768 |
| Gly | Ile | Thr | Leu | Phe | Ala | Asp | Gly | Gly | Met | Thr | Gln | Tyr | Pro | Ser | Phe | |
| | | | | 245 | | | | | 250 | | | | | 255 | | |
| cag | gca | ggc | cgc | ggt | taa | | | | | | | | | | | 786 |
| Gln | Ala | Gly | Arg | Gly | | | | | | | | | | | | |
| | | | 260 | | | | | | | | | | | | | |

```
<210> SEQ ID NO 128
<211> LENGTH: 261
```

```
<212> TYPE: PRT
<213> ORGANISM: Artificial
<220> FEATURE:
<223> OTHER INFORMATION: derived from bacillus

<400> SEQUENCE: 128

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Arg Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Leu Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 129
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 129 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
```

```
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat gct gag aaa ttt gct gac cct gaa cag aga gct gat      624
Thr Thr Ile Asn Ala Glu Lys Phe Ala Asp Pro Glu Gln Arg Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 130
<211> LENGTH: 261
<212> TYPE: PRT
<213> ORGANISM: Artificial
<220> FEATURE:
<223> OTHER INFORMATION: derived from bacillus

<400> SEQUENCE: 130

Met Tyr Pro Asp Leu Lys Gly Lys Val Val Ala Ile Thr Gly Ala Ala
1               5                  10                  15

Ser Gly Leu Gly Lys Ala Met Ala Ile Arg Phe Gly Lys Glu Gln Ala
            20                  25                  30
```

-continued

```
Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Gln Gly
 50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Glu Gln Arg Ala Asp
            195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 131
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 131 atg tat ccg gat tta aaa gga aaa gtc gtc gct att aca gga gct gct      48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75
```

```
aag gag ttc ggc aca ctc gat att atg att aat aat gcc ggt ctt gaa      288
Lys Glu Phe Gly Thr Leu Asp Ile Met Ile Asn Asn Ala Gly Leu Glu
             85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
        100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat aag gag aaa ttt gct gac cct aaa cag aaa gct gat      624
Thr Thr Ile Asn Lys Glu Lys Phe Ala Asp Pro Lys Gln Lys Ala Asp
        195                 200                 205 gta gaa agc atg att cca atg gga tat atc ggc caa ccg gag gag atc      672
Val Glu Ser Met Ile Pro Met Gly Tyr Ile Gly Gln Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 132
<211> LENGTH: 261
<212> TYPE: PRT
<213> ORGANISM: Artificial
<220> FEATURE:
<223> OTHER INFORMATION: derived from bacillus

<400> SEQUENCE: 132

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
```

```
                   100                 105                 110
Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Lys Gln Lys Ala Asp
            195                 200                 205

Val Glu Ser Met Ile Pro Met Gly Tyr Ile Gly Gln Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 133
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 133 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125
```

```
aaa tat ttc gta gaa aac gat atc aag gga aat gtc att aac atg tcc      432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat aag gag aaa ttt gct gac cct gaa cag aaa gct gat      624
Thr Thr Ile Asn Lys Glu Lys Phe Ala Asp Pro Glu Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 134
<211> LENGTH: 261
<212> TYPE: PRT
<213> ORGANISM: Artificial
<220> FEATURE:
<223> OTHER INFORMATION: derived from bacillus

<400> SEQUENCE: 134

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175
```

```
Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Lys Ala Asp
            195                 200                 205

Val Glu Ser Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 135
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 135 atg tat ccg gat tta aaa gga aaa gtc gtc gct att aca gga gct gct     48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca     96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta    144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa    288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
                100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
        130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac    528
Ser Lys Gly Gly Met Lys Leu Met Thr Glu Thr Leu Ala Leu Glu Tyr
                165                 170                 175
```

```
gcg ccg aag ggc att cgc gtc aat aat att ggg cca ggt gcg atc aac      576
Ala Pro Lys Gly Ile Arg Val Asn Asn Ile Gly Pro Gly Ala Ile Asn
        180                 185                 190 acg acg atc aat aag gag aaa ttt gct gac cct gaa cag aga gct gat      624
Thr Thr Ile Asn Lys Glu Lys Phe Ala Asp Pro Glu Gln Arg Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260

<210> SEQ ID NO 136
<211> LENGTH: 261
<212> TYPE: PRT
<213> ORGANISM: Artificial
<220> FEATURE:
<223> OTHER INFORMATION: derived from bacillus

<400> SEQUENCE: 136

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240
```

```
Gly Ile Thr Leu Phe Ala Asp Gly Gly Met Thr Gln Tyr Pro Ser Phe
                245                 250                 255

Gln Ala Gly Arg Gly
            260

<210> SEQ ID NO 137
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 137 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat gct gag aaa ttt gct gac cct gaa cag aga gct gat     624
Thr Thr Ile Asn Ala Glu Lys Phe Ala Asp Pro Glu Gln Arg Ala Asp
        195                 200                 205 gta gaa agc atg att cca atg gga tat atc ggc caa ccg gag gag atc     672
Val Glu Ser Met Ile Pro Met Gly Tyr Ile Gly Gln Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
```

```
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa                                             786
Gln Ala Gly Arg Gly
            260
```

<210> SEQ ID NO 138
<211> LENGTH: 261
<212> TYPE: PRT
<213> ORGANISM: Artificial
<220> FEATURE:
<223> OTHER INFORMATION: derived from bacillus

<400> SEQUENCE: 138

```
Met Tyr Pro Asp Leu Lys Gly Lys Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
                35                  40                  45

Lys Glu Glu Val Ile Lys Ala Gly Gly Glu Ala Val Val Val Gln Gly
50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Glu Gln Arg Ala Asp
    195                 200                 205

Val Glu Ser Met Ile Pro Met Gly Tyr Ile Gly Gln Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 139
<211> LENGTH: 786
<212> TYPE: DNA
<213> ORGANISM: Artificial
<220> FEATURE:
<223> OTHER INFORMATION: derived from bacillus

```
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 139 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat gct gag aaa ttt gct gac cct aat cag aaa gct gat     624
Thr Thr Ile Asn Ala Glu Lys Phe Ala Asp Pro Asn Gln Lys Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa                                             786
Gln Ala Gly Arg Gly
            260

<210> SEQ ID NO 140
```

<211> LENGTH: 261
<212> TYPE: PRT
<213> ORGANISM: Artificial
<220> FEATURE:
<223> OTHER INFORMATION: derived from bacillus

<400> SEQUENCE: 140

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Asn Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 141
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 141

```
atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15
```

```
tca ggg ctc gga aag gcg atg gcc att cgc ttc ggc aag gag cag gca      96
Ser Gly Leu Gly Lys Ala Met Ala Ile Arg Phe Gly Lys Glu Gln Ala
         20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
                 35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
                100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat gct gag aaa ttt gct gac cct aaa cag aaa gct gat     624
Thr Thr Ile Asn Ala Glu Lys Phe Ala Asp Pro Lys Gln Lys Ala Asp
        195                 200                 205 gta gaa agc atg att cca atg gga tat atc ggc caa ccg gag gag atc     672
Val Glu Ser Met Ile Pro Met Gly Tyr Ile Gly Gln Pro Glu Glu Ile
210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 142
<211> LENGTH: 261
<212> TYPE: PRT
<213> ORGANISM: Artificial
<220> FEATURE:
<223> OTHER INFORMATION: derived from bacillus

<400> SEQUENCE: 142

```
Met Tyr Pro Asp Leu Lys Gly Lys Val Val Ala Ile Thr Gly Ala Ala
  1               5                  10                  15

Ser Gly Leu Gly Lys Ala Met Ala Ile Arg Phe Gly Lys Glu Gln Ala
             20                  25                  30
```

```
Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Gln Gly
 50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Lys Gln Lys Ala Asp
            195                 200                 205

Val Glu Ser Met Ile Pro Met Gly Tyr Ile Gly Gln Pro Glu Glu Ile
            210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 143
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 143 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
 50                  55                  60 gat gtc acg aaa gag gaa gat gta aaa aat atc gtg caa acg gca att     240
```

| | | | | | | | | | | | | | | |
|---|---|---|---|---|---|---|---|---|---|---|---|---|---|---|
|Asp|Val|Thr|Lys|Glu|Glu|Asp|Val|Lys|Asn|Ile|Val|Gln|Thr|Ala|Ile|
|65| | | |70| | | |75| | | |80| |

```
aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
                115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
        130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat gct gag aaa ttt gct gac cct gat aat aaa gct gat      624
Thr Thr Ile Asn Ala Glu Lys Phe Ala Asp Pro Asp Asn Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
                260
```

```
<210> SEQ ID NO 144
<211> LENGTH: 261
<212> TYPE: PRT
<213> ORGANISM: Artificial
<220> FEATURE:
<223> OTHER INFORMATION: derived from bacillus

<400> SEQUENCE: 144
```

| | | | | | | | | | | | | | | |
|---|---|---|---|---|---|---|---|---|---|---|---|---|---|---|
|Met|Tyr|Pro|Asp|Leu|Lys|Gly|Lys|Val|Val|Ala|Ile|Thr|Gly|Ala|Ala|
|1| | | |5| | | |10| | | |15| |

| | | | | | | | | | | | | | | |
|---|---|---|---|---|---|---|---|---|---|---|---|---|---|---|
|Ser|Gly|Leu|Gly|Lys|Ala|Met|Ala|Ile|Arg|Phe|Gly|Lys|Glu|Gln|Ala|
| | | |20| | | |25| | | |30| | | |

| | | | | | | | | | | | | | | |
|---|---|---|---|---|---|---|---|---|---|---|---|---|---|---|
|Lys|Val|Val|Ile|Asn|Tyr|Tyr|Ser|Asn|Lys|Gln|Asp|Pro|Asn|Glu|Val|
| | |35| | | |40| | | |45| | | | |

| | | | | | | | | | | | | | | |
|---|---|---|---|---|---|---|---|---|---|---|---|---|---|---|
|Lys|Glu|Glu|Val|Ile|Lys|Ala|Gly|Gly|Glu|Ala|Val|Val|Gln|Gly|
| |50| | | |55| | | |60| | | | | |

| | | | | | | | | | | | | | | |
|---|---|---|---|---|---|---|---|---|---|---|---|---|---|---|
|Asp|Val|Thr|Lys|Glu|Glu|Asp|Val|Lys|Asn|Ile|Val|Gln|Thr|Ala|Ile|
|65| | | |70| | | |75| | | |80| |

| | | | | | | | | | | | | | | |
|---|---|---|---|---|---|---|---|---|---|---|---|---|---|---|
|Lys|Glu|Phe|Gly|Thr|Leu|Asp|Ile|Met|Ile|Asn|Asn|Ala|Gly|Leu|Glu|
| | | |85| | | |90| | | |95| | | |

```
Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Asp Asn Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 145
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 145 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca gga ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gat gta     144
Lys Val Val Ile Asn Tyr Tyr Ser Asn Lys Gln Asp Pro Asn Asp Val
        35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125
```

-continued

```
                    115                 120                     125
aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat aag gag aaa ttt gct gac cct gaa cag aga gct gat     624
Thr Thr Ile Asn Lys Glu Lys Phe Ala Asp Pro Glu Gln Arg Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa                                             786
Gln Ala Gly Arg Gly
            260
```

<210> SEQ ID NO 146
<211> LENGTH: 261
<212> TYPE: PRT
<213> ORGANISM: Artificial
<220> FEATURE:
<223> OTHER INFORMATION: derived from bacillus

<400> SEQUENCE: 146

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Asp Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
```

```
                   165                 170                 175
Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 147
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 147 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccc ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca       480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac       528
Ser Lys Gly Gly Met Lys Leu Met Thr Glu Thr Leu Ala Leu Glu Tyr
                165                 170                 175
```

```
gcg ccg aag ggc att cgc gtc aat aat att ggg cca ggt gcg atc aac      576
Ala Pro Lys Gly Ile Arg Val Asn Asn Ile Gly Pro Gly Ala Ile Asn
        180                 185                 190 acg acg atc aat aag gag aaa ttt gct gac cct gaa cag aga gct gat      624
Thr Thr Ile Asn Lys Glu Lys Phe Ala Asp Pro Glu Gln Arg Ala Asp
        195                 200                 205 gta gaa agc atg atc cca atg gga tat atc ggc gaa ccg gag gag atc      672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
        260
```

<210> SEQ ID NO 148
<211> LENGTH: 261
<212> TYPE: PRT
<213> ORGANISM: Artificial
<220> FEATURE:
<223> OTHER INFORMATION: derived from bacillus

<400> SEQUENCE: 148

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240
```

```
Gly Ile Thr Leu Phe Ala Asp Gly Gly Met Thr Gln Tyr Pro Ser Phe
            245                 250                 255

Gln Ala Gly Arg Gly
        260

<210> SEQ ID NO 149
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 149 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtt gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tac gcg gca       480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac       528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg acg atc aat gct gag aaa ttt gct gac cct gaa cag aga gct gat       624
Thr Thr Ile Asn Ala Glu Lys Phe Ala Asp Pro Glu Gln Arg Ala Asp
        195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
    210                 215                 220
```

```
gcc gca gta gca gcc tgg ctt gct tcg aag gaa gcc agc tat gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                245                 250                 255 cag gca ggc cgc ggt taa                                            786
Gln Ala Gly Arg Gly
            260
```

<210> SEQ ID NO 150
<211> LENGTH: 261
<212> TYPE: PRT
<213> ORGANISM: Artificial
<220> FEATURE:
<223> OTHER INFORMATION: derived from bacillus

<400> SEQUENCE: 150

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 151
<211> LENGTH: 786
<212> TYPE: DNA
<213> ORGANISM: Artificial
<220> FEATURE:

<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 151

```
atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
                20                  25                  30 aaa gtg gtt atc aac tat tat agt aat aag caa gat ccg aac gag gta     144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
                100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
            115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
        130                 135                 140 agt gtg cac gaa gta att cct tgg ccg tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac     576
Ala Pro Lys Gly Ile Arg Val Asn Asn Ile Gly Pro Gly Ala Ile Asn
            180                 185                 190 acg acg atc aat aag gag aaa ttt gct gac cct gaa cag aga gca gat     624
Thr Thr Ile Asn Lys Glu Lys Phe Ala Asp Pro Glu Gln Arg Ala Asp
        195                 200                 205 gta gaa agc atg att cca atg gga tat atc ggc gaa ccg gag gag atc     672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca     720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc     768
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 152
<211> LENGTH: 261
<212> TYPE: PRT
<213> ORGANISM: Artificial
<220> FEATURE:
<223> OTHER INFORMATION: derived from bacillus

<400> SEQUENCE: 152

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 153
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 153

```
atg tat ccg gat tta aaa gga aaa gtc gtc gct att aca gga gct gct     48
Met Tyr Pro Asp Leu Lys Gly Lys Val Val Ala Ile Thr Gly Ala Ala
1               5                   10                  15
```

| | | | | | | | | | | | | | | | | |
|---|---|---|---|---|---|---|---|---|---|---|---|---|---|---|---|---|
| tca | ggg | ctc | gga | aag | gcg | atg | gcc | att | cgc | ttc | ggc | aag | gag | cag | gca | 96 |
| Ser | Gly | Leu | Gly | Lys | Ala | Met | Ala | Ile | Arg | Phe | Gly | Lys | Glu | Gln | Ala | |
| | | 20 | | | | | 25 | | | | | 30 | | | | |
| aaa | gtg | gtt | atc | aac | tat | tat | agt | aat | aaa | caa | gat | ccg | aac | gag | gta | 144 |
| Lys | Val | Val | Ile | Asn | Tyr | Tyr | Ser | Asn | Lys | Gln | Asp | Pro | Asn | Glu | Val | |
| | 35 | | | | | 40 | | | | | 45 | | | | | |
| aaa | gaa | gag | gtc | atc | aag | gcg | ggc | ggt | gaa | gct | gtt | gtc | gtc | caa | gga | 192 |
| Lys | Glu | Glu | Val | Ile | Lys | Ala | Gly | Gly | Glu | Ala | Val | Val | Val | Gln | Gly | |
| 50 | | | | | 55 | | | | | 60 | | | | | | |
| gat | gtc | acg | aaa | gag | gaa | gat | gta | aaa | aat | atc | gtg | caa | acg | gca | att | 240 |
| Asp | Val | Thr | Lys | Glu | Glu | Asp | Val | Lys | Asn | Ile | Val | Gln | Thr | Ala | Ile | |
| 65 | | | | 70 | | | | | 75 | | | | | 80 | | |
| aag | gag | ttc | ggc | aca | ctc | gat | att | atg | att | aat | aat | gcc | ggt | ctt | gaa | 288 |
| Lys | Glu | Phe | Gly | Thr | Leu | Asp | Ile | Met | Ile | Asn | Asn | Ala | Gly | Leu | Glu | |
| | | | | 85 | | | | | 90 | | | | | 95 | | |
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val | |
| | | | 100 | | | | | 105 | | | | | 110 | | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile | |
| | | 115 | | | | | 120 | | | | | 125 | | | | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser | |
| | 130 | | | | | 135 | | | | | 140 | | | | | |
| agt | gtg | cac | gaa | gta | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala | |
| 145 | | | | | 150 | | | | | 155 | | | | | 160 | |
| agt | aaa | ggc | ggg | atg | aag | ctg | atg | aca | gaa | aca | tta | gcg | ttg | gaa | tac | 528 |
| Ser | Lys | Gly | Gly | Met | Lys | Leu | Met | Thr | Glu | Thr | Leu | Ala | Leu | Glu | Tyr | |
| | | | | 165 | | | | | 170 | | | | | 175 | | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn | |
| | | | 180 | | | | | 185 | | | | | 190 | | | |
| acg | acg | atc | aat | aag | gag | aaa | ttt | gct | gac | gat | aaa | cag | aaa | gct | gat | 624 |
| Thr | Thr | Ile | Asn | Lys | Glu | Lys | Phe | Ala | Asp | Asp | Lys | Gln | Lys | Ala | Asp | |
| | | 195 | | | | | 200 | | | | | 205 | | | | |
| gta | gaa | agc | atg | att | cca | atg | gga | tat | atc | ggc | gaa | ccg | gag | gag | atc | 672 |
| Val | Glu | Ser | Met | Ile | Pro | Met | Gly | Tyr | Ile | Gly | Glu | Pro | Glu | Glu | Ile | |
| | 210 | | | | | 215 | | | | | 220 | | | | | |
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr | |
| 225 | | | | | 230 | | | | | 235 | | | | | 240 | |
| ggc | atc | acg | tta | ttc | gcg | gac | ggc | ggt | atg | aca | caa | tat | cct | tca | ttc | 768 |
| Gly | Ile | Thr | Leu | Phe | Ala | Asp | Gly | Gly | Met | Thr | Gln | Tyr | Pro | Ser | Phe | |
| | | | | 245 | | | | | 250 | | | | | 255 | | |
| cag | gca | ggc | cgc | ggt | taa | | | | | | | | | | | 786 |
| Gln | Ala | Gly | Arg | Gly | | | | | | | | | | | | |
| | | | | 260 | | | | | | | | | | | | |

<210> SEQ ID NO 154
<211> LENGTH: 261
<212> TYPE: PRT
<213> ORGANISM: Artificial
<220> FEATURE:
<223> OTHER INFORMATION: derived from bacillus

<400> SEQUENCE: 154

| Met | Tyr | Pro | Asp | Leu | Lys | Gly | Lys | Val | Val | Ala | Ile | Thr | Gly | Ala | Ala |
|---|---|---|---|---|---|---|---|---|---|---|---|---|---|---|---|
| 1 | | | | 5 | | | | | 10 | | | | | 15 | |

| Ser | Gly | Leu | Gly | Lys | Ala | Met | Ala | Ile | Arg | Phe | Gly | Lys | Glu | Gln | Ala |
|---|---|---|---|---|---|---|---|---|---|---|---|---|---|---|---|

```
                 20                  25                  30
Lys Val Val Ile Asn Tyr Tyr Ser Asn Lys Gln Asp Pro Asn Glu Val
             35                  40                  45

Lys Glu Glu Val Ile Lys Ala Gly Gly Glu Ala Val Val Val Gln Gly
         50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Asp Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 155
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 155 atg tat ccg gat tta aaa gga aaa gtc gtc gct att aca gga gct gct     48
Met Tyr Pro Asp Leu Lys Gly Lys Val Val Ala Ile Thr Gly Ala Ala
 1               5                  10                  15 tca ggg ctc gga aag gcg atg gcc att cgc ttc ggc aag gag cag gca     96
Ser Gly Leu Gly Lys Ala Met Ala Ile Arg Phe Gly Lys Glu Gln Ala
             20                  25                  30 aaa gtg gtt atc aac tat tat agt aat aaa caa gat ccg aac gag gta    144
Lys Val Val Ile Asn Tyr Tyr Ser Asn Lys Gln Asp Pro Asn Glu Val
         35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
     50                  55                  60
```

```
gat gtc acg aaa gag gaa gat gta aaa aat atc gtg caa acg gca att    240
Asp Val Thr Lys Glu Glu Asp Val Lys Asn Ile Val Gln Thr Ala Ile
 65              70                  75                  80 aag gag ttc ggc aca ctc gat att atg att aat aat gcc ggt ctt gaa    288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
             100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
             115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
         130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tat    528
Ser Lys Gly Gly Met Lys Leu Met Thr Glu Thr Leu Ala Leu Glu Tyr
                 165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
             180                 185                 190 acg acg atc aat gct gag aaa ttt gct gac gat aaa cag aaa gct gat    624
Thr Thr Ile Asn Ala Glu Lys Phe Ala Asp Asp Lys Gln Lys Ala Asp
             195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
         210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
                 245                 250                 255 cag gca ggc cgc ggt taa                                            786
Gln Ala Gly Arg Gly
             260

<210> SEQ ID NO 156
<211> LENGTH: 261
<212> TYPE: PRT
<213> ORGANISM: Artificial
<220> FEATURE:
<223> OTHER INFORMATION: derived from bacillus

<400> SEQUENCE: 156

Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
                 20                  25                  30

Lys Val Val Ile Asn Tyr Tyr Ser Asn Lys Gln Asp Pro Asn Glu Val
             35                  40                  45

Lys Glu Glu Val Ile Lys Ala Gly Gly Glu Ala Val Val Gln Gly
         50                  55                  60

Asp Val Thr Lys Glu Glu Asp Val Lys Asn Ile Val Gln Thr Ala Ile
 65              70                  75                  80

Lys Glu Phe Gly Thr Leu Asp Ile Met Ile Asn Asn Ala Gly Leu Glu
                 85                  90                  95
```

```
Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Asp Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 157
<211> LENGTH: 786
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(786)

<400> SEQUENCE: 157 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc cga gga     192
Lys Glu Glu Val Ile Lys Ala Gly Gly Glu Ala Val Val Val Arg Gly
    50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
```

```
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac    528
Ser Lys Gly Gly Met Lys Leu Met Thr Glu Thr Leu Ala Leu Glu Tyr
            165                 170                 175 gcg ccg aag ggc att cgc gtc aat aat att ggg cca ggt gcg atc aac    576
Ala Pro Lys Gly Ile Arg Val Asn Asn Ile Gly Pro Gly Ala Ile Asn
        180                 185                 190 acg acg atc aat gct gag aaa ttt gct gac cct gaa cag aga gct gat    624
Thr Thr Ile Asn Ala Glu Lys Phe Ala Asp Pro Glu Gln Arg Ala Asp
    195                 200                 205 gta gaa agc atg att cca atg gga tat atc ggc gaa ccg gag gag atc    672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca    720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc    768
Gly Ile Thr Leu Phe Ala Asp Gly Gly Met Thr Gln Tyr Pro Ser Phe
            245                 250                 255 cag gca ggc cgc ggt taa                                            786
Gln Ala Gly Arg Gly
        260
```

<210> SEQ ID NO 158
<211> LENGTH: 261
<212> TYPE: PRT
<213> ORGANISM: Artificial
<220> FEATURE:
<223> OTHER INFORMATION: derived from bacillus

<400> SEQUENCE: 158

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Arg Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160
```

```
Ser Lys Gly Gly Met Lys Leu Met Thr Glu Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Thr Ile Asn Ala Glu Lys Phe Ala Asp Pro Glu Gln Arg Ala Asp
            195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 159
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 159 atg tat ccg gat tta aaa gga aaa gtc gtc gct att aca gga gct gct      48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca      96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta     144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga     192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att     240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa     288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc     336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att     384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc     432
Lys Tyr Phe Val Glu Asn Asp Ile Lys Gly Asn Val Ile Asn Met Ser
    130                 135                 140 agt gtg cac gaa gtg att cct tgg cca tta ttt gtc cac tat gcg gca     480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac     528
Ser Lys Gly Gly Met Lys Leu Met Thr Glu Thr Leu Ala Leu Glu Tyr
                165                 170                 175
```

```
                    165                 170                 175
gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg acg atc aat aag gag aaa ttt gct gac cct gaa cag aga gct gat       624
Thr Thr Ile Asn Lys Glu Lys Phe Ala Asp Pro Glu Gln Arg Ala Asp
            195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca       720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc       768
Gly Ile Thr Leu Phe Ala Asp Gly Gly Met Thr Gln Tyr Pro Ser Phe
                245                 250                 255 cag gca ggc cgc ggt taa tga                                           789
Gln Ala Gly Arg Gly
                260
```

<210> SEQ ID NO 160
<211> LENGTH: 261
<212> TYPE: PRT
<213> ORGANISM: Artificial
<220> FEATURE:
<223> OTHER INFORMATION: derived from bacillus

<400> SEQUENCE: 160

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
```

```
                225                 230                 235                 240
        Gly Ile Thr Leu Phe Ala Asp Gly Gly Met Thr Gln Tyr Pro Ser Phe
                        245                 250                 255

Gln Ala Gly Arg Gly
                    260

<210> SEQ ID NO 161
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 161 atg tat ccg gat tta aaa gga aaa gtc gtc gct att aca gga gct act        48
Met Tyr Pro Asp Leu Lys Gly Lys Val Val Ala Ile Thr Gly Ala Thr
1               5                   10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg cca tta ttt gtc cac tat gcg gca       480
Ser Val His Glu Val Ile Pro Trp Pro Leu Phe Val His Tyr Ala Ala
145                 150                 155                 160 agt aaa ggc ggg atg aag ctg atg aca aaa aca tta gcg ttg gaa tac       528
Ser Lys Gly Gly Met Lys Leu Met Thr Lys Thr Leu Ala Leu Glu Tyr
                165                 170                 175 gcg ccg aag ggc att cgc gtc aat aat att ggg cca ggt gcg atc aac       576
Ala Pro Lys Gly Ile Arg Val Asn Asn Ile Gly Pro Gly Ala Ile Asn
            180                 185                 190 acg acg atc aat aag gag aaa ttt gct gac cct gaa cag aga gct gat       624
Thr Thr Ile Asn Lys Glu Lys Phe Ala Asp Pro Glu Gln Arg Ala Asp
        195                 200                 205 gta gaa agc atg att cca atg gga tat atc ggc gaa ccg gag gag atc       672
Val Glu Ser Met Ile Pro Met Gly Tyr Ile Gly Glu Pro Glu Glu Ile
    210                 215                 220
```

```
gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt taa tga                                            789
Gln Ala Gly Arg Gly
            260

<210> SEQ ID NO 162
<211> LENGTH: 261
<212> TYPE: PRT
<213> ORGANISM: Artificial
<220> FEATURE:
<223> OTHER INFORMATION: derived from bacillus

<400> SEQUENCE: 162

Met Tyr Pro Asp Leu Lys Gly Lys Val Val Ala Ile Thr Gly Ala Thr
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 163
<211> LENGTH: 789
<212> TYPE: DNA
<213> ORGANISM: Artificial
```

```
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 163 atg tat ccg gat tta aaa gga aaa gtc gtc gct att aca gga gct gct        48
Met Tyr Pro Asp Leu Lys Gly Lys Val Val Ala Ile Thr Gly Ala Ala
1               5                  10                  15 tca ggg ctc gga aag gcg atg gcc att cgc ttc ggc aag gag cag gca        96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta       144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga       192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att       240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa       288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc       336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att       384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc       432
Lys Tyr Phe Val Glu Asn Asp Ile Lys Gly Asn Val Ile Asn Met Ser
    130                 135                 140 agt gtg cac gaa gtg att cct tgg cca tta ttt gtc cac tat gcg gca       480
Ser Val His Glu Val Ile Pro Trp Pro Leu Phe Val His Tyr Ala Ala
145                 150                 155                 160 agt aaa ggt ggg atg aag ctg atg aca aaa aca tta gcg ttg gaa tac       528
Ser Lys Gly Gly Met Lys Leu Met Thr Lys Thr Leu Ala Leu Glu Tyr
                165                 170                 175 gcg ccg aag ggc att cgc gtc aat aat att ggg cca ggt gcg atc aat       576
Ala Pro Lys Gly Ile Arg Val Asn Asn Ile Gly Pro Gly Ala Ile Asn
            180                 185                 190 acg acg atc aat aag gag aaa ttt gct gac cct gaa cag aga gct gat       624
Thr Thr Ile Asn Lys Glu Lys Phe Ala Asp Pro Glu Gln Arg Ala Asp
        195                 200                 205 gta gaa agc atg att cca atg gga tat atc ggc gaa ccg gat gag atc       672
Val Glu Ser Met Ile Pro Met Gly Tyr Ile Gly Glu Pro Asp Glu Ile
    210                 215                 220 gcc gca gta gca gcc tgg ctt gct tcg aag gaa gcc tgc tac gtc aca       720
Ala Ala Val Ala Ala Trp Leu Ala Ser Lys Glu Ala Cys Tyr Val Thr
225                 230                 235                 240 ggc atc acg tta ttc gcg gac ggc ggt atg aca caa tat cct tca ttc       768
Gly Ile Thr Leu Phe Ala Asp Gly Gly Met Thr Gln Tyr Pro Ser Phe
                245                 250                 255 cag gca ggc cgc ggt taa tga                                           789
Gln Ala Gly Arg Gly
            260
```

<210> SEQ ID NO 164
<211> LENGTH: 261
<212> TYPE: PRT
<213> ORGANISM: Artificial
<220> FEATURE:
<223> OTHER INFORMATION: derived from bacillus

<400> SEQUENCE: 164

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Met Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
        195                 200                 205

Val Glu Ser Met Ile Pro Met Gly Tyr Ile Gly Glu Pro Asp Glu Ile
    210                 215                 220

Ala Ala Val Ala Ala Trp Leu Ala Ser Lys Glu Ala Cys Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 165
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 165 atg tat ccg gat tta aaa gga aaa gtc gtc gct att aca gga gct gct      48
Met Tyr Pro Asp Leu Lys Gly Lys Val Val Ala Ile Thr Gly Ala Ala

| | | |
|---|---|---|
| tca ggg ctc gga aag gcg atg gcc att cgc ttc ggc aag gag cag gca<br>Ser Gly Leu Gly Lys Ala Met Ala Ile Arg Phe Gly Lys Glu Gln Ala<br>             20                  25                   30 | | 96 |
| aaa gtg gtt atc aac tat tat agt aat aaa caa gat ccg aac gag gta<br>Lys Val Val Ile Asn Tyr Tyr Ser Asn Lys Gln Asp Pro Asn Glu Val<br>           35                  40                   45 | | 144 |
| aaa gaa gag gtc atc aag gcg ggc ggt gaa gct gtt gtc gtc caa gga<br>Lys Glu Glu Val Ile Lys Ala Gly Gly Glu Ala Val Val Val Gln Gly<br> 50                        55                   60 | | 192 |
| gat gtc acg aaa gag gaa gat gta aaa aat atc gtg caa acg gca att<br>Asp Val Thr Lys Glu Glu Asp Val Lys Asn Ile Val Gln Thr Ala Ile<br>65                  70                  75                  80 | | 240 |
| aag gag ttc ggc aca ctc gat att atg att aat aat gcc ggt ctt gaa<br>Lys Glu Phe Gly Thr Leu Asp Ile Met Ile Asn Asn Ala Gly Leu Glu<br>                   85                  90               95 | | 288 |
| aat cct gta cca tct cac gaa atg ccg ctc aag gat tgg gat aaa gtc<br>Asn Pro Val Pro Ser His Glu Met Pro Leu Lys Asp Trp Asp Lys Val<br>             100                 105             110 | | 336 |
| atc agc acg aac tta acg ggt gcc ttt tta gga agc cgt gaa gcg att<br>Ile Ser Thr Asn Leu Thr Gly Ala Phe Leu Gly Ser Arg Glu Ala Ile<br>           115                 120             125 | | 384 |
| aaa tat ttc gta gaa aac gat atc aag gga aat gtc att aac atg tcc<br>Lys Tyr Phe Val Glu Asn Asp Ile Lys Gly Asn Val Ile Asn Met Ser<br>130                 135                 140 | | 432 |
| agt gtg cac gaa gtg att cct tgg cca tta ttt gtc cac tat gcg gca<br>Ser Val His Glu Val Ile Pro Trp Pro Leu Phe Val His Tyr Ala Ala<br>145                 150                 155             160 | | 480 |
| agt aaa ggc ggg atg aag ctg atg aca aaa aca tta gcg ttg gaa tac<br>Ser Lys Gly Gly Met Lys Leu Met Thr Lys Thr Leu Ala Leu Glu Tyr<br>                  165                 170             175 | | 528 |
| gcg ccg aag ggc att cgc gtc aat aat att ggg cca ggt gcg atc aac<br>Ala Pro Lys Gly Ile Arg Val Asn Asn Ile Gly Pro Gly Ala Ile Asn<br>           180                 185             190 | | 576 |
| acg acg atc aat aag gag aaa ttt gct gac tct gaa cag aga gct gat<br>Thr Thr Ile Asn Lys Glu Lys Phe Ala Asp Ser Glu Gln Arg Ala Asp<br>           195                 200             205 | | 624 |
| gta gaa agc atg att cca atg gga tat atc ggc gaa ccg gag gag atc<br>Val Glu Ser Met Ile Pro Met Gly Tyr Ile Gly Glu Pro Glu Glu Ile<br>210                 215                 220 | | 672 |
| gcc gca gta gca gcc tgg ctt gct tcg aag gaa gcc agc tac gtc aca<br>Ala Ala Val Ala Ala Trp Leu Ala Ser Lys Glu Ala Ser Tyr Val Thr<br>225                 230                 235             240 | | 720 |
| ggc atc acg tta ttc gcg gac ggc ggt atg aca caa tat cct tca ttt<br>Gly Ile Thr Leu Phe Ala Asp Gly Gly Met Thr Gln Tyr Pro Ser Phe<br>                  245                 250             255 | | 768 |
| cag gca ggc cgc ggt taa tga<br>Gln Ala Gly Arg Gly<br>           260 | | 789 |

<210> SEQ ID NO 166
<211> LENGTH: 261
<212> TYPE: PRT
<213> ORGANISM: Artificial
<220> FEATURE:
<223> OTHER INFORMATION: derived from bacillus

<400> SEQUENCE: 166

Met Tyr Pro Asp Leu Lys Gly Lys Val Val Ala Ile Thr Gly Ala Ala
1               5                   10                  15

```
Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
 50                  55                  60

Asp Val Thr Lys Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Met Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Ser Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 167
<211> LENGTH: 789
<212> TYPE: DNA
<213> ORGANISM: Artificial
<220> FEATURE:
<223> OTHER INFORMATION: derived from bacillus
<220> FEATURE:
<221> NAME/KEY: misc_feature
<223> OTHER INFORMATION: based upon B. subtilis GDH backbone
<220> FEATURE:
<221> NAME/KEY: CDS
<222> LOCATION: (1)..(789)

<400> SEQUENCE: 167 atg tat ccg gat tta aaa gga aaa gtc gtc gct att aca gga gct act    48
Met Tyr Pro Asp Leu Lys Gly Lys Val Val Ala Ile Thr Gly Ala Thr
 1               5                  10                  15 tca ggg ctc gga aag gcg atg gcc att cgc ttc ggc aag gag cag gca    96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta   144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga   192
Lys Glu Glu Val Ile Lys Ala Gly Gly Glu Ala Val Val Val Gln Gly
 50                  55                  60
```

-continued

```
gat gtc acg aaa gag gaa gat gta aaa aat atc gtg caa acg gca att      240
Asp Val Thr Lys Glu Glu Asp Val Lys Asn Ile Val Gln Thr Ala Ile
 65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                 85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
    130                 135                 140 agt gtg cac gaa gtg att cct tgg cca tta ttt gtc cac tat gcg gca      480
Ser Val His Glu Val Ile Pro Trp Pro Leu Phe Val His Tyr Ala Ala
145                 150                 155                 160 agt aaa ggc ggg atg aag ctg atg aca gaa aca tta gcg ttg gaa tac      528
Ser Lys Gly Gly Met Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg acg atc aat aag gag aaa ttt gct gac cct gaa cag aga gct gat      624
Thr Thr Ile Asn Lys Glu Lys Phe Ala Asp Pro Glu Gln Arg Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
Gly Ile Thr Leu Phe Ala Asp Gly Gly Met Thr Gln Tyr Pro Ser Phe
                245                 250                 255 cag gca ggc cgc ggt taa tga                                          789
Gln Ala Gly Arg Gly
            260
```

<210> SEQ ID NO 168
<211> LENGTH: 261
<212> TYPE: PRT
<213> ORGANISM: Artificial
<220> FEATURE:
<223> OTHER INFORMATION: derived from bacillus

<400> SEQUENCE: 168

```
Met Tyr Pro Asp Leu Lys Gly Lys Val Val Ala Ile Thr Gly Ala Thr
  1               5                  10                  15

Ser Gly Leu Gly Lys Ala Met Ala Ile Arg Phe Gly Lys Glu Gln Ala
                 20                  25                  30

Lys Val Val Ile Asn Tyr Tyr Ser Asn Lys Gln Asp Pro Asn Glu Val
             35                  40                  45

Lys Glu Val Ile Lys Ala Gly Gly Glu Ala Val Val Val Gln Gly
         50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
```

```
                    85                  90                  95
Asn Pro Val Pro Ser His Glu Met Pro Leu Lys Asp Trp Asp Lys Val
            100                 105                 110
Ile Gly Thr Asn Leu Thr Gly Ala Phe Leu Gly Ser Arg Glu Ala Ile
            115                 120                 125
Lys Tyr Phe Val Glu Asn Asp Ile Lys Gly Asn Val Ile Asn Met Ser
            130                 135                 140
Ser Val His Glu Val Ile Pro Trp Pro Leu Phe Val His Tyr Ala Ala
145                 150                 155                 160
Ser Lys Gly Gly Met Lys Leu Met Thr Glu Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Thr Ile Asn Lys Glu Lys Phe Ala Asp Pro Glu Gln Arg Ala Asp
            195                 200                 205
Val Glu Ser Met Ile Pro Met Gly Tyr Ile Gly Glu Pro Glu Glu Ile
            210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Gln Tyr Pro Ser Phe
                245                 250                 255
Gln Ala Gly Arg Gly
            260

<210> SEQ ID NO 169
<211> LENGTH: 261
<212> TYPE: PRT
<213> ORGANISM: Artificial
<220> FEATURE:
<223> OTHER INFORMATION: derived from bacillus
<220> FEATURE:
<221> NAME/KEY: misc_feature
<222> LOCATION: (11)..(11)
<223> OTHER INFORMATION: Xaa is Ala or Asp
<220> FEATURE:
<221> NAME/KEY: misc_feature
<222> LOCATION: (16)..(16)
<223> OTHER INFORMATION: Xaa is Ala or Thr
<220> FEATURE:
<221> NAME/KEY: misc_feature
<222> LOCATION: (46)..(46)
<223> OTHER INFORMATION: Xaa is Asn or Asp
<220> FEATURE:
<221> NAME/KEY: misc_feature
<222> LOCATION: (47)..(47)
<223> OTHER INFORMATION: Xaa is Glu, Asp, or Lys
<220> FEATURE:
<221> NAME/KEY: misc_feature
<222> LOCATION: (54)..(54)
<223> OTHER INFORMATION: Xaa is Lys or Arg
<220> FEATURE:
<221> NAME/KEY: misc_feature
<222> LOCATION: (63)..(63)
<223> OTHER INFORMATION: Xaa is Gln or Arg
<220> FEATURE:
<221> NAME/KEY: misc_feature
<222> LOCATION: (68)..(68)
<223> OTHER INFORMATION: Xaa is Lys or Asn
<220> FEATURE:
<221> NAME/KEY: misc_feature
<222> LOCATION: (75)..(75)
<223> OTHER INFORMATION: Xaa is Ile or Val
<220> FEATURE:
<221> NAME/KEY: misc_feature
<222> LOCATION: (92)..(92)
<223> OTHER INFORMATION: Xaa is Asn or Ser
<220> FEATURE:
```

```
<221> NAME/KEY: misc_feature
<222> LOCATION: (95)..(95)
<223> OTHER INFORMATION: Xaa is Leu or Phe
<220> FEATURE:
<221> NAME/KEY: misc_feature
<222> LOCATION: (96)..(96)
<223> OTHER INFORMATION: Xaa is Glu or Ala
<220> FEATURE:
<221> NAME/KEY: misc_feature
<222> LOCATION: (114)..(114)
<223> OTHER INFORMATION: Xaa is Gly or Ser
<220> FEATURE:
<221> NAME/KEY: misc_feature
<222> LOCATION: (165)..(165)
<223> OTHER INFORMATION: Xaa is Ile, Met, Leu, Val, or Thr
<220> FEATURE:
<221> NAME/KEY: misc_feature
<222> LOCATION: (170)..(170)
<223> OTHER INFORMATION: Xaa is Glu or Lys
<220> FEATURE:
<221> NAME/KEY: misc_feature
<222> LOCATION: (178)..(178)
<223> OTHER INFORMATION: Xaa is Pro or Gln
<220> FEATURE:
<221> NAME/KEY: misc_feature
<222> LOCATION: (194)..(194)
<223> OTHER INFORMATION: Xaa is Pro or Thr
<220> FEATURE:
<221> NAME/KEY: misc_feature
<222> LOCATION: (197)..(197)
<223> OTHER INFORMATION: Xaa is Ala or Lys
<220> FEATURE:
<221> NAME/KEY: misc_feature
<222> LOCATION: (198)..(198)
<223> OTHER INFORMATION: Xaa is Glu, Ala, Asp, Gly, Lys, or Leu
<220> FEATURE:
<221> NAME/KEY: misc_feature
<222> LOCATION: (200)..(200)
<223> OTHER INFORMATION: Xaa is Phe, Met, or Tyr
<220> FEATURE:
<221> NAME/KEY: misc_feature
<222> LOCATION: (201)..(201)
<223> OTHER INFORMATION: Xaa is Ala, Gly, Leu, Ser, or Thr
<220> FEATURE:
<221> NAME/KEY: misc_feature
<222> LOCATION: (202)..(202)
<223> OTHER INFORMATION: Xaa is Asp or Asn
<220> FEATURE:
<221> NAME/KEY: misc_feature
<222> LOCATION: (203)..(203)
<223> OTHER INFORMATION: Xaa is Pro, Asp, Asn, Arg, or Ser
<220> FEATURE:
<221> NAME/KEY: misc_feature
<222> LOCATION: (204)..(204)
<223> OTHER INFORMATION: Xaa is Lys, Asp, Glu, Leu, Asn, Thr, or Gln
<220> FEATURE:
<221> NAME/KEY: misc_feature
<222> LOCATION: (205)..(205)
<223> OTHER INFORMATION: Xaa is Gln or Asn
<220> FEATURE:
<221> NAME/KEY: misc_feature
<222> LOCATION: (206)..(206)
<223> OTHER INFORMATION: Xaa is Lys or Arg
<220> FEATURE:
<221> NAME/KEY: misc_feature
<222> LOCATION: (209)..(209)
<223> OTHER INFORMATION: Xaa is Val or Ala
<220> FEATURE:
<221> NAME/KEY: misc_feature
<222> LOCATION: (210)..(210)
<223> OTHER INFORMATION: Xaa is Glu, Ala, or Lys
<220> FEATURE:
<221> NAME/KEY: misc_feature
<222> LOCATION: (211)..(211)
<223> OTHER INFORMATION: Xaa is Ser, Gly, or Thr
<220> FEATURE:
<221> NAME/KEY: misc_feature
<222> LOCATION: (212)..(212)
<223> OTHER INFORMATION: Xaa is Met or Lys
```

```
<220> FEATURE:
<221> NAME/KEY: misc_feature
<222> LOCATION: (216)..(216)
<223> OTHER INFORMATION: Xaa is Gly or Leu
<220> FEATURE:
<221> NAME/KEY: misc_feature
<222> LOCATION: (219)..(219)
<223> OTHER INFORMATION: Xaa is Gly or Ala
<220> FEATURE:
<221> NAME/KEY: misc_feature
<222> LOCATION: (220)..(220)
<223> OTHER INFORMATION: Xaa is Glu or Gln
<220> FEATURE:
<221> NAME/KEY: misc_feature
<222> LOCATION: (222)..(222)
<223> OTHER INFORMATION: Xaa is Glu or Asp
<220> FEATURE:
<221> NAME/KEY: misc_feature
<222> LOCATION: (234)..(234)
<223> OTHER INFORMATION: Xaa is Lys, Glu, or Ser
<220> FEATURE:
<221> NAME/KEY: misc_feature
<222> LOCATION: (237)..(237)
<223> OTHER INFORMATION: Xaa is Ser or Cys
<220> FEATURE:
<221> NAME/KEY: misc_feature
<222> LOCATION: (242)..(242)
<223> OTHER INFORMATION: Xaa is Ile or Val
<220> FEATURE:
<221> NAME/KEY: misc_feature
<222> LOCATION: (252)..(252)
<223> OTHER INFORMATION: Xaa is Gln or Leu
<220> FEATURE:
<221> NAME/KEY: misc_feature
<222> LOCATION: (253)..(253)
<223> OTHER INFORMATION: Xaa is Tyr or Cys

<400> SEQUENCE: 169

Met Tyr Pro Asp Leu Lys Gly Lys Val Val Xaa Ile Thr Gly Ala Xaa
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Xaa Xaa Val
        35                  40                  45

Lys Glu Glu Val Ile Xaa Ala Gly Gly Glu Ala Val Val Val Xaa Gly
    50                  55                  60

Asp Val Thr Xaa Glu Glu Asp Val Lys Asn Xaa Val Gln Thr Ala Ile
65                  70                  75                  80

Lys Glu Phe Gly Thr Leu Asp Ile Met Ile Asn Xaa Ala Gly Xaa Xaa
                85                  90                  95

Asn Pro Val Pro Ser His Glu Met Pro Leu Lys Asp Trp Asp Lys Val
            100                 105                 110

Ile Xaa Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Xaa Lys Leu Met Thr Xaa Thr Leu Ala Leu Glu Tyr
                165                 170                 175

Ala Xaa Lys Gly Ile Arg Val Asn Asn Ile Gly Pro Gly Ala Ile Asn
            180                 185                 190

Thr Xaa Ile Asn Xaa Xaa Lys Xaa Xaa Xaa Xaa Xaa Xaa Xaa Ala Asp
        195                 200                 205
```

-continued

```
Xaa Xaa Xaa Xaa Ile Pro Met Xaa Tyr Ile Xaa Xaa Pro Xaa Glu Ile
    210             215             220

Ala Ala Val Ala Ala Trp Leu Ala Ser Xaa Glu Ala Xaa Tyr Val Thr
225             230             235             240

Gly Xaa Thr Leu Phe Ala Asp Gly Gly Met Thr Xaa Xaa Pro Ser Phe
            245             250             255

Gln Ala Gly Arg Gly
            260
```